US012139490B2

(12) United States Patent
Tomesch et al.

(10) Patent No.: US 12,139,490 B2
(45) Date of Patent: *Nov. 12, 2024

(54) PROCESS FOR PREPARING 1-(4-FLUOROPHENYL)-4-((6BR, 10AS)-3-METHYL-2,3,6B,9,10,10A-HEXAHYDRO-1H-PYRIDO[3',4':4,5] PYRROLO[1,2,3-DE]QUINOXALIN-8(7H)-YL)BUTAN-1-ONE

(71) Applicant: INTRA-CELLULAR THERAPIES, INC., New York, NY (US)

(72) Inventors: John Charles Tomesch, Succasunna, NJ (US); Peng Li, New Milford, NJ (US); Wei Yao, New Milford, NJ (US); Qiang Zhang, Somerset, NJ (US); James David Beard, New York, NY (US); Andrew S. Thompson, Mountainside, NJ (US); Hua Cheng, Plainsboro, NJ (US); Lawrence P. Wennogle, Steamboat Springs, CO (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 194 days.

This patent is subject to a terminal disclaimer.

(21) Appl. No.: 17/808,836

(22) Filed: Jun. 24, 2022

(65) Prior Publication Data

US 2022/0332716 A1    Oct. 20, 2022

Related U.S. Application Data

(60) Division of application No. 16/594,603, filed on Oct. 7, 2019, now Pat. No. 11,407,751, which is a continuation of application No. 16/439,361, filed on Jun. 12, 2019, now Pat. No. 10,464,938, which is a continuation of application No. 16/244,796, filed on Jan. 10, 2019, now Pat. No. 10,597,395, which is a continuation of application No. 15/660,762, filed on Jul. 26, 2017, now Pat. No. 10,221,176, which is a continuation of application No. 15/066,962, filed on Mar. 10, 2016, now Pat. No. 9,751,883, which is a continuation of application No. 14/323,545, filed on Jul. 3, 2014, now Pat. No. 9,315,504, which is a continuation of application No. 13/593,097, filed on Aug. 23, 2012, now Pat. No. 8,779,139, which is a division of application No. 12/531,016, filed as application No. PCT/US2008/003340 on Mar. 12, 2008, now Pat. No. 8,309,722.

(60) Provisional application No. 60/906,473, filed on Mar. 12, 2007.

(51) Int. Cl.
C07D 471/16    (2006.01)
C07D 471/04    (2006.01)

(52) U.S. Cl.
CPC ......... *C07D 471/16* (2013.01); *C07D 471/04* (2013.01)

(58) Field of Classification Search
CPC .................................................. C07D 471/16
USPC ........................................................ 544/343
See application file for complete search history.

(56) References Cited

U.S. PATENT DOCUMENTS

| 2,490,813 | A | 12/1949 | Hughes et al. |
| 3,299,078 | A | 1/1967 | Pachter |
| 3,813,392 | A | 5/1974 | Sellstedt et al. |
| 3,914,421 | A | 10/1975 | Rajagopalan |
| 4,115,577 | A | 9/1978 | Rajagopalan |
| 4,183,936 | A | 1/1980 | Rajagopalan |
| 4,219,550 | A | 8/1980 | Rajagopalan |
| 4,238,607 | A | 12/1980 | Rajagopalan |
| 4,522,944 | A | 6/1985 | Doria et al. |
| 4,971,971 | A | 11/1990 | Tokunaga et al. |
| 4,985,432 | A | 1/1991 | Tokunaga et al. |
| 5,576,460 | A | 11/1996 | Buchwald et al. |
| 5,648,539 | A | 7/1997 | Goodbrand et al. |
| 5,648,542 | A | 7/1997 | Goodbrand et al. |
| 5,654,482 | A | 8/1997 | Goodbrand et al. |
| 5,705,697 | A | 1/1998 | Goodbrand et al. |
| 5,723,669 | A | 3/1998 | Goodbrand et al. |
| 5,723,671 | A | 3/1998 | Goodbrand et al. |
| 5,847,166 | A | 12/1998 | Buchwald et al. |
| 5,902,901 | A | 5/1999 | Goodbrand et al. |
| 6,043,370 | A | 3/2000 | Kubo et al. |
| 6,166,226 | A | 12/2000 | Buchwald et al. |
| 6,235,936 | B1 | 5/2001 | Buchwald et al. |
| 6,307,087 | B1 | 10/2001 | Buchwald et al. |
| 6,323,366 | B1 | 11/2001 | Wolfe et al. |
| 6,395,916 | B1 | 5/2002 | Buchwald et al. |
| 6,407,092 | B1 | 6/2002 | Hester et al. |
| 6,465,693 | B2 | 10/2002 | Buchwald et al. |
| 6,541,639 | B2 | 4/2003 | Zhou et al. |

(Continued)

FOREIGN PATENT DOCUMENTS

| EP | 0 856 508 | 8/1998 |
| EP | 1 245 553 | 10/2002 |

(Continued)

OTHER PUBLICATIONS

Avendano et al., "The problem of the existence of C(Ar)-H . . . N Intramolecular Hydrogen Bonds in a Family of 9-Azaphenyl-9H-carbazoles," J. Chem. Soc. Perkin Trans., vol. 2, p. 1547-1555, (1993).
Beletskaya et al., "Pd- and Cu-catalyzed selective arylation of benzotriazole," Tetrahedron Letters, vol. 39, p. 5617-5620, (1998).
Berger et al. "Synthesis of some conformationally restricted analogs of fentanyl." Journal of Medicinal Chemistry, vol. 20, No. 4, p. 600-602, (1977).

(Continued)

*Primary Examiner* — Douglas M Willis
(74) *Attorney, Agent, or Firm* — Hoxie & Associates LLC

(57) ABSTRACT

The present invention provides methods for the preparation of substituted heterocycle fused gamma-carbolines, such as the compound of Formula 2J, as shown below, intermediates (Continued)

useful in producing them and methods for producing such intermediates and such heterocycle fused gamma-carbolines, and as further defined herein.

18 Claims, No Drawings

(56) References Cited

U.S. PATENT DOCUMENTS

| | | | |
|---|---|---|---|
| 6,548,493 | B1 | 4/2003 | Robichaud et al. |
| 6,552,017 | B1 | 4/2003 | Robichaud et al. |
| 6,699,852 | B2 | 3/2004 | Robichaud et al. |
| 6,713,471 | B1 | 3/2004 | Robichaud et al. |
| 6,759,554 | B2 | 7/2004 | Buchwald et al. |
| 6,762,329 | B2 | 7/2004 | Marcoux et al. |
| 6,849,619 | B2 | 2/2005 | Robichaud et al. |
| 6,867,298 | B2 | 3/2005 | Buchwald et al. |
| 6,888,032 | B2 | 5/2005 | Buchwald et al. |
| 6,946,560 | B2 | 9/2005 | Buchwald et al. |
| 7,026,498 | B2 | 4/2006 | Buchwald et al. |
| 7,071,186 | B2 | 7/2006 | Robichaud et al. |
| 7,081,455 | B2 | 7/2006 | Robichaud et al. |
| 7,109,339 | B2 | 9/2006 | Lee et al. |
| 7,115,784 | B2 | 10/2006 | Buchwald et al. |
| 7,183,282 | B2 | 2/2007 | Robichaud et al. |
| 7,223,879 | B2 | 5/2007 | Buchwald et al. |
| RE39,679 | E | 6/2007 | Robichaud et al. |
| RE39,680 | E | 6/2007 | Robichaud et al. |
| 7,238,690 | B2 | 7/2007 | Robichaud et al. |
| 7,247,731 | B2 | 7/2007 | Buchwald et al. |
| 7,323,608 | B2 | 1/2008 | Buchwald et al. |
| 8,309,722 | B2 | 11/2012 | Tomesch et al. |
| 8,598,119 | B2 | 12/2013 | Mates et al. |
| 8,648,077 | B2 | 2/2014 | Tomesch et al. |
| 8,779,139 | B2 | 7/2014 | Tomesch et al. |
| 8,993,572 | B2 | 3/2015 | Mates et al. |
| 9,371,324 | B2 | 6/2016 | Mates et al. |
| 10,077,267 | B2 | 9/2018 | Mates et al. |
| 2001/0008942 | A1 | 7/2001 | Buchwald et al. |
| 2004/0034015 | A1 | 2/2004 | Robichaud et al. |
| 2004/0127482 | A1 | 7/2004 | Robichaud et al. |
| 2004/0186094 | A1 | 9/2004 | Robichaud et al. |
| 2004/0220178 | A1 | 11/2004 | Robichaud et al. |
| 2005/0239768 | A1 | 10/2005 | Lee et al. |
| 2006/0128713 | A1 | 6/2006 | Jolidon et al. |
| 2014/0050783 | A1 | 2/2014 | Mates et al. |
| 2014/0323491 | A1 | 10/2014 | Tomesch et al. |
| 2015/0072964 | A1 | 3/2015 | Mates et al. |
| 2015/0080404 | A1 | 3/2015 | Mates et al. |
| 2016/0194326 | A1 | 7/2016 | Tomesch et al. |
| 2019/0231780 | A1 | 8/2019 | Yao et al. |

FOREIGN PATENT DOCUMENTS

| | | |
|---|---|---|
| EP | 1 254 884 | 11/2002 |
| EP | 1 564 671 | 1/2005 |
| WO | WO 1998/015515 | 4/1998 |
| WO | WO 1999/043643 | 9/1999 |
| WO | WO 2000/002887 | 1/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2002/085838 | 10/2002 |
| WO | WO 2004/013094 | 2/2004 |
| WO | WO 2004/039788 | 5/2004 |
| WO | WO 2004/056324 | 7/2004 |
| WO | WO 2009/114181 | 9/2009 |
| WO | WO 2009/145900 | 12/2009 |
| WO | WO 2013/155504 | 10/2013 |
| WO | WO 2013/155506 | 10/2013 |
| WO | WO 2014/145192 | 9/2014 |
| WO | WO 2015/085004 | 6/2015 |
| WO | WO 2019/102240 | 5/2019 |

OTHER PUBLICATIONS

Boger et al., J. Org. Chem., vol. 50, pp. 5782-5789, (1985).
Bowman, W.R., "Synthesis of 1H-quinazoline-4-ones using intramolecular aromatic nucleophilic substitution," arkivoc, vol. x, p. 434-442, (2003).
Bowman et al., "Intramolecular Aromatic Substitution (SRN1) Reactions—Use of Entrainment for the Preparation of Benzothiazoles," Tetrahedron Letters, vol. 23, p. 5093-5096, (1982).
Bowman et al., Tetrahedron Letters, vol. 25, p. 5821-5824, (1984).
Crawford et al., Tetrahedron Letters, vol. 43, p. 7365-7368, (2002).
Evindar et al., Organic Letters, vol. 5, No. 2, p. 133-136, (2003).
Ezquerra et al., J. Org. Chem., vol. 61, p. 5804-5812, (1996).
Fee et al., "Copper (II)-promoted solvolyses of nickel (II) complexes III. Tetradentate Schiff base ligands containing various diamine segments," Aust. J. Chem., vol. 26, p. 1475-1485, (1973).
Ferreira et al., Tetrahedron, vol. 58, p. 7943-7949, (2002).
Finet et al., "Recent advances in ullmann reaction: copper(II) diacetate catalysed N-,)- and S-arylation involving polycoordinate heteroatomic derivatives," Current Organic Chemistry, vol. 6, p. 597-626, (2002).
Goodbrand et al., "Ligand-Accelerated catalysis of the Ullmann condensation: Application to hole conducting triarylamines," J. Org. Chem., vol. 64, p. 670-674, (1999).
Hackam et al., "Translation of Research Evidence From Animals to Humans," *JAMA*, vol. 296, No. 14, 4 pages, (2006); DOI: 10.1001/jama.296.14.1731.
Hamann et al., J. Am. Chem. Soc. vol. 120, p. 2694-2703, (1998).
Hartwig, J., "Palladium-catalyzed amination of aryl halides: Mechanism and rational catalyst design," Synlett, p. 329-340, (1996).
Hassan et al., "Aryl-aryl bond formation one century after the discovery of the ullmann reaction," Chem. Rev., vol. 102, p. 1359-1469, (2002).
Ito et al.., "Studies of organic catalytic reactions. VI. The function of pyridine and copper in the Rosenmund-von Braun reaction," Bulletin of the Chemical Society of Japan, vol. 41, p. 419-423, (1968).
Jordan, V.C., "Tamoxifen: A Most Unlikely Pioneering Medicine," *Nature Reviews: Drug Discovery*, vol. 2, pp. 205-213, (2003).
Ji et al., "Selective amination of polyhalopyridines catalyzed by a palladium-xantphos complex," Organic Letters, vol. 5, No. 24, p. 4611-4614, (2003).
Kametani et al., Heterocycles, vol. 14, No. 3, p. 277-280, (1980).
Kang et al., "Copper-catalyzed N-arylation of aryl iodides with benzamides or nitrogen heterocycles in the presence of ethylendiamine," Synlett, No. 3, p. 427-430, (2002).
Kiyomori et al., "An efficient copper-catalyzed coupling of aryl halides with imidazoles," Tetrahedron Letters, vol. 40, p. 2657-2660, (1999).
Klapars et al., "A general and efficient copper catalyst for the amidation of aryl halides and the N-arylation of nitrogen heterocycles," J. Am. Chem. Soc., vol. 123, p. 7727-7729, (2001).
Klapars et al., "A general and efficient copper catalyst for the amidation of aryl halides," J. Am. Chem. Soc., vol. 124, p. 7421-7428, (2002).
Kondratov et al., "Nucelophilic substitution in the aromatic series. Lv. Reaction of o-nitrochlorobenzene with ammonia in the presence of copper compounds," Zhurnal Organidreskoi Khimii, vol. 51, No. 11, p. 2387-2390, (1979).
Kwong et al., "Mild and efficient copper-catalyzed amination of aryl bromides with primary alkylamines," Organic Letters, vol. 5, No. 6, p. 793-796, (2003).
Lee et al. "Novel, Highly Potent, Selective 5-HT2A/D2 Receptor Antagonists as Potential Atypical Antipsychotics," Bioorg. Med. Chem. Lett. vol. 13, p. 767-770, (2003).
Li et al., "Discovery of a Tetracyclic Quinoxaline Derivative as a Potent and Orally Active Multifunctional Drug Candidate for the Treatment of Neuropsychiatric and Neurological Disorders," J Med Chem., vol. 57, pp. 2670-2682, (2014).
Louie et al., Tetrahedron Letters, vol. 36, No. 21, pp. 3609-3612, (1995).
Marcoux et al., "A general copper-catalyzed synthesis of diaryl ethers," J. Am. Chem. Soc., vol. 119, p. 10539-10540, (1997).

(56) References Cited

OTHER PUBLICATIONS

Mulrooney, C.A., "Recent developments in copper-catalyzed n-arylation with aryl halides," Essay—University of Pennsylvania.

Murakami et al., Chem. Pharm. Bull, vol. 43, No. 8, p. 1281-1286, (1995).

Nagai et al. "Synthesis of 2, 3, 4, 4a, 5, 9b-hexahydro-1H-pyrido [4,3-b] indole derivatives and their central nervous system activities." Journal of Medicinal Chemistry, vol. 22, No. 6, p. 677-683, (1979).

Protective Groups in Organic Synthesis, Third Edition, John Wiley & Sons, Inc., p. 494-505, (1999).

Rackova et al. "Free Radical Scavenging and Antioxidant Activities of Substituted Hexahydropyridoindoles. Quantitative Structure-Activity Relationships." Journal of Medicinal Chemistry, vol. 49, No. 8, p. 2543-2548, (2006).

Sadighi et al., "A highly active palladium catalyst system for the arylation of anilines," Tetrahedron Letters, vol. 39, p. 5327-5330, (1998).

Serajuddin, A., "Salt Formation to Improve Drug Solubility," Advanced Drug Delivery Reviews, vol. 59, pp. 603-616, (2007).

Sigel et al., Inorganic Chemistry, vol. 13, No. 2, p. 462-465, (1974).

Sugahara et al., Chem. Pharm. Bull., vol. 45, No. 4, p. 719-721, (1997).

Wagaw et al., "A palladium-catalyzed method for the preparation of indoles via the Fischer indole synthesis," Journal of the American Chemical Society, vol. 121, No. 44, p. 10251-10263, (1999).

Wolfe, J.P., "An improved catalyst system for aromatic carbon-nitrogen bond formation: The possible involvement of bis(phosphine) palladium complexes as key intermediates," JACS, vol. 118, p. 7215-7216, (1996).

Wolfe et al., "Intramolecular palladium-catalyzed aryl amination and aryl amidation," Tetrahedron, vol. 52, No. 21, p. 7525-7546, (1996).

Wolter et al., "Synthesis of N-aryl hydrazides by copper-catalyzed coupling of hydrazides with aryl iodides," Organic Letters, vol. 3, No. 23, p. 3803-3805, (2001).

Yamada et al., "A mild copper-mediated intramolecular amination of aryl halides," Synlett, No. 2, p. 231-234, (2002).

Yang, B.H., "The development of efficient protocols for the palladium-catalyzed cyclization reactions of secondary amides and carbamates," Organic Letters, vol. 1, No. 1, p. 35-37, (1999).

Zaragoza Dörwald, F., "Side Reactions in Organic Synthesis: A Guide to Successful Synthesis Design," Wiley-VCH, 6 pages, (2005).

Zhang et al., Catalysis Communications, vol. 6, p. 784-787, (2005).

PROCESS FOR PREPARING 1-(4-FLUOROPHENYL)-4-((6BR, 10AS)-3-METHYL-2,3,6B,9,10,10A-HEXAHYDRO-1H-PYRIDO[3',4':4,5] PYRROLO[1,2,3-DE]QUINOXALIN-8(7H)-YL) BUTAN-1-ONE

RELATED APPLICATIONS

This application is a divisional of U.S. application Ser. No. 16/594,603, filed on Oct. 7, 2019, which is a continuation application of U.S. application Ser. No. 16/439,361, filed on Jun. 12, 2019, which is a continuation application of U.S. application Ser. No. 16/244,796, filed on Jan. 10, 2019, which is a continuation application of U.S. application Ser. No. 15/660,762, filed on Jul. 26, 2017, which is a continuation application of U.S. application Ser. No. 15/066,962, filed on Mar. 10, 2016, which is a continuation application of U.S. Application Ser. No. 14/323,545, filed on Jul. 3, 2014, which is a continuation application of U.S. Application Ser. No. 13/593,097, filed on Aug. 23, 2012, which is a divisional application of U.S. Application Ser. No. 12/531,016, filed on Jan. 12, 2010, which is a United States Application under 35 U.S.C. 371 claiming benefit of PCT Application No. PCT/US2008/003340, filed on Mar. 12, 2008, which claims priority from U.S. Provisional Application No. 60/906,473, filed on Mar. 12, 2007, the contents of each of which are hereby incorporated by reference in their entireties.

FIELD OF THE INVENTION

The present invention relates to a method for the preparation of substituted heterocycle fused gamma-carbolines, intermediates useful for producing them, and a method for producing such intermediates.

BACKGROUND OF THE INVENTION

Substituted heterocycle fused gamma-carbolines are useful as agonists or antagonists of 5-HT2 receptors, particularly 5-HT2A and 5-HT2C receptors, in treating central nervous system disorders, including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

Traditional methods for the preparation of enantiomerically pure substituted heterocycle fused gamma-carbolines involve Fischer indole cyclization of aryl hydrazine (e.g., dihydroquinoxalin-1-(2H)-amine, 2H-benzo[b][1,4]oxazin-4(3H)-amine or 2H-benzo[b][1,4]thiazin-4(3H)-amine) with suitably substituted cyclic ketones (e.g., piperidin-4-one) to afford tetracyclic indole compounds (e.g., 1,3,7,8,9,10-hexahydro-1H-pyrido-[3',4':4,5]-pyrrolo[1,2,3-de]quinoxaline). This indole core is then reduced to afford the cis or trans tetracyclic dihydroindole (i.e., cis or trans tetracyclic indoline) product, which requires exhaustive purification procedures such as chiral column chromatography to afford enantiomerically pure product. This method as a whole is inefficient because excess reagents and reaction intermediates are required to produce racemic products, wherein such product is purified at the final step to give a 25-50% yield at best. There is thus a need for a more efficient process to make enantiomerically pure substituted heterocycle fused gamma-carbolines.

SUMMARY OF THE INVENTION

The present invention provides methods for the preparation of substituted heterocycle fused gamma-carbolines in free or pharmaceutically acceptable salt forms, intermediates used in the preparation, for example enantiomerically pure 2,3,4,4a,5,9b-hexahydro-1H-pyrido[4,3-b]indole type intermediates, and methods for producing said intermediates and said substituted heterocycle fused gamma-carbolines are disclosed in the present invention.

Substituted heterocycle fused gamma-carbolines and their pharmaceutically acceptable salts produced by the present invention are represented by the core structure shown in Formula 1J:

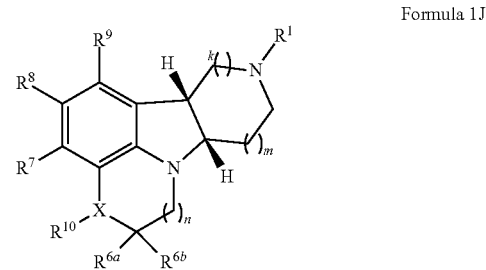

Formula 1J

Exemplary representations of compounds of the invention and $R^1$, $R^{6a}$, $R^{6b}$, $R^7$, $R^8$, $R^9$, $R^{10}$, X, k, m, and n are as described in U.S. Pat. Nos. 6,552,017; 6,548,493; 6,713,471; and 6,849,619, U.S. Reissued Pat. Nos. 39,680 and 38,679, and U.S. application Ser. Nos. 10/787,941 and 10/786,935, the contents of each of which are all incorporated herein by reference. These compounds have been found to be useful as 5-HT2 receptor agonists and antagonists used in treating disorders of the central nervous system including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

Accordingly, the present invention provides substantially enantiomerically pure cis dihydroindole (or indoline) type compounds as disclosed below in formulas 1C, 1D, 1E, 1E', 1F" and 1G', e.g., at least 70%, preferably 80%, more preferably at least 90%, most preferably greater than 95% cis compounds of the following formulas (e.g., 1C, 1D, 1E, 1E', 1F" and 1G') relative to all of their other stereoisomers, in free or pharmaceutically acceptable salt form, which are useful, e.g., as intermediates for the production of compounds of Formula 1J:

1.1: Compounds of Formula 1C:

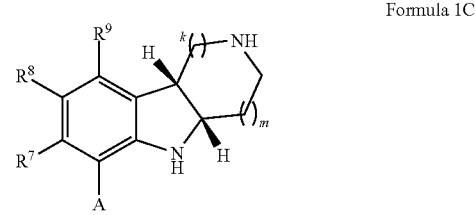

Formula 1C wherein:
 (i) k is 1 or 2;
 (ii) m is 0, 1 or 2;
 (iii) A=Cl, Br, F or I;
 (iv) $R^7$, $R^8$ and $R^9$ are independently H or optionally substituted $C_1$-$C_6$alkyl, alkenyl, alkynyl, cycloalkyl, heterocycloalkyl, hydroxy, alkoxy, nitro, halo, haloalkyl, aryl, arylalkyl, heteroaryl or heteroarylalkyl.

1.2: Compounds of Formula 1D:

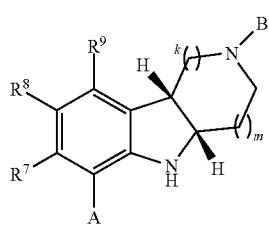

Formula 1D wherein:
 (i) k is 1 or 2;
 (ii) m is 0, 1 or 2;
 (iii) A=Cl, Br, F or I;
 (iv) B is a protective group;
 (v) $R^7$, $R^8$ and $R^9$ are independently H or optionally substituted $C_1$-$C_6$alkyl, alkenyl, alkynyl, cycloalkyl, heterocycloalkyl, hydroxy, alkoxy, nitro, halo, haloalkyl, aryl, arylalkyl, heteroaryl or heteroarylalkyl.

1.3: Compounds of Formula 1E':

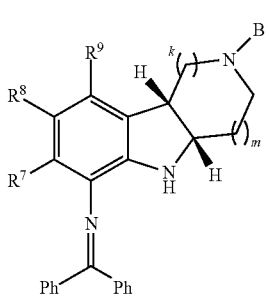

Formula 1E' wherein:
 (i) k is 1 or 2;
 (ii) m is 0, 1 or 2;
 (iii) B is a protective group.
 (iv) $R^7$, $R^8$ and $R^9$ are independently H or optionally substituted $C_1$-$C_6$alkyl, alkenyl, alkynyl, cycloalkyl, heterocycloalkyl, hydroxy, alkoxy, nitro, halo, haloalkyl, aryl, arylalkyl, heteroaryl or heteroarylalkyl.

1.4: Compounds of Formula 1E:

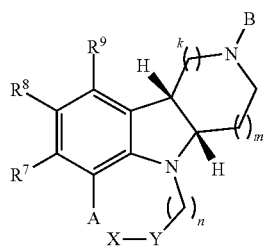

Formula 1E wherein:
 (i) k is 1 or 2;
 (ii) m is 0, 1 or 2;
 (iii) n is 1, 2 or 3;
 (iv) A=Cl, Br, F or I;
 (v) B is a protective group;
 (vi) $R^7$, $R^8$ and $R^9$ are $R^7$, $R^8$ and $R^9$ are independently H or optionally substituted $C_1$-$C_6$alkyl, alkenyl, alkynyl, cycloalkyl, heterocycloalkyl, hydroxy, alkoxy, nitro, halo, haloalkyl, aryl, arylalkyl, heteroaryl or heteroarylalkyl; and
 (vii) X—Y— is a HO—$CH_2$—, HS—$CH_2$—, H(R')N—$CH_2$— or H(R')N—C(O)—, wherein R' is H or $C_{1-4}$alkyl.

1.5: Compounds of Formula 1F''

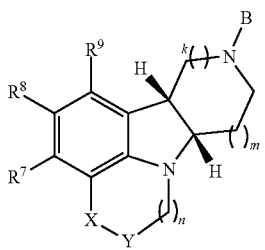

Formula 1F'' wherein:
 (i) k is 1 or 2;
 (ii) m is 0, 1 or 2;
 (iii) n is 1, 2 or 3;
 (iv) B is a protective group;
 (v) $R^7$, $R^8$ and $R^9$ are $R^7$, $R^8$ and $R^9$ are independently H or optionally substituted $C_1$-$C_6$alkyl, alkenyl, alkynyl, cycloalkyl, heterocycloalkyl, hydroxy, alkoxy, nitro, halo, haloalkyl, aryl, arylalkyl, heteroaryl or heteroarylalkyl; and
 (vi) —X—Y— is —(R')N—C(O)—, wherein R' is H or $C_{1-4}$alkyl.

1.6: Compounds of Formula 1G':

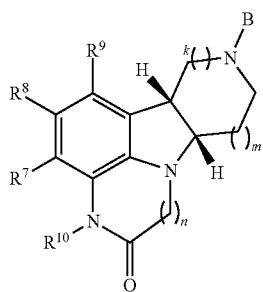

Formula 1G' wherein:
(i) k is 1 or 2;
(ii) m is 0, 1 or 2;
(iii) n is 1, 2 or 3;
(iv) B is a protective group;
(v) $R^7$, $R^8$ and $R^9$ are $R^7$, $R^8$ and $R^9$ are independently H or optionally substituted $C_1$-$C_6$alkyl, alkenyl, alkynyl, cycloalkyl, heterocycloalkyl, hydroxy, alkoxy, nitro, halo, haloalkyl, aryl, arylalkyl, heteroaryl or heteroarylalkyl; and
(vi) $R^{10}$ is $C_{1-4}$alkyl, alkenyl or alkynyl.

The invention further provides compounds of the following formulae:

2.1. Formula 1G', wherein $R^{10}$ is $C_1$-$C_4$alkyl, alkenyl or alkynyl.
2.2. Formula 1G', wherein $R^{10}$ is methyl.
2.3. Formula 1F''', wherein —X—Y— is —(R')N—C(O)—, wherein R' is H or $C_{1-4}$alkyl.
2.4. Any of Formulae 1F''', 1G' or 2.1-2.3, wherein n is 1, 2 or 3.
2.5. Any of Formulae 1F''', 1G or 2.1-2.3, wherein n is 1.
2.6. Formula 1E, wherein X—Y— is HO—$CH_2$—, HS—$CH_2$—, H(R')N—$CH_2$— or H(R')N—C(O)— and R' is H or $C_{1-4}$alkyl.
2.7. Formula 1E, wherein X—Y— is H(R')N—$CH_2$— and R' is H or $C_{1-4}$alkyl.
2.8. Any of Formulae 1D, 1E, 1E', 1F''', 1G' or 2.1-2.7, wherein B is a protective group.
2.9. Any of Formulae 1D, 1E, 1E', 1F''', 1G' or 2.1-2.7, wherein B has a general formula of —P—Z, wherein P is —C(O)—, —C(O)O—, or —S(O)$_2$— and Z is alkyl or arylalkyl.
2.10. Any of Formulae 1D, 1E, 1E', 1F''', 1G' or 2.1-2.7, wherein B is —C(O)Oalkyl.
2.11. Any of Formulae 1D, 1E, 1E', 1F''', 1G' or 2.1-2.7, wherein B is —C(O)OEt or —C(O)OiPr.
2.12. Any of Formulae 1C, 1D or 2.8-2.11, wherein A is Cl, Br, F or I.
2.13. Any of Formulae 1C, 1D or 2.8-2.11, wherein A is Cl.
2.14. Any of Formulae 1C, 1D, 1E, 1E' 1F''', 1G' or 2.1-2.13, wherein $R^7$, $R^8$ and $R^9$ are independently H or optionally substituted $C_1$-$C_6$ alkyl, alkenyl, alkynyl, cycloalkyl, heterocycloalkyl, hydroxy, alkoxy, nitro, halo, haloalkyl, aryl, arylalkyl, heteroaryl or heteroarylalkyl.
2.15. Any of Formulae 1C, 1D, 1E, 1E' 1F', 1G' or 2.1-2.13, wherein $R^7$, $R^8$, and $R^9$ are H.
2.16. Any of Formulae 1C, 1D, 1E, 1E' 1F', 1G' or 2.1-2.15, wherein k and m are independently 0, 1, 2 or 3.
2.17. Any of Formulae 1C, 1D, 1E, 1E' 1F', 1G' or 2.1-2.15, wherein k and m are 1.
2.18. Any of the preceding formulae wherein alkyl, alkenyl, alkynyl, alkoxy and haloalkyl independently comprises 1-6 carbon atoms.
2.19. Any of the preceding formulae wherein the alkyl of arylalkyl and heteroarylalkyl is independently 1-6 carbon atoms.
2.20. Any of the preceding formulae wherein cycloalkyl and heterocycloalkyl is independently 3-10 carbon atoms
2.21. Any of the preceding formulae wherein said compounds are at least 70%, preferably 80%, more preferably at least 90%, most preferably greater than 95% cis compounds of the following formulas (e.g., 1C, 1D, 1E, 1E', 1F''' and 1G') relative to all of their other stereoisomers, in free or pharmaceutically acceptable salt form.

The present invention further provides substantially optically pure cis dihydroindole (or indoline) type compounds as disclosed below in formulas 2C, 2D, 2E, 2E', 2F''' and 2G', e.g., at least 70%, preferably 80%, more preferably at least 90%, most preferably greater than 95% cis isomer relative to all of their trans isomers, in free or pharmaceutically acceptable salt form, which are useful, e.g., as intermediates for the production of compounds of Formula 1J:

1.7: Compounds of Formula 2C:

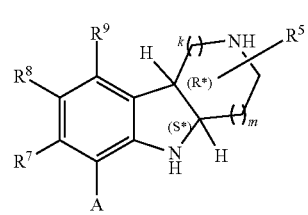

Formula 2C wherein:
(i) k is 1 or 2;
(ii) m is 0, 1 or 2;
(iii) A=Cl, Br, F or I;
(iv) $R^5$ is H or $C_1$-$C_4$alkyl;
(v) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, $C_1$-$C_6$alkoxy, nitro, halo, halo$C_1$-$C_6$alkyl, aryl, aryl$C_1$-$C_6$alkyl, heteroaryl or heteroaryl$C_1$-$C_6$alkyl.

1.8: Compounds of Formula 2D:

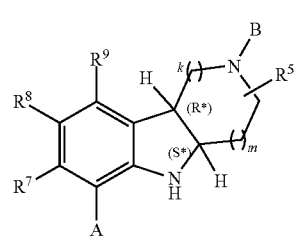

Formula 2D wherein:
(i) k is 1 or 2;
(ii) m is 0, 1 or 2;
(iii) A=Cl, Br, F or I;
(iv) B is a protective group;

(v) $R^5$ is H or $C_1$-$C_4$alkyl;
(vi) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, $C_1$-$C_6$alkoxy, nitro, halo, halo$C_1$-$C_6$alkyl, aryl, aryl$C_1$-$C_6$alkyl, heteroaryl or heteroaryl$C_1$-$C_6$alkyl.

1.9: Compounds of Formula 2E':

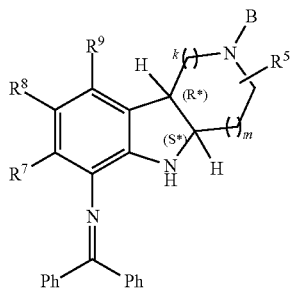

Formula 2E' wherein:
(i) k is 1 or 2;
(ii) m is 0, 1 or 2;
(iii) B is a protective group
(iv) $R^5$ is H or $C_1$-$C_4$alkyl;
(v) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, alkoxy, nitro, halo, halo$C_1$-$C_6$alkyl, aryl, aryl$C_1$-$C_6$alkyl, heteroaryl or heteroaryl$C_1$-$C_6$alkyl.

1.10: Compounds of Formula 2E:

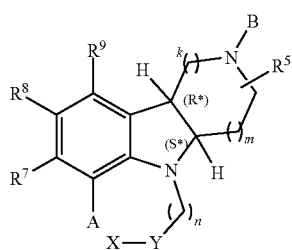

Formula 2E wherein:
(i) k is 1 or 2;
(ii) m is 0, 1 or 2;
(iii) n is 1, 2 or 3;
(iv) A=Cl, Br, F or I;
(v) B is a protective group;
(vi) $R^5$ is H or $C_1$-$C_4$alkyl;
(vii) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, alkoxy, nitro, halo, halo$C_1$-$C_6$alkyl, aryl, aryl$C_1$-$C_6$alkyl, heteroaryl or heteroaryl$C_1$-$C_6$alkyl; and
(viii) X—Y— is a HO—$CH_2$—, HS—$CH_2$—, H(R')N—$CH_2$— or H(R')N—C(O)—, wherein R' is H or $C_1$-$C_4$alkyl.

1.11: Compounds of Formula 2F'''

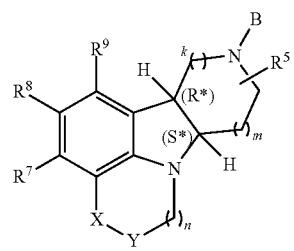

Formula 2F''' wherein:
(i) k is 1 or 2;
(ii) m is 0, 1 or 2;
(iii) n is 1, 2 or 3;
(iv) B is a protective group;
(v) $R^5$ is H or $C_1$-$C_4$alkyl;
(vi) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, $C_1$-$C_6$alkoxy, nitro, halo, halo$C_1$-$C_6$alkyl, aryl, aryl$C_1$-$C_6$alkyl, heteroaryl or heteroaryl$C_1$-$C_6$alkyl; and
(vii) —X—Y— is —(R')N—C(O)—, wherein R' is H or $C_1$-$C_4$alkyl.

1.12: Compounds of Formula 2G:

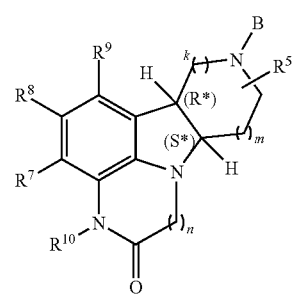

Formula 2G wherein:
(i) k is 1 or 2;
(ii) m is 0, 1 or 2;
(iii) n is 1, 2 or 3;
(iv) B is a protective group;
(v) $R^5$ is H or $C_1$-$C_4$alkyl;
(vi) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, $C_{1-6}$alkoxy, nitro, halo, halo$C_1$-$C_6$alkyl, aryl, aryl$C_1$-$C_6$alkyl, heteroaryl or heteroaryl$C_1$-$C_6$alkyl; and
(vii) $R^{10}$ is H or $C_{1-4}$alkyl.

The invention further provides compounds of the following formulae:
2.22. Formula 2G, wherein $R^{10}$ is H or $C_1$-$C_4$alkyl;
2.23. Formula 2G or 2.22, wherein $R^{10}$ is H;
2.24. Formula 2G or 2.22, wherein $R^{10}$ is methyl;
2.25. Formula 2F'', wherein —X—Y— is —(R')N—C(O)—, wherein R' is H or $C_{1-4}$alkyl;
2.26. Formula 2F'' or 2.25, wherein —X—Y— is —(R')N—C(O)—, wherein R' is H or methyl;
2.27. Formula 2E, wherein X—Y—is HO—$CH_2$—, HS-$CH_2$—, H(R')N—$CH_2$— or H(R')N—C(O)— and R' is H or $C_{1-4}$alkyl;

2.28. Formula 2E or 2.27, wherein X—Y—is H(R')N—CH$_2$— and R' is H or C$_{1-4}$alkyl;
2.29. Formula 2E or any of 2.27-2.28, wherein X—Y—is H(R')N—CH$_2$— and R' is H;
2.30. Formula 2E or any of 2.27-2.29, wherein X—Y—is H(R')N—CH$_2$— and R' is methyl;
2.31. Any of Formulae 2D, 2E, 2E', 2F''', 2G or 2.22-2.30, wherein B is a protective group;
2.32. Any of Formulae 2D, 2E, 2E', 2F''', 2G or 2.22-2.31, wherein B has a general formula of –P–Z, wherein P is —C(O)—, —C(O)O—, or —S(O)$_2$—and Z is alkyl or arylalkyl;
2.33. Any of Formulae 2D, 2E, 2E', 2F''', 2G or 2.22-2.32, wherein B is —C(O)Oalkyl;
2.34. Any of Formulae 2D, 2E, 2E', 2F''', 2G or 2.1-1.7, wherein B is —C(O)OEt or —C(O)OiPr;
2.35. Any of Formulae 2E, 2F''', 2G or 2.22-2.34, wherein n is 1, 2 or 3.
2.36. Any of Formulae 2E, 2F''', 2G or 2.22-2.35, wherein n is 1;
2.37. Any of Formulae 2C, 2D or 2.31-2.36, wherein A is Cl, Br, F or I.
2.38. Any of Formulae 2C, 2D or 2.31-2.37, wherein A is Cl or Br;
2.39. Any of Formulae 2C, 2D, 2E, 2E', 2F''', 2G or 2.22-2.38, wherein $R^7$, $R^8$ and $R^9$ are independently H or optionally substituted C$_1$-C$_6$alkyl, C$_3$-C$_{10}$cycloalkyl, C$_3$-C$_{10}$heterocycloalkyl, hydroxy, C$_{1-6}$alkoxy, nitro, halo, haloC$_1$-C$_6$alkyl, aryl, arylC$_1$-C$_6$alkyl, heteroaryl or heteroarylC$_1$-C$_6$alkyl;
2.40. Any of Formulae 2C, 2D, 2E, 2E', 2F', 2G or 2.22-2.39, wherein $R^7$, $R^8$, and $R^9$ are H;
2.41. Any of Formulae 2C, 2D, 2E, 2E', 2F', 2G or 2.22-2.40, wherein k and m are independently 0, 1, 2 or 3;
2.42. Any of Formulae 2C, 2D, 2E, 2E', 2F', 2G or 2.22-2.41, wherein k and m are 1;
2.43. Any of the preceding formulae wherein k is 1 and m is 1;
2.44. Any of the preceding formulae wherein $R^5$ is H or C$_1$-C$_4$alkyl;
2.45. Any of the preceding formulae wherein $R^5$ is H;
2.46. Any of the preceding formulae wherein alkyl comprises alkyl, alkenyl and/or alkynyl.
2.47. Any of the preceding formulae wherein the two hydrogen atoms at the two chiral carbon atoms are cis to each other, thereby having the general structures as follows:

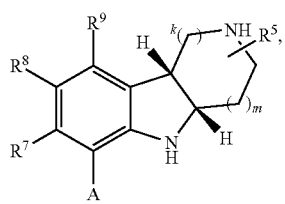

Formula 2C-1

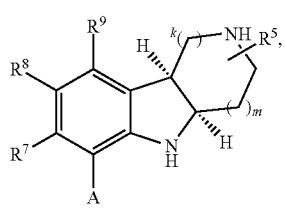

Formula 2C-2

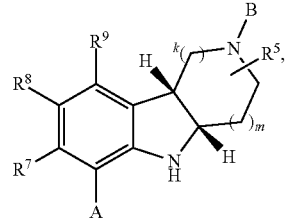

Formula 2D-1

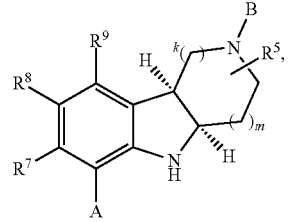

Formula 2D-2

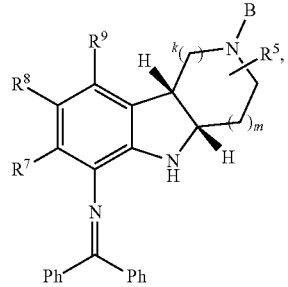

Formula 2E'-1

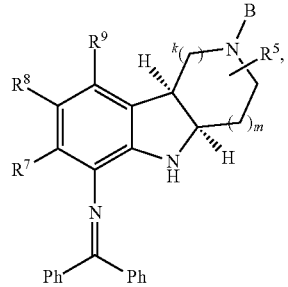

Formula 2E'-2

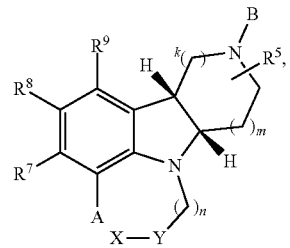

Formula 2E-1

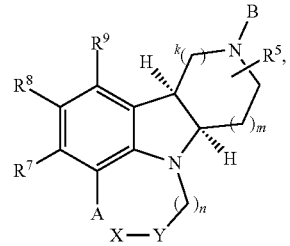

Formula 2E-2

-continued

Formula 2F''-1

Formula 2F''-2

Formula 2G-1 and

Formula 2G-2

2.48. Any of the preceding formulae wherein the cis isomer is selected from formulae 2C-1, 2D-1, 2E-1, 2E'-1, 2F'''-1, and 2G-1;
in free or salt form.

METHOD

In another aspect, the invention provides a method (Method 1C) for preparing compounds of Formula 1C or any of 2.12-2.21:

Formula 1C in free or salt form, as hereinbefore described, which method comprises the steps of:

a) reducing compounds of Formula 1A

Formula 1A to compounds of Formula 1B; and

Formula 1B b) separating the enantiomers of compounds of Formula 1B by chiral acid resolution or chiral chromatography.

In another embodiment, the invention provides a method (Method 2C) for preparing compounds of Formula 1C or any of 2.37-2.48:

Formula 2C in free or salt form, as hereinbefore described, which method comprises the steps of:

a) reducing compounds of Formula 2A

Formula 2A to compounds of Formula 2B; and

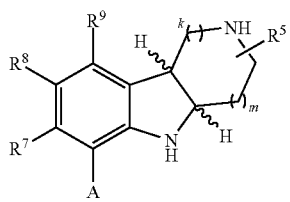

Formula 2B b) separating the enantiomers of compounds of Formula 2B by chiral acid resolution or chiral chromatography.

The reduction of Compounds of Formula 1A to Compounds of Formula 1B may be accomplished through the use of a reducing agent including, but not limited to: silanes in the presence of an acid (e.g., acetic or trifluoroacetic acid); metal (e.g., zinc) and mineral acid (e.g. hydrochloric acid); sodium and liquid ammonia; sodium in ethanol; or through the use of borane-amine complexes (e.g. borane-triethylamine in tetrahydrofuran); or sodium cyanoborohydride in the presence of an acid such as acetic or trifluoroacetic acid. The conversion of Compound of Formula 1A to Formula 1B may also be accomplished through catalytic hydrogenation wherein Compounds of Formula IA is treated with hydrogen in the presence of a catalyst such as palladium oxide, palladium on carbon or platinum oxide (See Hudlicky, M., "Reductions in Organic Chemistry", Ellis Horwood, Ltd., Chichester, UK, 1984). The reduction of Compounds of Formula 2A to Compounds of Formula 2B may be accomplished through the use of similar agents as described for the reduction of Compounds of Formula 1A to 1B, for example silanes (e.g., triethylsilane) in the presence of an acid (e.g., acetic or trifluoroacetic acid); metal (e.g., zinc) and mineral acid (e.g. hydrochloric acid); sodium and liquid ammonia; sodium in ethanol; or through the use of borane-amine complexes (e.g. borane-triethylamine in tetrahydrofuran); $NaBH(OAc)_3$; or sodium cyanoborohydride in the presence of an acid such as acetic or trifluoroacetic acid. The conversion of Compound of Formula 1A to Formula 1B may also be accomplished through catalytic hydrogenation wherein Compounds of Formula IA is treated with hydrogen in the presence of a catalyst such as palladium oxide, palladium on carbon or platinum oxide. In an especially preferred embodiment, reduction is accomplished through the use of triethylsilane in the presence of trifluoroacetic acid.

In one embodiment, enantiomeric separation of compounds of Formula 1B may be achieved by chiral acid resolution wherein chiral acids such as chiral sulphonic acids or mono or di carboxylic acids or derivatives thereof are used. Examples of such acids include, but are not limited to, (+/−)/(R/S) tartaric acid, (+/−)/(R/S) (mono- or di-acetyl) tartaric acid, (+/−)/(R/S) (mono- or di-benzoyl)tartaric acid, (+/−)/(R/S) (mono- or di-pivaloyl)tartaric acid, (+/−)/(R/S) mandelic acid, (+/−)/(R/S) acetoxyphenyl acetic acid, (+/−)/(R/S) methoxyphenyl acetic acid, (+/−)/(R/S) hydroxymandelic acid, (+/−)/(R/S) halomandelic acid (e.g. 4-fluoromandelic acid), (+/−)/(R/S) lactic acid, and (+/−)/(R/S) camphor sulfonic acid. Similarly, the enantiomeric separation of compounds of Formula 2B may be achieved by chiral acid resolution wherein chiral acids such as chiral sulphonic acids or mono or di carboxylic acids or derivatives thereof are used. Examples of such acids include, but are not limited to, (+/−)/(R/S) tartaric acid, (+/−)/(R/S) (mono- or di-acetyl) tartaric acid, (+/−)/(R/S) (mono- or di-benzoyl)tartaric acid, (+/−)/(R/S) (mono- or di-pivaloyl)tartaric acid, (+/−)/(R/S) mandelic acid, (+/−)/(R/S) acetoxyphenyl acetic acid, (+/−)/ (R/S) methoxyphenyl acetic acid, (+/−)/(R/S) hydroxymandelic acid, (+/−)/(R/S) halomandelic acid (e.g. 4-fluoromandelic acid), (+/−)/(R/S) lactic acid, and (+/−)/(R/S) camphor sulfonic acid. Preferably, resolution of compounds of Formula 1B or 2B is accomplished by using mandelic acid. In an especially preferred embodiment, said acid is (S)-(+)-mandelic acid. Resolution may be optimized where undesired enantiomer is removed first. Therefore, in an especially preferred embodiment, resolution is accomplished by adding (R)-(−)-mandelic acid to remove the undesired enantiomer first, followed by the addition of (S)-(+)-mandelic acid to obtain the desired product.

In another embodiment, enantiomeric separation of compounds of Formula 1B may be achieved by using chiral chromatography, for example using amylose tris(3,5-dimethylphenylcarbamate) column sold under the tradename "CHIRALPAK® AD®". The racemic compounds of Formula 1B may be eluted with a mobile phase such as ethanol at a flow rate of 100-450 mL/min. In yet another embodiment, the racemic compounds of Formula 1B may be eluted with mobile phase such as methanol or isopropyl alcohol. The fractions for the desired compounds, preferably, Compounds of Formula 1C or 2C, may be collected and isolated. In one embodiment, chiral chromatography comprises the use of CHIRALPAK® AD®, 20 μm, 5 cm IDx50 cm L column and 100% ethanol mobile phase at a flow rate of 150 mL/min. In another embodiment, chiral chromatography comprises the use of CHIRALPAK® AD®, 20 μm, 11 cm IDx25 cm L column and 100% ethanol mobile phase at a flow rate of 400 mL/min.

In another embodiment, the enantiomeric separation of compounds of Formula 2B may be achieved by using chiral chromatorgraphy as described above in Method for separating Compounds of Formula 1B.

In another aspect, the invention provides a method (Method 1D) for preparing compounds of Formula 1D or any of 2.8-2.21:

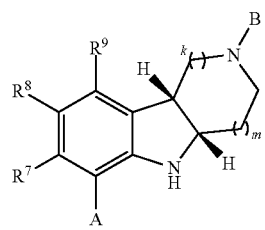

Formula 1D as hereinbefore described in free or salt form, which method comprises the step of protecting the piperidino-amine of compounds of Formula 1C:

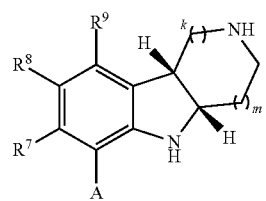

Formula 1C with a protecting agent in the presence of a base.

In a further embodiment, the protecting agent of Method 1D comprises the general formula:

wherein:
(i) Y is halogen, imidazoyl, benzotriazole, N-(oxy)succinimide, alkoxy, —O—alkylaryl or —O—aryl;
(i) Z is optionally substituted alkyl, aryl, alkylaryl or —OR wherein R is alkyl, aryl, arylalkyl or heteroarylalkyl;
(ii) P is —C(O)—, —C(O)O— or S(O)$_2$.

In another embodiment, the invention also provides a method (Method 2D) for preparing compounds of Formula 2D or any of 2.31-2.48:

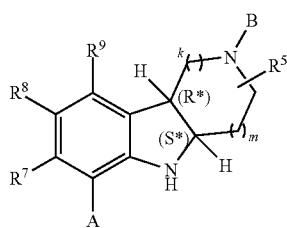

Formula 2D as hereinbefore described in free or salt form, which method comprises the step of protecting the piperidino-amine of compounds of Formula 2C:

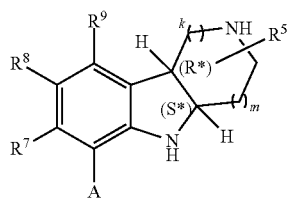

Formula 2C with a protecting agent.

In a further embodiment, the protecting agent of Method 2D comprises the general formula:

wherein:
(iii) Y is halogen, imidazoyl, benzotriazole, N—(oxy)succinimide, alkoxy, alkoxycarbonyl, —O—alkylaryl or —O—aryl;
(ii) Z is optionally substituted alkyl, aryl, alkylaryl, alkoxycarbonyl, or —OR wherein R is alkyl, aryl, arylalkyl or heteroarylalkyl;
(iv) P is —C(O)—, —C(O)O—, —O— or S(O)$_2$.

Examples of the protecting agent of compounds of Formula 1C or 2C include, but are not limited to benzyloxycarbonyl chloride (Cbz-Cl), triphenylmethyl chloride, ethyl chloroformate, t-butoxycarbonyl anhydride (BOC$_2$), benzyl N-succinimidyl carbonate, or benzoyl halide (e.g. benzoyl chloride or bromide), (benzyloxycarbonyl)-benzo triazole, benzyl halide (e.g. benzyl chloride or bromide), 1-arene sulfonyl chloride or toluene sulfonyl chloride. Another example of protecting agent of Compounds of Formula 1C or 2C is p-methoxybenzyl ether. The protective agents disclosed herein are not intended to be exhaustive. For further examples of amine protecting agent, see one of the many general texts on the subject, for example, "Protective Groups in Organic Synthesis" by Theodora Green (publisher: John Wiley & Sons), the disclosure of which is hereby incorporated by reference. Upon addition of the protecting agent to compounds of Formula 1C, substituent B therefore contains a general formula:

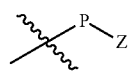

wherein:
(i) Z is optionally substituted alkyl, aryl, alkylaryl or —OR wherein R is alkyl, aryl, arylalkyl or heteroarylalkyl;
(ii) P is —C(O)—, —C(O)O— or S(O)$_2$.

The protection step of this embodiment generally requires the addition of a base such as butyl lithium or metal hydrides (e.g., potassium hydride) or carbonates of alkali or alkaline earth metals (e.g., potassium or sodium carbonate), or organic amines (e.g., triethylamine). Preferably, the protecting agent of compounds of Formula 1D or 2D is ethyl chloroformate or BOC anhydride. In an especially preferred embodiment, said protecting agent is ethyl chloroformate and said base is triethylamine.

In another aspect, the invention also provides a method (Method 1E) for preparing compounds of Formula 1E or any of 2.6-2.21:

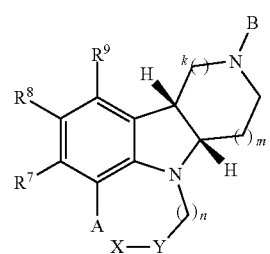

Formula 1E in free or salt form as herein before described, which method comprises the step of N-alkylating compounds of Formula 1D:

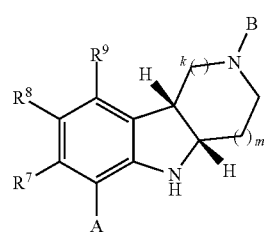

Formula 1D with (a) a nucleophilic alkyl halide of the general formula:

wherein:
(i) A=Cl, F, Br or I;
(ii) X—Y is a —H'OCH$_2$—, —HSCH$_2$—, —H(R')N—CH$_2$— or —H(R')N—C(O)—, wherein R' is H or C$_{1-4}$alkyl;
(iii) n is 1, 2 or 3;
and (b) a base.

In another embodiment, the invention also provides a method (Method 2E) for preparing compounds of Formula 2E or any of 2.27-2.48:

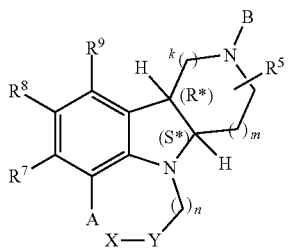

Formula 2E in free or salt form as herein before described, which method comprises the step of N-alkylating compounds of Formula 2D:

Formula 2D with (a) a nucleophilic alkyl halide of the general formula:

wherein:
(i) A=Cl, F, Br or I;
(ii) X—Y is a —H'OCH$_2$—, —HSCH$_2$—, —H(R')N—CH$_2$— or —H(R')N—C(O)—, wherein R' is H or C$_{1-4}$alkyl;
(iii) n is 1, 2 or 3;
and (b) a base.

Examples of nucleophilic alkyl halide for Method 1E or 2E include, but are not limited to, 2-chloroacetamide, 2-bromoacetamide, chloroacetic acid, chloroproprionic acid, 2-chloroethanethioic S-acid. Examples of base useful for Method 1E or 2E include, but not limited to organic bases such as amine bases (e.g., ammonium, triethylamine, N,N'-diisopropylethyl amine or 4-(dimethylamino)pyridine (DMAP); 1,5-diazabicycl[4.3.0]-non-5-ene (DBN), 1,5-diazabicyclo[5.4.0]undec-5-ene (DBU)); or inorganic bases such as hydrides (e.g. sodium, lithium or potassium hydride), alkoxides, (e.g. sodium, potassium or lithium t-butoxide and K(OAr), Na(OAr)), or carbonate, bicarbonate, phosphate or hydroxide of an alkali or alkaline earth metal (e.g. sodium, magnesium, calcium, potassium, cesium or barium carbonate, bicarbonate, hydroxide or phosphate). Optionally, such N-alkylation reaction may be achieved in the presence of an iodide source such as potassium iodide or sodium iodide, preferably potassium iodide. In a preferred embodiment, compounds of Formula 1E or 2E, wherein X—Y— is H(R')N—C(O)— or H(R')N—CH$_2$—, R' is H and n is 1 are prepared by using 2-chloroacetamide in the presence of N,N'-diisopropylethyl amine and potassium iodide. In another preferred embodiment, chloroacetamide, potassium iodide, isopropylethylamine in dixoane solvent is used.

In another aspect, the invention also provides a method (Method 1F) for preparing compounds of Formula 1F:

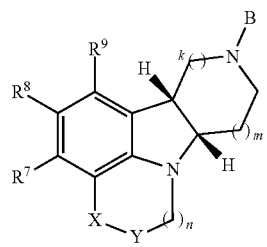

Formula 1F wherein:
(i) k is 1 or 2;
(ii) m is 0, 1 or 2;
(iii) n is 1, 2 or 3;
(iv) B is a protecting agent;
(v) R$^7$, R$^8$ and R$^9$ are independently H or optionally substituted C$_1$-C$_6$ alkyl, alkenyl, alkynyl, cycloalkyl, heterocycloalkyl, hydroxy, alkoxy, nitro, halo, haloalkyl, aryl, arylalkyl, heteroaryl or heteroarylalkyl; and
(vi) X—Y is —OCH$_2$—, —SCH$_2$—, —(R')N—CH$_2$— or -(R')N—C(O)—, wherein R' is H or C$_{1-4}$alkyl;
or any of 2.3-2.21, which method comprises the step of treating compounds of Formula 1E:

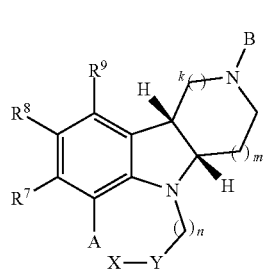

Formula 1E as hereinbefore described, with:
(a) a transition metal catalyst selected from a group consisting of Group 8-11 of the periodic table; and
b) a base.

In another embodiment, the invention provides a method (Method 2F) for preparing compounds of Formula 2F:

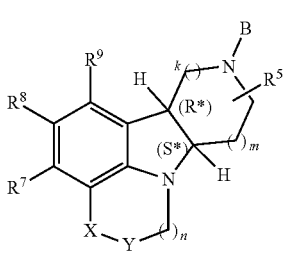

Formula 2F wherein:
(i) k is 1 or 2;
(ii) m is 0, 1 or 2;
(iii) n is 1, 2 or 3;
(iv) B is a protective group;
(v) $R^5$ is H or $C_1$-$C_4$alkyl;
(vi) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, $C_1$-$C_6$alkoxy, nitro, halo, halo$C_1$-$C_6$alkyl, aryl, aryl$C_1$-$C_6$alkyl, heteroaryl or heteroaryl$C_1$-$C_6$alkyl; and
(vii) —X—Y— is —OCH$_2$—, —SCH$_2$—, —(R')N—CH$_2$— or -(R')N—C(O)—, wherein R' is H or $C_{1-4}$alkyl;

or any of 2.25-2.48, which method comprises the step of treating compounds of Formula 2E:

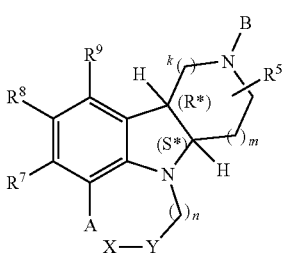

Formula 2E as hereinbefore described with:
(a) a transition metal catalyst selected from a group consisting of Group 8-11 of the periodic table; and
(b) a base.

The transitional metal catalyst of Method 1F or 2F may be an atom, ion, salt or complex of transition metals selected from Groups 8-11 of the periodic table (e.g., palladium, copper, nickel, platinum, ruthenium, or rhodium). Examples of such transition metal catalyst include, but not limited to copper catalysts such as CuI, CuCl, CuBr, CuBr$_2$, Cu(II) acetate, Cu$_2$Cl$_2$, Cu$_2$O, Cu, or palladium or nickel catalysts such as Pd$_2$(dba)$_2$, Pd/C, PdCl$_2$, Pd(OAc)$_2$, (CH$_3$CN)$_2$PdCl$_2$, Pd[P(C$_6$H$_5$)$_3$]$_4$, bis(dibenzylideneacetone) palladium [Pd$_2$(dba)$_3$], Ni(acetylacetonate)$_2$, NiCl$_2$[P(C$_6$H$_5$)]$_2$ and Ni(1,5-cyclooctadiene)$_2$ as described in U.S. Pat. Nos. 6,759,554B2; 6,395,916B1; 6,307,087B1, herein incorporated by reference in their entirety. In a preferred embodiment, the transition metal catalyst is copper catalyst. In an especially preferred embodiment, said catalyst is CuI.

The base useful for Method 1F or 2F may be a bronsted base or a Lewis base well known in the art, including by way of example only, amine bases (e.g. triethylamine, trimethylamine, N,N'-diisopropylethylamine, 1,8-diazabicyclo[5.4.0]undec-7-ene (DBU) or 1,4-diazabicyclo[2.2.2]octane (DABCO)), hydrides (e.g. sodium, lithium or potassium hydride), alkoxides (e.g. sodium or potassium tert-butoxide), carbonates (e.g. sodium carbonate or bicarbonate, potassium or cesium carbonate) or phosphates (e.g. potassium phosphate). In a preferred embodiment, the base is a carbonate of alkali or alkali earth metals (e.g., sodium, potassium, cesium, barium, etc.). In an especially, said base is potassium carbonate.

In yet another embodiment, Method 1F further comprises the step of treating Compound of Formula 1E with a mono or bi-dentate ligand known to ligate with transition metal catalysts. Examples of such ligand include, but are not limited to:
(1) phenolic or amine ligands such as optionally substituted aryl alcohol, 1,2-diamine, 1,2-aminoalcohol, imidazolium carbene, 4-(dimethylamino)pyridine, 2-(aminomethyl)pyridine, 4,7-diphenyl-1,10-phenanthroline, 4,7-dimethyl-1,10-phenanthroline, 5-methyl-1,10-phenanthroline, 5-chloro-1,10-phenanthroline, and 5-nitro-1,10-phenanthroline;
(2) N,N-dimethylformamide, dimethylsulfoxide and 1-methyl-2-pyrrolidinone;
(3) ligand represented by structure 1:

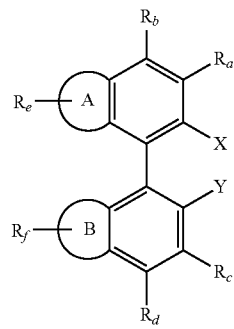

1 wherein
A and B independently represent fused rings selected from the group consisting of monocyclic or polycyclic cycloalkyls, cycloalkenyls, aryls, and heterocyclic rings, said rings having from 4 to 8 atoms in a ring structure;
X represents NR$_2$, P(alkyl)$_2$, P(cycloalkyl)$_2$, AsR$_2$, or OR;
Y represents H, alkyl, NR$_2$, or AsR$_2$;
X and Y are not identical;
R, R$_a$, R$_b$, R$_c$, and R$_d$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —(CH$_2$)$_m$—R$_{80}$;
R$_e$ and R$_f$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

A and B independently are unsubstituted or substituted with $R_e$ and $R_f$, respectively, any number of times up to the limitations imposed by stability and the rules of valence;

$R_a$ and $R_b$, or $R_c$ and $R_d$, or both, taken together optionally represent a ring having a total of 5-7 atoms in the backbone of said ring; said ring having zero, one or two heteroatoms in its backbone; and said ring is substituted or unsubstituted;

$R_{80}$ represents an unsubstituted or substituted aryl, cycloalkyl, cycloalkenyl, heterocycle, or polycycle;

m is an integer in the range 0 to 8 inclusive; and the ligand, when chiral, is a mixture of enantiomers or a single enantiomer;

(4) ligand represented by structure 2:

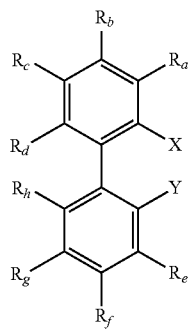

2 wherein

X represents $PR_2$;

Y represents H, $NR_2$, OR, or SR;

R represents, independently for each occurrence, alkyl, heteroalkyl, cycloalkyl, heterocycloalkyl, aryl, heteroaryl, aralkyl, heteroaralkyl, or —$(CH_2)_m$—$R_{80}$;

$R_a$, $R_b$, $R_c$, $R_d$, $R_e$, $R_f$, $R_g$, and $R_h$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

one or more pairs of substituent, with an ortho-relationship therebetween, selected from the group consisting of $R_a$, $R_b$, $R_c$, $R_d$, $R_e$, $R_f$, $R_g$, and $R_h$, taken together optionally represent a ring having a total of 5-7 atoms in the backbone of said ring; said ring having zero, one or two heteroatoms in its backbone; and said ring is substituted or unsubstituted;

$R_{80}$ represents an unsubstituted or substituted aryl, cycloalkyl, cycloalkenyl, heterocycle, or polycycle;

m is an integer in the range 0 to 8 inclusive; and the ligand, when chiral, is a mixture of enantiomers or a single enantiomer;

(5) ligand represented by structure 3:

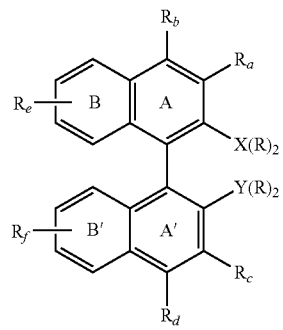

3 wherein

X represents $NR_2$, $P(alkyl)_2$, $P(cycloalkyl)_2$, $AsR_2$, or OR;

Y represents H, alkyl, $NR_2$, $AsR_2$, or OR;

X and Y are not identical;

R, $R_a$, $R_b$, $R_c$, and $R_d$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

$R_e$ and $R_f$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

the B and B' rings of the binaphthyl core independently are unsubstituted or substituted with $R_e$ and $R_f$, respectively, any number of times up to the limitations imposed by stability and the rules of valence;

$R_a$ and $R_b$, or $R_c$ and $R_d$, or both, taken together optionally represent a ring consisting of a total of 5-7 atoms in the backbone of said ring; said ring having zero, one or two heteroatoms in its backbone; and said ring is substituted or unsubstituted;

$R_{80}$ represents an unsubstituted or substituted aryl, cycloalkyl, cycloalkenyl, heterocycle, or polycycle;

m is an integer in the range 0 to 8 inclusive; and the ligand, when chiral, is a mixture of enantiomers or a single enantiomer;

(6) ligand represented by structure 4:

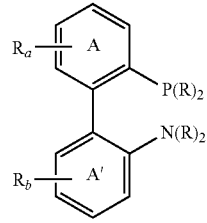

4 wherein:
R is selected, independently for each occurrence, from the group consisting of alkyl, heteroalkyl, cycloalkyl, heterocycloalkyl, aryl, heteroaryl, aralkyl, heteroaralkyl, and —$(CH_2)_m$—$R_{80}$;
the A and A' rings of the biphenyl core independently are unsubstituted or substituted with $R_1$ and $R_2$, respectively, any number of times up to the limitations imposed by stability and the rules of valence;
$R_a$ and $R_b$ are selected, independently for each occurrence, from the group consisting of alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$;
$R_{80}$ represents an unsubstituted or substituted aryl, cycloalkyl, cycloalkenyl, heterocycle, or polycycle;
m is an integer in the range 0 to 8 inclusive; and
the ligand, when chiral, is a mixture of enantiomers or a single enantiomer;

(7) ligand represented by structure 5:

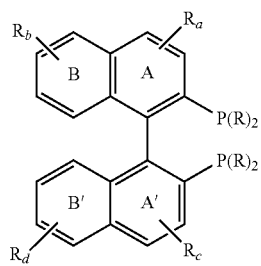

5

R is selected, independently for each occurrence, from the group consisting of alkyl, heteroalkyl, cycloalkyl, heterocycloalkyl, aryl, heteroaryl, aralkyl, heteroaralkyl, and —$(CH_2)_m$—$R_{80}$;
the A, B, A', and B' rings of the binaphthyl core independently are unsubstituted or substituted with $R_a$, $R_b$, $R_c$, and $R_d$, respectively, any number of times up to the limitations imposed by stability and the rules of valence;
$R_a$, $R_b$, $R_c$, and $R_d$, are selected, independently for each occurrence, from the group consisting of alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$;
$R_{80}$ represents an unsubstituted or substituted aryl, cycloalkyl, cycloalkenyl, heterocycle, or polycycle;
m is an integer in the range 0 to 8 inclusive; and
the ligand, when chiral, is a mixture of enantiomers or a single enantiomer;

provided that when R is cycloalkyl or aryl, there is at least one instance of $R_a$, $R_b$, $R_c$, or $R_d$;

(8) ligand represented by structure 6:

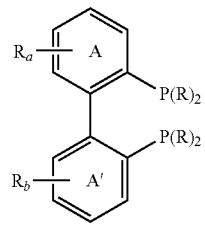

6

R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$;
the A and A' rings of the biphenyl core independently may be unsubstituted or substituted with $R_a$ and $R_b$, respectively, any number of times up to the limitations imposed by stability and the rules of valence;
$R_a$ and $R_b$ are selected, independently for each occurrence, from the set comprising alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$;
$R_{80}$ represents an unsubstituted or substituted aryl, a cycloalkyl, a cycloalkenyl, a heterocycle, or a polycycle;
m is an integer in the range 0 to 8 inclusive; and
the ligand, when chiral, may be provided in the form of a mixture of enantiomers or as a single enantiomer; and (9) ligand represented by structure 7:

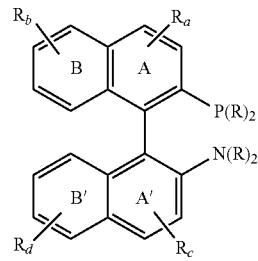

7 wherein
R is selected, independently for each occurrence, from the group consisting of alkyl, heteroalkyl, cycloalkyl, heterocycloalkyl, aryl, heteroaryl, aralkyl, heteroaralkyl, and —$(CH_2)_m$—$R_{80}$;
$P(R)_2$ represents $P(alkyl)_2$, or $P(cycloalkyl)_2$;
the A, B, A', and B' rings of the binaphthyl core independently are unsubstituted or substituted with $R_a$, $R_b$, $R_c$, and $R_d$, respectively, any number of times up to the limitations imposed by stability and the rules of valence;
$R_a$, $R_b$, $R_c$, and $R_d$, are selected, independently for each occurrence, from the group consisting of alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$;
$R_{80}$ represents an unsubstituted or substituted aryl, cycloalkyl, cycloalkenyl, heterocycle, or polycycle;

m is an integer in the range 0 to 8 inclusive; and
the ligand, when chiral, is a mixture of enantiomers or a single enantiomer.

Examples of phenolic or amine ligands include, but are not limited to 2-phenylphenol, 2,6-dimethylphenol, 2-isopropylphenol, 1-naphthol, 8-hydroxyquinoline, 8-aminoquinoline, DBU, 2-(dimethylamino)ethanol, N,N-diethylsalicylamide, 2-(dimethylamino)glycine, N,N,N',N'-tetramethyl-1,2-diaminoethane, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, (methylimino)diacetic acid, cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, N,N'-dimethyl-1,2-diaminoethane, N,N-dimethyl-2-hydroxybenzamide, N,N-diethyl-2-hydroxybenzamide, fluoro-N,N-diethyl-2-hydroxybenzamide, chloro-N,N'-diethyl-2-hydroxybenzamide, (2-hydroxyphenyl)(pyrrolidin-1-yl) methanone, biphenyl-2-ol, 2-pyridylphenol, 1,2-benezenediamine, ammonia, N,N-dimethylformamide, dimethylsulfoxide and 1-methyl-2-pyrrolidinone as described in U.S. Pat. Nos. 6,759,554B2; 6,395,916B1; 6,307,087B1, Klapars, A. et al., *J. Am. Chem. Soc.* (2002) 124, 7421-7428; Kang, S., et al., *Synlett,* 3, 427-430 (2002); Sugahara, M. and Ukita, T., *Chem. Pharm. Bull.* (1997) 45, 719-721, herein incorporated by reference.

In still another embodiment, Method 2F further comprises the step of treating Compound of Formula 2E with a mono or bi-dentate ligand known to ligate with transition metal catalysts. Examples of such ligand include, but are not limited to ligands disclosed above in Method 1F. In a preferred embodiment, the ligand of Method 1F or 2F is optionally substituted 1,2-diamine ligands. In an especially preferred embodiment, said ligand is N,N'-dimethyl-1,2-diaminoethyane, trans-N,N'-dimethyl-1,2-diaminocyclohexane, N-butylethylenediamine. In a most preferred embodiment, said ligand is N,N'-dimethyl-1,2-diaminoethane. Without being bound to any theory, it is believed that the ligands facilitate the reaction by stabilizing and solubilizing the metal catalyst.

In another embodiment, the invention also provides a method (Method 1E') for preparing compounds of Formula 1E' or any of 2.8-2.21:

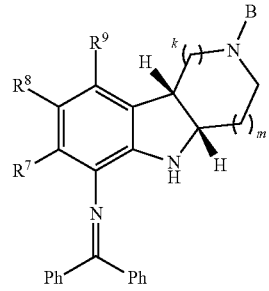

Formula 1E' as hereinbefore described, which method comprises the step of treating compounds of Formula 1D with (a) benzophenone imine; (b) a transition metal catalyst selected from Groups 8-11 of the Periodic Table; (c) a base; and (d) ligands selected from a group consisting of:

(1) phenolic or amine ligands such as optionally substituted aryl alcohol, 1,2-diamine, 1,2-aminoalcohol, imidazolium carbene, 4-(dimethylamino)pyridine, 2-(aminomethyl)pyridine, 4,7-diphenyl-1,10-phenanthroline, 4,7-dimethyl-1,10-phenanthroline, 5-methyl-1,10-phenanthroline, 5-chloro-1,10-phenanthroline, and 5-nitro-1,10-phenanthroline;

(2) ligand represented by structure 1:

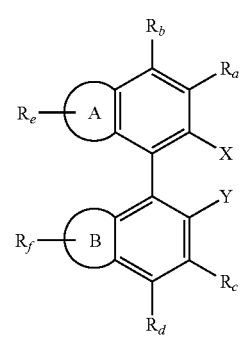

1 wherein
A and B independently represent fused rings selected from the group consisting of monocyclic or polycyclic cycloalkyls, cycloalkenyls, aryls, and heterocyclic rings, said rings having from 4 to 8 atoms in a ring structure;

X represents $NR_2$, $P(alkyl)_2$, $P(cycloalkyl)_2$, $AsR_2$, or $OR$;

Y represents H, alkyl, $NR_2$, or $AsR_2$;

X and Y are not identical;

R, $R_a$, $R_b$, $R_c$, and $R_d$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $-(CH_2)_m-R_{80}$;

$R_e$ and $R_f$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $-(CH_2)_m-R_{80}$;

A and B independently are unsubstituted or substituted with $R_e$ and $R_f$, respectively, any number of times up to the limitations imposed by stability and the rules of valence;

$R_a$ and $R_b$, or $R_c$ and $R_d$, or both, taken together optionally represent a ring having a total of 5-7 atoms in the backbone of said ring; said ring having zero, one or two heteroatoms in its backbone; and said ring is substituted or unsubstituted;

$R_{80}$ represents an unsubstituted or substituted aryl, cycloalkyl, cycloalkenyl, heterocycle, or polycycle;

m is an integer in the range 0 to 8 inclusive; and the ligand, when chiral, is a mixture of enantiomers or a single enantiomer;

(3) ligand represented by structure 2:

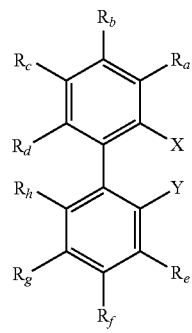

2 wherein

X represents $PR_2$;

Y represents H, $NR_2$, OR, or SR;

R represents, independently for each occurrence, alkyl, heteroalkyl, cycloalkyl, heterocycloalkyl, aryl, heteroaryl, aralkyl, heteroaralkyl, or $-(CH_2)_m-R_{80}$;

$R_a$, $R_b$, $R_c$, $R_d$, $R_e$, $R_f$, $R_g$, and $R_h$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $-(CH_2)_m-R_{80}$;

one or more pairs of substituent, with an ortho-relationship therebetween, selected from the group consisting of $R_a$, $R_b$, $R_c$, $R_d$, $R_e$, $R_f$, $R_g$, and $R_h$, taken together optionally represent a ring having a total of 5-7 atoms in the backbone of said ring; said ring having zero, one or two heteroatoms in its backbone; and said ring is substituted or unsubstituted;

$R_{80}$ represents an unsubstituted or substituted aryl, cycloalkyl, cycloalkenyl, heterocycle, or polycycle;

m is an integer in the range 0 to 8 inclusive; and the ligand, when chiral, is a mixture of enantiomers or a single enantiomer;

(4) ligand represented by structure 3:

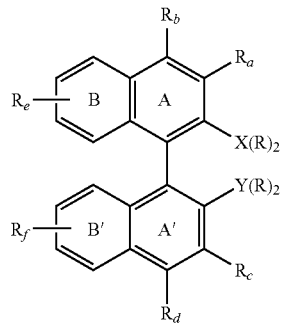

3 wherein

X represents $NR_2$, $P(alkyl)_2$, $P(cycloalkyl)_2$, $AsR_2$, or OR;

Y represents H, alkyl, $NR_2$, $AsR_2$, or OR;

X and Y are not identical;

R, $R_a$, $R_b$, $R_c$ and $R_d$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $-(CH_2)_m-R_{80}$;

$R_e$ and $R_f$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $-(CH_2)_m-R_{80}$;

the B and B' rings of the binaphthyl core independently are unsubstituted or substituted with $R_e$ and $R_f$, respectively, any number of times up to the limitations imposed by stability and the rules of valence;

$R_a$ and $R_b$, or $R_c$ and $R_d$, or both, taken together optionally represent a ring consisting of a total of 5-7 atoms in the backbone of said ring; said ring having zero, one or two heteroatoms in its backbone; and said ring is substituted or unsubstituted;

$R_{80}$ represents an unsubstituted or substituted aryl, cycloalkyl, cycloalkenyl, heterocycle, or polycycle;

m is an integer in the range 0 to 8 inclusive; and the ligand, when chiral, is a mixture of enantiomers or a single enantiomer;

(5) ligand represented by structure 4:

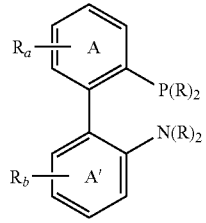

4 wherein:
R is selected, independently for each occurrence, from the group consisting of alkyl, heteroalkyl, cycloalkyl, heterocycloalkyl, aryl, heteroaryl, aralkyl, heteroaralkyl, and —(CH$_2$)$_m$—R$_{80}$;
the A and A' rings of the biphenyl core independently are unsubstituted or substituted with R$_1$ and R$_2$, respectively, any number of times up to the limitations imposed by stability and the rules of valence;
R$_a$ and R$_b$ are selected, independently for each occurrence, from the group consisting of alkyl, heteroalkyl, cycloalkyl, heterocycloalkyl, aryl, heteroaryl, aralkyl, heteroaralkyl, halogen, —SiR$_3$, and —(CH$_2$)$_m$—R$_{80}$;
R$_{80}$ represents an unsubstituted or substituted aryl, cycloalkyl, cycloalkenyl, heterocycle, or polycycle;
m is an integer in the range 0 to 8 inclusive; and
the ligand, when chiral, is a mixture of enantiomers or a single enantiomer;

(6) ligand represented by structure 5:

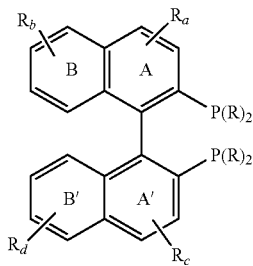

5

R is selected, independently for each occurrence, from the group consisting of alkyl, heteroalkyl, cycloalkyl, heterocycloalkyl, aryl, heteroaryl, aralkyl, heteroaralkyl, and —(CH$_2$)$_m$—R$_{80}$;
the A, B, A', and B' rings of the binaphthyl core independently are unsubstituted or substituted with R$_a$, R$_b$, R$_c$, and R$_d$, respectively, any number of times up to the limitations imposed by stability and the rules of valence;
R$_a$, R$_b$, R$_c$, and R$_d$, are selected, independently for each occurrence, from the group consisting of alkyl, heteroalkyl, cycloalkyl, heterocycloalkyl, aryl, heteroaryl, aralkyl, heteroaralkyl, halogen, —SiR$_3$, and —(CH$_2$)$_m$—R$_{80}$;
R$_{80}$ represents an unsubstituted or substituted aryl, cycloalkyl, cycloalkenyl, heterocycle, or polycycle;
m is an integer in the range 0 to 8 inclusive; and
the ligand, when chiral, is a mixture of enantiomers or a single enantiomer;

provided that when R is cycloalkyl or aryl, there is at least one instance of R$_a$, R$_b$, R$_c$, or R$_d$;

(7) ligand represented by structure 6:

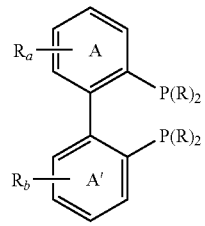

6

R is selected, independently for each occurrence, from the set comprising alkyl, heteroalkyl, cycloalkyl, heterocycloalkyl, aryl, heteroaryl, aralkyl, heteroaralkyl, and —(CH$_2$)$_m$—R$_{80}$;
the A and A' rings of the biphenyl core independently may be unsubstituted or substituted with R$_a$ and R$_b$, respectively, any number of times up to the limitations imposed by stability and the rules of valence;
R$_a$ and R$_b$ are selected, independently for each occurrence, from the set comprising alkyl, heteroalkyl, cycloalkyl, heterocycloalkyl, aryl, heteroaryl, aralkyl, heteroaralkyl, halogen, —SiR$_3$, and —(CH$_2$)$_m$—R$_{80}$;
R$_{80}$ represents an unsubstituted or substituted aryl, a cycloalkyl, a cycloalkenyl, a heterocycle, or a polycycle;
m is an integer in the range 0 to 8 inclusive; and
the ligand, when chiral, may be provided in the form of a mixture of enantiomers or as a single enantiomer;

(8) ligand represented by structure 7:

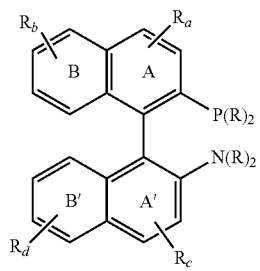

7 wherein
R is selected, independently for each occurrence, from the group consisting of alkyl, heteroalkyl, cycloalkyl, heterocycloalkyl, aryl, heteroaryl, aralkyl, heteroaralkyl, and —(CH$_2$)$_m$—R$_{80}$;
P(R)$_2$ represents P(alkyl)$_2$, or P(cycloalkyl)$_2$;
the A, B, A', and B' rings of the binaphthyl core independently are unsubstituted or substituted with R$_a$, R$_b$, R$_c$, and R$_d$, respectively, any number of times up to the limitations imposed by stability and the rules of valence;
R$_a$, R$_b$, R$_c$, and R$_d$, are selected, independently for each occurrence, from the group consisting of alkyl, heteroalkyl, cycloalkyl, heterocycloalkyl, aryl, heteroaryl, aralkyl, heteroaralkyl, halogen, —SiR$_3$, and —(CH$_2$)$_m$—R$_{80}$;
R$_{80}$ represents an unsubstituted or substituted aryl, cycloalkyl, cycloalkenyl, heterocycle, or polycycle;

m is an integer in the range 0 to 8 inclusive; and the ligand, when chiral, is a mixture of enantiomers or a single enantiomer; and (9) 2,2'-bis(diphenylphosphino)-1,1'-binaphthyl.

In another embodiment, the invention also provides a method (Method 2E') for preparing compounds of Formula 2E' or any of 2.31-2.48:

Formula 2E'

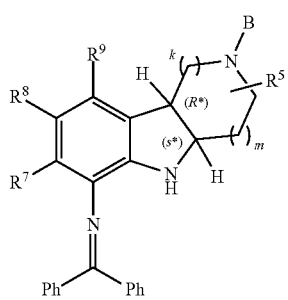

as hereinbefore described, which method comprises the step of treating compounds of Formula 2D with (a) benzophenone imine; (b) a transition metal catalyst selected from Groups 8-11 of the Periodic Table; (c) a base; and (d) a ligand selected from a group consisting of ligands as described above in Method 1E.

Useful transition metal catalysts of Method 1E' and 2E' include atoms, ions, salts or complexes of transition metals selected from Groups 8-11 of the periodic table (e.g., palladium, copper, nickel, platinum, ruthenium, or rhodium). Examples of such transition metal catalyst include, but not limited to copper catalysts (e.g., CuI, CuCl, CuBr, $CuBr_2$, Cu(II) acetate, $Cu_2Cl_2$, $Cu_2O$, Cu). Other examples of useful transition metal catalysts include complexes of palladium or nickel including, but not limited to $Pd_2(dba)_2$, Pd/C, $PdCl_2$, $Pd(OAc)_2$, $(CH_3CN)_2PdCl_2$, $Pd[P(C_6H_5)_3]_4$, bis(dibenzylideneacetone) palladium $[Pd_2(dba)_2]$, Ni(acetylacetonate)$_2$, $NiCl_2[P(C_6H_5)]_2$ and Ni(1,5-cyclooctadiene)$_2$ as described in U.S. Pat. Nos. 6,759,554B2; 6,395,916B1; 6,307,087B1, herein incorporated by reference.

Examples of a useful base for Method 1E' or 2E' include, for example, amine bases (e.g., triethyl amine, N,N'-diisopropylethyl amine or 4-(dimethylamino)pyridine (DMAP); 1,5-diazabicycl[4.3.0]non-5-ene (DBN), 1,5-diazabicyclo[5.4.0]undec-5-ene (DBU)) and 1,4-Diazabicyclo[2.2.2]octane (DABCO); inorganic bases such as hydrides (e.g. sodium, lithium and potassium hydride), alkoxides, (e.g. sodium, potassium or lithium t-butoxide, K(OAr) or Na(OAr)), or carbonate, bicarbonate, phosphate or hydroxide of alkali or alkaline earth metals (e.g. sodium, magnesium, calcium, potassium, cesium, barium carbonate, bicarbonate, hydroxide and phosphate) and potassium hexamethyldisilazane. In a particularly preferred embodiment, Method 1E' comprises the step of treating Compound 1D with (1) benzophenone imine; (2) $Pd_2(dba)_2$; (3) sodium tert-butoxide; and (4) 2,2'-bis(diphenylphosphino)-1,1'-binaphthyl.

In another aspect, the invention also provides a method (Method 1F'') for preparing compounds of Formula 1F'' or any of 2.3-2.21:

Formula 1F''

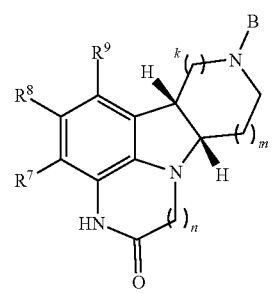

as hereinbefore described, which method comprises the step of treating compounds of Formula 1E':

Formula 1E'

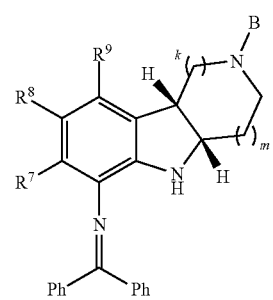

in free or salt form as hereinbefore described with (1) alkyl haloacetate having a general formula of:

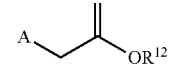

wherein:
(i) A is Cl, Br or I; and
(ii) $R^{12}$ is $C_{1-4}$alkyl;
(2) a base.

In yet another embodiment of Method 1E', sodium or potassium iodide is present when the compound of Formula 1E' is treated with the alkyl haloacetate. In an especially preferred embodiment, Method 1E' comprises the step of treating Compound of Formula 1D with (1) ethyl bromoacetate; (2) sodium carbonate; and (3) potassium iodide.

In still another embodiment, the invention provides a method (Method 2F'') for preparing compounds of Formula 2F'' or any of 2.25-2.48:

Formula 2F''

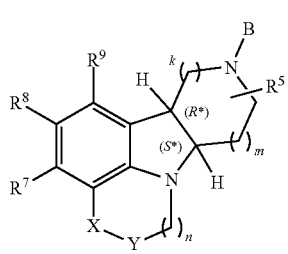

as hereinbefore described, which method comprises the step of treating compounds of Formula 2E':

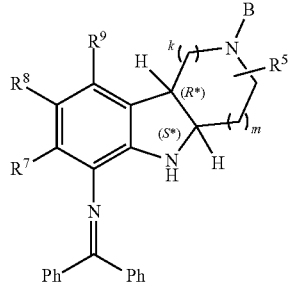

Formula 2E' in free or salt form as hereinbefore described with (1) alkyl haloacetate having a general formula of:

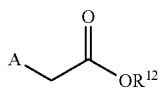

wherein:
(i) A is Cl, Br or I; and
(ii) $R^{12}$ is $C_{1-4}$alkyl;
(2) a base.

In still another embodiment of Method 2E', sodium or potassium iodide is present when the compound of Formula 2E' is treated with the alkyl haloacetate.

In another aspect, the invention also provides a method (Method 1G) for preparing compounds of Formula 1G:

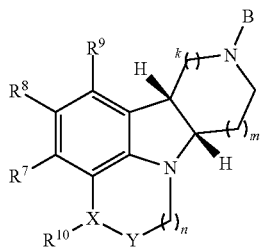

Formula 1G wherein:
(i) k is 1 or 2;
(ii) m is 0, 1 or 2;
(iii) n is 1, 2 or 3;
(iv) B is a protective group;
(v) $R^7$, $R^8$ and $R^9$ are independently H or optionally substituted $C_1$-$C_6$ alkyl, alkenyl, alkynyl, cycloalkyl, heterocycloalkyl, hydroxy, alkoxy, nitro, halo, haloalkyl, aryl, arylalkyl, heteroaryl or heteroarylalkyl;
(vi) X—Y is a

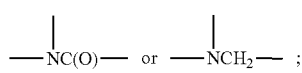

and
(vii) $R^{10}$ is $C_{1-4}$alkyl, alkenyl or alkynyl; or any of 2.1-2.21, in free or salt form, which method comprises the step of N-alkylating compounds of Formula 1F':

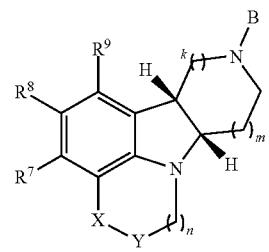

Formula 1F' wherein:
(i) k is 1 or 2;
(ii) m is 0, 1 or 2;
(iii) n is 1, 2 or 3;
(iv) B is a protecting agent;
(v) $R^7$, $R^8$ and $R^9$ are independently H or optionally substituted $C_1$-$C_6$ alkyl, alkenyl, alkynyl, cycloalkyl, heterocycloalkyl, hydroxy, alkoxy, nitro, halo, haloalkyl, aryl, arylalkyl, heteroaryl or heteroarylalkyl; and
(vi) X—Y is —(R')N—$CH_2$— or —(R')N—C(O)—, wherein R' is H.

In another aspect, the invention also provides a method (Method 2G) for preparing compounds of Formula 2G':

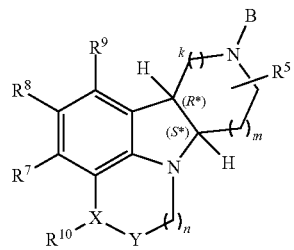

Formula 2G' wherein:
(i) k is 1 or 2;
(ii) m is 0, 1 or 2;
(iii) n is 1, 2 or 3;
(iv) B is a protective group;
(v) $R^5$ is H or $C_1$-$C_4$alkyl;
(vi) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, $C_1$-$C_6$alkoxy, nitro, halo, halo$C_1$-$C_6$alkyl, aryl, aryl$C_1$-$C_6$alkyl, heteroaryl or heteroaryl$C_1$-$C_6$alkyl;
(vii) X—Y is a

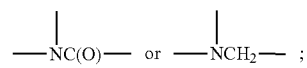

and
(viii) $R^{10}$ is $C_{1-4}$alkyl;
or any of 2.22-2.48, in free or salt form, which method comprises the step of N-alkylating compounds of Formula 2F':

Formula 2F'

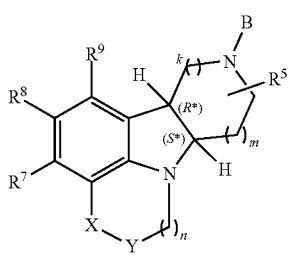

wherein:
(i) k is 1 or 2;
(ii) m is 0, 1 or 2;
(iii) n is 1, 2 or 3;
(iv) B is a protective group;
(viii) $R^5$ is H or $C_1$-$C_4$alkyl;
(v) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, $C_1$-$C_6$alkoxy, nitro, halo, halo$C_1$-$C_6$alkyl, aryl, aryl$C_1$-$C_6$alkyl, heteroaryl or heteroaryl$C_1$-$C_6$alkyl; and
(vi) —X—Y— is —(R')N—CH$_2$— or —(R')N—C(O)—, wherein R' is H.

N-alkylation of Method 1G or 2G may be achieved by treating compounds of Formula 2F' with an optionally substituted alkyl halide (e.g., methyl iodide, iodoethane) in the presence of a base (e.g., potassium carbonate).

In another aspect, the invention provides a method (Method 3G') for preparing compounds of Formula 2G which method comprises the step of treating a compound of Formula 2E" (wherein X—Y is HN(R')CH2 or HN(R')—C(O)—) with (i) a transition metal catalyst; (ii) a base and (iii) optionally a mono or bidentate ligand as disclosed in Method 2F".

In still another embodiment, the invention also provides Method 3G for preparing compounds of Formula 2G as hereinbefore described which method comprises the steps of:
a) treating a Compound of Formula 2D in free or salt form as hereinbefore described with (i) a nucleophilic alkyl halide of the general formula:

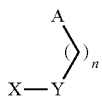

as hereinbefore described, (ii) a base and (iii) potassium iodide in a solvent such as dioxane; and
b) adding (i) a transition metal catalyst selected from a group consisting of Group 8-11 of the periodic table; (ii) a base; and (iii) optionally a mono or bi-dentate ligand known to ligate with transition metal catalysts.

The nucleophilic alkyl halide, base and potassium of step (a) of Method 3G may be those described above in Methods 1E and 2E. In a preferred embodiment, the nucleophilic alkyl halide is chloroacetamide or N-methyl chloroacetamide and the base is isopropylethylamine. Examples of the transition metal catalyst of step (b) of Method 3G may be those described in Methods 1F and 2F (e.g., copper catalysts such as CuI, CuCl, CuBr, CuBr$_2$, Cu(II) acetate, Cu$_2$Cl$_2$, Cu$_2$O, Cu, or palladium or nickel catalysts such as Pd$_2$(dba)$_2$, Pd/C, PdCl$_2$, Pd(OAc)$_2$, (CH$_3$CN)$_2$PdCl$_2$, Pd[P(C$_6$H$_5$)$_3$]$_4$, bis(dibenzylideneacetone) palladium [Pd$_2$(dba)$_3$], Ni(acetylacetonate)$_2$, NiCl$_2$[P(C$_6$H$_5$)$_3$]$_2$ and Ni(1,5-cyclooctadiene)$_2$). In a particular embodiment, the catalyst is CuI. Examples of mono or bi-dentate ligand known to ligate with transition metal catalysts of Method 3G include those described above in methods 1F and 2F.

In another aspect, the invention also provides a method (Method 1H) for preparing compounds of Formula 1H:

Formula 1H

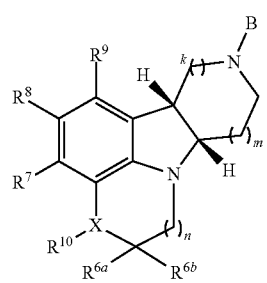

wherein:
(i) k is 1 or 2;
(ii) m is 0, 1 or 2;
(iii) n is 1, 2 or 3;
(iv) B is a protective group;
(v) $R^7$, $R^8$ and $R^9$ are independently H or optionally substituted $C_1$-$C_6$ alkyl, alkenyl, alkynyl, cycloalkyl, heterocycloalkyl, hydroxy, alkoxy, nitro, halo, haloalkyl, aryl, arylalkyl, heteroaryl or heteroarylalkyl;
(vi) X is a N; and
(vii) $R^{10}$ is H or $C_{1-4}$alkyl; and
(viii) $R^{6a}$ and $R^{6b}$ are independently selected from a group consisting of H; which method comprises the step of reducing the ketone of compounds of Formula 1G:

Formula 1G

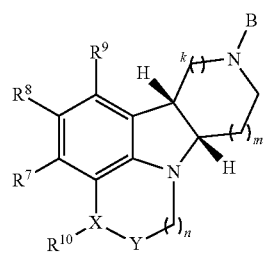

wherein:
(i) k is 1 or 2;
(ii) m is 0, 1 or 2;
(iii) n is 1, 2 or 3;
(iv) B is a protective group;
(v) $R^7$, $R^8$ and $R^9$ are independently H or optionally substituted $C_1$-$C_6$ alkyl, alkenyl, alkynyl, cycloalkyl, heterocycloalkyl, hydroxy, alkoxy, nitro, halo, haloalkyl, aryl, arylalkyl, heteroaryl or heteroarylalkyl.
(vi) X—Y is a

and (vii) $R^{10}$ is $C_{1-4}$alkyl, alkenyl or alkynyl; to a methylene. Such reduction may be accomplished through the use of a reducing agent selected from a group consisting of metal hydrides (e.g., diisobutyl aluminum hydride (DIBAL), sodium bis(2-methoxyethoxy)aluminum hydride (Red-Al) or sodium cyanoborohydride); boranes (e.g., $BH_3$-THF); or organoboranes (e.g. bis (benzyloxy)borane). Alternatively, such conversion may also be accomplished through catalytic hydrogenation by using hydrogen in presence of a catalyst (e.g. palladium on carbon, palladium oxide, etc.); Wolff-Kishner reduction by heating the ketone with hydrazine hydrate in the presence of a base such as sodium or potassium hydroxide (See Todd, *Org. React.* 4, 378-422 (1948)); or Clemmensen reduction by heating the ketone with zinc amalgam and aqueous mineral acid such as hydrochloric acid (See Vedejs, *Org. React.* 22, 401-422 (1975)). Other reagents that may also accomplish such reduction include triisopropyl phosphate, copper in the presence of sulfuric acid and tin in the presence of hydrochloric acid.

In another aspect, the invention also provides a method (Method 2H) for preparing compounds of Formula 2H:

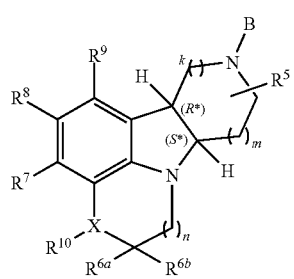

Formula 2H wherein:

(i) k is 1 or 2;

(ii) m is 0, 1 or 2;

(iii) n is 1, 2 or 3;

(iv) B is a protective group;

(v) $R^5$ is H or $C_1$-$C_4$alkyl;

(vi) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, $C_1$-$C_6$alkoxy, nitro, halo, halo$C_1$-$C_6$alkyl, aryl, aryl$C_1$-$C_6$alkyl, heteroaryl or heteroaryl$C_1$-$C_6$alkyl;

(vii) X is a N; and (viii) $R^{10}$ is H or $C_{1-4}$alkyl; and (ix) $R^{6a}$ and $R^{6b}$ are independently selected from a group consisting of H; which method comprises the step of reducing the ketone of compounds of Formula 2G':

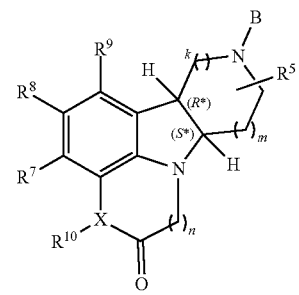

Formula 2G' in free or salt form as hereinbefore described to a methylene. Such reduction may be accomplished through the use of a reducing agent selected from a group as described above in Method 1H. In another embodiment, the reduction of the ketone comprises the use of 9-Borabicyclo[3.3.1]nonane (9-BBN).

In another aspect, the invention also provides a method (Method 1I) for preparing compounds of Formula 1I:

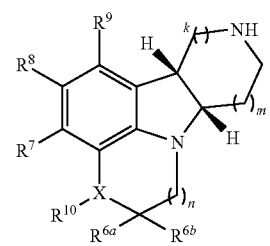

Formula 1I wherein:

(i) k is 1 or 2;

(ii) m is 0, 1 or 2;

(iii) n is 1, 2 or 3;

(iv) $R^7$, $R^8$ and $R^9$ are independently H or optionally substituted $C_1$-$C_6$ alkyl, alkenyl, alkynyl, cycloalkyl, heterocycloalkyl, hydroxy, alkoxy, nitro, halo, haloalkyl, aryl, arylalkyl, heteroaryl or heteroarylalkyl;

(v) X is a N, S or O;

(vi) $R^{10}$ is H or $C_{1-4}$alkyl when X is N or $R^{10}$ is nonexistent when X is O or S; and (vii) $R^{6a}$ and $R^{6b}$ are H;

which method comprises the step of deprotecting compounds of Formula 1H:

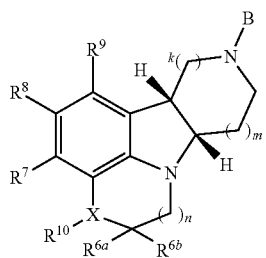

Formula 1H wherein:

(i) k is 1 or 2;

(ii) m is 0, 1 or 2;

(iii) n is 1, 2 or 3;

(iv) B is a protecting agent;
(v) $R^7$, $R^8$ and $R^9$ are independently H or optionally substituted $C_1$-$C_6$ alkyl, alkenyl, alkynyl, cycloalkyl, heterocycloalkyl, hydroxy, alkoxy, nitro, halo, haloalkyl, aryl, arylalkyl, heteroaryl or heteroarylalkyl;
(vi) X is a N, O or S; and
(vii) $R^{10}$ is H or $C_{1-4}$alkyl when X is N or $R^{10}$ is non-existent when X is O or S; and
(viii) $R^{6a}$ and $R^{6b}$ are H.

In another embodiment, the invention provides a method (Method 2I) for preparing compounds of Formula 2I:

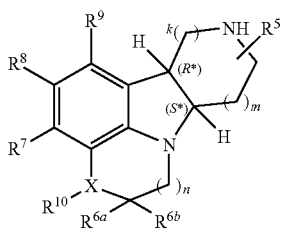

Formula 2I wherein:
(i) k is 1 or 2;
(ii) m is 0, 1 or 2;
(iii) n is 1, 2 or 3;
(iv) $R^5$ is H or $C_1$-$C_4$alkyl;
(v) $R^7$, $R^8$ and $R^9$ are independently H or optionally substituted $C_1$-$C_6$alkyl, $C_3$-$C_{10}$cycloalkyl, $C_3$-$C_{10}$heterocycloalkyl, hydroxy, $C_{1-6}$alkoxy, nitro, halo, halo$C_1$-$C_6$alkyl, aryl, aryl$C_1$-$C_6$alkyl, heteroaryl or heteroaryl$C_1$-$C_6$alkyl;
(vi) X is a N, S or O;
(vii) $R^{10}$ is H or $C_{1-4}$alkyl when X is N or $R^{10}$ is non-existent when X is O or S; and
(viii) $R^{6a}$ and $R^{6b}$ are H;
which method comprises the step of deprotecting compounds of Formula 2H:

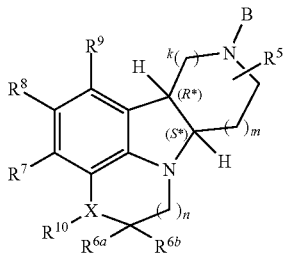

Formula 2H as herein before described.

The deprotection conditions for the protective groups of Method 1I or 2I necessarily vary with the choice of protecting group and may involve acid or base catalysis or catalytic hydrogenation. Thus, for example, wherein the protecting agent is an acyl group such as an alkanoyl or alkoxycarbonyl group (e.g., ethoxycarbonyl) or an aroyl group, deprotection may be accomplished for example, by hydrolysis with a base such as an alkali metal hydroxide, for example lithium, potassium or sodium hydroxide. Alternatively, an acyl protecting agent such as a t-butoxycarbonyl group may be removed, for example, by treatment with a suitable acid as hydrochloric, sulfuric or phosphoric acid or trifluoroacetic acid. An arylmethoxycarbonyl protecting agent such as a benzyloxycarbonyl group may be removed, for example, by hydrogenation over acatalyst such as palladium-on-carbon, or by treatment with a Lewis acid such as boron tris (trifluoroacetate). For further examples of reagents useful for said deprotection step, see "Protective Groups in Organic Synthesis" by Theodora Green (publisher: John Wiley & Sons).

In another aspect, the invention also provides a method (Method 1J) for preparing compounds of Formula 1J:

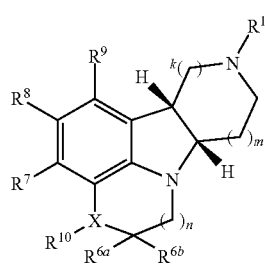

Formula 1J wherein:
(i) k is 1 or 2;
(ii) m is 0, 1 or 2;
(iii) n is 1, 2 or 3;
(iv) X is N, S or O;
(v) $R^7$, $R^8$ and $R^9$ are independently H or optionally substituted $C_1$-$C_6$ alkyl, alkenyl, alkynyl, cycloalkyl, heterocycloalkyl, hydroxy, alkoxy, nitro, halo, haloalkyl, aryl, arylalkyl, heteroaryl or heteroarylalkyl;
(vi) $R^{10}$ is H or $C_{1-4}$alkyl when X is N or $R^{10}$ is non-existent when X is O or S;
(vii) $R^{6a}$ and $R^{6b}$ are H; and
(viii) $R^1$ is H or optionally substituted $C_1$-$C_6$alkyl, cycloalkyl, aryl, arylalkyl (e.g., benzyl), heteroaryl, heteroarylalkyl, aryloxoalkyl (e.g., 4-(4-fluorophenyl)-4-oxobutyl)), aryloxyalkyl (e.g., 3-(4-fluorophenoxy)propyl)), heroaryloxoalkyl, heroaryloxyalkyl, aryl sulfinylalkyl or heteroaryl sulfinylalkyl;

which method comprises the step of N-alkylating compounds of Formula 1I:

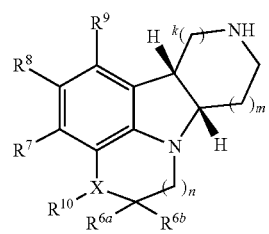

Formula 1I as hereinbefore described, with (a) a compound of the general formula:

$$G—Z^{R^{13}}$$

wherein:
 (i) Z is —C(O)—, —O—, or S(O)$_2$—;
 (ii) R$^{13}$ is optionally substituted aryl, arylalkyl, alkyl, heteroaryl, heteroarylalkyl; and
 (iii) G is C$_1$-C$_8$alkyl halide (e.g., propyl chloride);
and (b) a base.

In another embodiment, the invention also provides a method (Method 2J) for preparing compounds of Formula 2J:

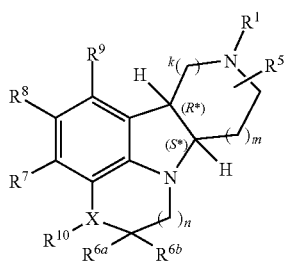

Formula 2J wherein:
 (i) k is 1 or 2;
 (ii) m is 0, 1 or 2;
 (iii) n is 1, 2 or 3;
 (iv) X is N, S or O;
 (v) R$^5$ is H or C$_1$-C$_4$alkyl;
 (vi) R$^7$, R$^8$ and R$^9$ are independently H or optionally substituted C$_1$-C$_6$alkyl, C$_3$-C$_{10}$cycloalkyl, C$_3$-C$_{10}$heterocycloalkyl, hydroxy, C$_{1-6}$alkoxy, nitro, halo, haloC$_1$-C$_6$alkyl, aryl, arylC$_1$-C$_6$alkyl, heteroaryl or heteroarylC$_1$-C$_6$alkyl;
 (vii) R$^{10}$ is H or C$_{1-4}$alkyl when X is N or R$^{10}$ is non-existent when X is O or S;
 (viii) R$^{6a}$ and R$^{6b}$ are H; and
 (ix) R$^1$ is H or optionally substituted C$_1$-C$_6$alkyl, cycloalkyl, aryl, arylC$_1$-C$_6$alkyl (e.g., benzyl), heteroaryl, heteroarylC$_1$-C$_6$alkyl, aryloxoC$_1$-C$_6$alkyl (e.g., 4-(4-fluorophenyl)-4-oxobutyl)), aryloxyC$_1$-C$_6$alkyl (e.g., 3-(4-fluorophenoxy)propyl)), heroaryloxoC$_1$-C$_6$alkyl, heroaryloxyC$_1$-C$_6$alkyl, aryl sulfinylC$_1$-C$_6$alkyl or heteroaryl sulfinylC$_1$-C$_6$alkyl;
which method comprises the step of N-alkylating compounds of Formula 2I:

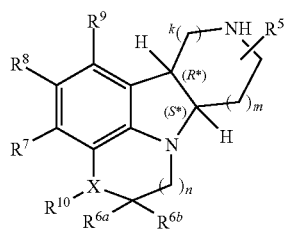

Formula 2I as hereinbefore described, with (a) a compound of the general formula:

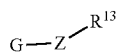

wherein:
 (i) Z is —C(O)—, —O—, or S(O)$_2$—;
 (ii) R$^{13}$ is optionally substituted aryl, arylC$_1$-C$_6$alkyl, C$_1$-C$_6$alkyl, heteroaryl, heteroarylC$_1$-C$_6$alkyl; and
 (iii) G is C$_1$-C$_8$alkyl halide (e.g., propyl chloride);
and (b) a base.

The base useful for Method 1J or 2J may be a Bronsted or Lewis base. Examples of such bases include, but are not limited to amine bases (e.g., ammonium, triethylamine, N,N'-diisopropylethyl amine or 4-(dimethylamino)pyridine (DMAP); 1,5-diazabicycl[4.3.0]-non-5-ene (DBN), 1,5-diazabicyclo[5.4.0]undec-5-ene (DBU)); or hydrides (e.g. sodium, lithium or potassium hydride), alkoxides, (e.g. sodium, potassium or lithium t-butoxide and K(OAr), Na(OAr)), or carbonate, bicarbonate, phosphate or hydroxide of alkali or alkaline earth metals (e.g. sodium, magnesium, calcium, potassium, cesium or barium carbonate, bicarbonate, hydroxide or phosphate). Optionally, Method 1I further comprises the use of sodium or potassium iodide. In a preferred embodiment, compounds of Formula 1I are alkylated with 4-chloro-4'-fluoro-butyrophenone in the presence of triethyl amine and potassium iodide.

In another aspect, the invention provides a method (Method 1K) for preparing pharmaceutically acceptable salts of compounds of Formula 1J or 2J:

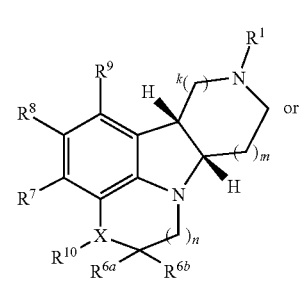

Formula 1J

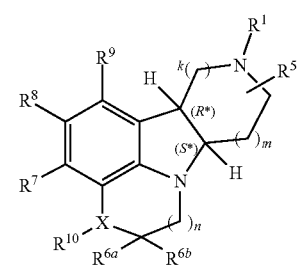

Formula 2J as hereinbefore described, which method comprises the step of reacting free base of Compounds of Formula 1J or 2J with an appropriate acid in water or in an organic solvent, or in a mixture of the two to give pharmaceutically acceptable acid addition salts of Formula 1J or 2J of the present invention; generally, nonaqueous media like ether, ethyl acetate, ethanol, isopropanol, or acetonitrile are preferred. Appropriate acid may be, for example, hydrochloric, hydrobromic, sulfuric, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The invention further provides methods for compounds of Formulas 1C-1J (e.g., Formulas, 1C, 1D, 1E, 1E', 1F", 1G', 1G, 1H, 1I and 1J) as follows:

3.1 Method for the preparation of any compounds of Formula 1J comprising the step of treating compounds of Formula 1I with 1-(3-chloropropoxy)-4-fluorobenzene and a base.

3.2 Method for the preparation of any compounds of Formula 1J comprising the step of treating compounds of Formula 1I with 1-(3-chloropropoxy)-4-fluorobenzene and triethylamine.

3.3 Method for the preparation of any compounds of Formula 1J comprising the step of treating compounds of Formula 1I with 4-chloro-4'-fluoro-butyrophenone and a base.

3.4 Method for the preparation of any compounds of Formula 1J comprising the step of treating compounds of Formula 1I with 4-chloro-4'-fluoro-butyrophenone and triethylamine.

3.5 Method for the preparation of any compounds of Formulas 1J, 1I or any of Method 3.1-3.4, comprising the step of deprotecting compounds of Formula 1H.

3.6 Method for the preparation of any compounds of Formulas 1J or 1I or any of Methods 3.1-3.4, comprising the step of deprotecting compounds of Formula 1H with sodium hydroxide.

3.7 Method for the preparation of any compounds of Formulas 1J, 1I or any of Methods 3.1-3.4 comprising the step of deprotecting compounds of Formula 1H with trifluoroacetic acid.

3.8 Method for the preparation of any compounds of Formulas 1J-1H or any of Methods 3.1-3.7 comprising the step of treating compounds of Formula 1G' with a reducing agent.

3.9 Method for the preparation of any compounds of Formulas 1J-1H or any of Methods 3.1-3.7 comprising the step of treating compounds of Formula 1G' with borane-THF.

3.10 Method for the preparation of any compounds of Formulas 1J-1G or any of Methods 3.1-3.9 comprising the step of treating compounds of Formula 1F with an alkyl halide and a base.

3.11 Method for the preparation of any compounds of Formulas 1J-1G or any of Methods 3.1-3.9 comprising the step of treating compounds of Formula 1F with a methyl iodide and potassium carbonate.

3.12 Method for the preparation of any compounds of Formulas 1J-1G, 1F" or any of Methods 3.1-3.11, comprising the step of treating compounds of Formula 1E' with (a) A—(CH$_2$)—C(O)—OR, wherein R is H or alkyl; and (b) base.

3.13 Method for the preparation of any compounds of Formulas 1J-1G, 1F" or any of Methods 3.1-3.11, comprising the step of treating compounds of Formula 1E' with ethyl bromoacetate and sodium carbonate.

3.14 Method for the preparation of any of compounds of Formulas 1J-1G, 1F", or any of Methods 3.1-3.11, comprising the step of treating compounds of Formula 1E' with ethyl bromoacetate, sodium carbonate and potassium iodide.

3.15 Method for the preparation of any compounds of Formulas 1J-1F or any of Methods 3.1-3.11 comprising the step of treating compounds of Formula 1E with a transition metal catalyst selected from Groups 8-11 of the periodic table and a base.

3.16 Method for the preparation of any compounds of Formulas 1J-1F or any of Methods 3.1-3.11 comprising the step of treating compounds of Formula 1E with a copper catalyst and a base.

3.17 Method for the preparation of any compounds of Formulas 1J-1F or any of Methods 3.1-3.11 comprising the step of treating compounds of Formula 1E with CuI and a base.

3.18 Method for the preparation of any compounds of Formulas 1J-1F or any of Methods 3.1-3.11 comprising the step of treating compounds of Formula 1E with CuI and a Bronsted base.

3.19 Method for the preparation of any compounds of Formulas 1J-1F or any of Methods 3.1-3.11 comprising the step of treating compounds of Formula 1E with CuI and potassium carbonate.

3.20 Method for the preparation of any compounds of Formulas 1J-1F or any of Methods 3.1-3.11 comprising the step of treating compounds of Formula 1E with a transition metal catalyst selected from Groups 8-11, base and a mono or bidentate ligand.

3.21 Method for the preparation of any compounds of Formulas 1J-1F or any of Methods 3.1-3.11 comprising the step of treating compounds of Formula 1E with CuI, potassium carbonate and N,N'-dimethylethylenediamine.

3.22 Method for the preparation of any compounds of Formulas 1J-1F, 1E or any of Methods 3.1-3.21 comprising the step of treating compounds of Formula 1D with (a) a compound of the general formula X—Y—(CH$_2$)$_n$-A as hereinbefore described; and (b) a base.

3.23 Method for the preparation of any compounds of Formulas 1J-1F, 1E or any of Methods 3.1-3.21 comprising the step of treating compounds of Formula 1D with 2-chloroacetamide and diisopropylethylamine.

3.24 Method for the preparation of any compounds of Formulas 1J-1F, 1E or any of Methods 3.1-3.21 comprising the step of treating compounds of Formula 1D with 2-chloroacetamide, diisopropylethylamine and sodium or potassium iodide.

3.25 Method for the preparation of any compounds of Formulas 1J-1F, 1F" or 1E' or any of Methods 3.1-3.21 comprising the step of treating compounds of Formula 1D with benzophenone imine; palladium catalyst; base and 2,2'-bis(diphenylphosphino)-1,1'-binaphthyl.

3.26 Method for the preparation of any compounds of Formulas 1J-1F, 1F" or 1E' or any of Methods 3.1-3.21 comprising the step of treating compounds of Formula 1D with benzophenone imine; Pd$_2$(dba)$_2$; sodium t-butoxide; and 2,2'-bis(diphenylphosphino)-1,1'-binaphthyl.

3.27 Method for the preparation of any compounds of Formulas 1J-1F, 1F", 1E, 1E', 1D or any of Methods 3.1-3.26 comprising the step of protecting compounds of Formula 1C with a protecting agent.

3.28 Method for the preparation of any compounds of Formulas 1J-1F, 1F", 1E, 1E', 1D or any of Methods 3.1-3.26 comprising the step of protecting compounds of Formula 1C with a protecting agent having the general formula of Y–P–Z as hereinbefore described in the presence of a base.

3.29 Method for the preparation of any compounds of Formulas 1J-1F, 1F", 1E, 1E', 1D or any of Methods 3.1-3.26 comprising the step of protecting compounds of Formula 1C with ethyl chloroformate and a base.

3.30 Method for the preparation of any compounds of Formulas 1J-1F, 1F", 1E, 1E', 1D or any of Methods 3.1-3.26 comprising the step of protecting compounds of Formula 1C with ethyl chloroformate and triethylamine.

3.31 Method for the preparation of any of compounds of Formulas 1J-1F, 1F''', 1E, 1E', 1D or any of Methods 3.1-3.26 comprising the step of protecting compounds of Formula 1C with Boc anhydride and a base.

3.32 Method for the preparation of any of compounds of Formulas 1J-1F, 1F''', 1E, 1E', 1D, 1C or any of Methods 3.1-3.31 comprising the step of (a) reducing compounds of Formula 1 A with a reducing agent and (b) resolving compounds of Formula 1B with a chiral acid.

3.33 Method for the preparation of any of compounds of Formulas 1J-1F, 1F''', 1E, 1E', 1D, 1C or any of Methods 3.1-3.31 comprising the step of (a) reducing compounds of Formula 1A with sodium cyanoborohydride and (b) resolving compounds of Formula 1B with a chiral acid.

3.34 Method for the preparation of any of compounds of Formulas 1J-1F, 1F''', 1E, 1E', 1D, 1C or any of Methods 3.1-3.31 comprising the step of (a) reducing compounds of Formula 1A with triethylsilane in the presence of an acid and (b) resolving compounds of Formula 1B with a chiral acid.

3.35 Method for the preparation of any of compounds of Formulas 1J-1F, 1F''', 1E, 1E', 1D, 1C or any of Methods 3.1-3.31 comprising the step of (a) reducing compounds of Formula 1A with triethylsilane in the presence of trifluoroacetic acid; and (b) separating the enantiomers of compounds of Formula 1B by chiral acid resolution or by chiral chromatography.

3.36 Method for the preparation of any of compounds of Formulas 1J-1F, 1F''', 1E, 1E', 1D, 1C or any of Methods 3.1-3.31 comprising the step of (a) reducing compounds of Formula 1A with triethylsilane in the presence of trifluoroacetic acid; and (b) separating the enantiomers of compounds of Formula 1B by chiral acid resolution or by chiral chromatography.

3.37 Method for the preparation of any of compounds of Formulas 1J-1F, 1F''', 1E, 1E', 1D, 1C or any of Methods 3.1-3.31 comprising the step of (a) reducing compounds of Formula 1A with triethylsilane in the presence of trifluoroacetic acid; and (b) separating the enantiomers of compounds of formula 1B by chiral chromatography.

3.38 Method for the preparation of any of compounds of Formulas 1J-1F, 1F''', 1E, 1E', 1D, 1C or any of Methods 3.1-3.31 comprising the step of (a) reducing compounds of Formula 1A with triethylsilane in the presence of trifluoroacetic acid; and (b) separating te enantiomers of compounds of formula 1B by the use of amylase tris(3,5-dimethylphenylcarbamate) column.

3.39 Method for the preparation of any of compounds of Formulas 1J-1F, 1F''', 1E, 1E', 1D, 1C or any of Methods 3.1-3.31 comprising the step of (a) reducing compounds of Formula 1A with triethylsilane in the presence of trifluoroacetic acid; and (b) separating te enantiomers of compounds of formula 1B by the use of amylase tris(3,5-dimethylphenylcarbamate) column and eluting the desired product with ethanol mobile phase.

3.40 Method for the preparation of any of compounds of Formulas 1J-1F, 1F''', 1E, 1E', 1D, 1C or any of Methods 3.1-3.31 comprising the step of (a) reducing compounds of Formula 1A with triethylsilane in the presence of trifluoroacetic acid; and (b) resolving compounds of Formula 1B with (S)-(+)-mandelic acid.

3.41 Method for the preparation of any of compounds of Formulas 1J-1F, 1F''', 1E, 1E', 1D, 1C or any of Methods 3.1-3.31 comprising the step of (a) reducing compounds of Formula 1A with a reducing agent; and (b) resolving compounds of Formula 1B with (S)-(+)-mandelic acid.

3.42 Method for the preparation of any of compounds of Formulae 1J-1F, 1F''', 1E, 1E', 1D, 1C or any of Methods 3.1-3.31 comprising the step of (a) reducing compounds of Formula 1 A with triethylsilane in the presence of trifluoroacetic acid; and (b) resolving compounds of Formula 1B with (S)-(+)-mandelic acid.

The invention further provides methods for compounds of Formulas 2C-2J (e.g., Formulas, 2C, 2D, 2E, 2E', 2F, 2G', 2G, 2H, 2I and 2J) as follows:

4.1 Method for the preparation of pharmaceutically acceptable acid addition salts of any compounds of Formula 2J comprising the step of treating free base of Compounds of Formula 2J with an acid to give pharmaceutically acceptable acid addition salts of Formula 1J or 2J of the present invention.

4.2 Method 4.1 wherein said acid is selected from a group consisting of hydrochloric, hydrobromic, sulfuric, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic acid.

4.3 Method for the preparation of any compounds of Formula 2J or 4.1-4.2, comprising the step of treating compounds of Formula 21 with 1-(3-chloropropoxy)-4-fluorobenzene and a base.

4.4 Method for the preparation of any compounds of Formula 2J comprising the step of treating compounds of Formula 21 with 1-(3-chloropropoxy)-4-fluorobenzene and triethylamine or diisopropylethylamine.

4.5 Method for the preparation of any compounds of Formula 2J comprising the step of treating compounds of Formula 21 with 4-chloro-4'-fluoro-butyrophenone and a base.

4.6 Method for the preparation of any compounds of Formula 2J comprising the step of treating compounds of Formula 21 with 4-chloro-4'-fluoro-butyrophenone and triethylamine or diisopropylethylamine.

4.7 Method for the preparation of any compounds of Formulas 2J, 2I or any of Method 4.1-4.6, comprising the step of deprotecting compounds of Formula 2H.

4.8 Method for the preparation of any compounds of Formulas 2J or 2I or any of Methods 4.1-4.7, comprising the step of deprotecting compounds of Formula 2H with a base (e.g., sodium hydroxide or potassium hydroxide).

4.9 Method for the preparation of any compounds of Formulas 2J, 2I or any of Methods 4.1-4.7 comprising the step of deprotecting compounds of Formula 2H with trifluoroacetic acid.

4.10 Method for the preparation of any compounds of Formulas 2J-2H or any of Methods 4.1-4.9 comprising the step of treating compounds of Formula 2G' with a reducing agent.

4.11 Method for the preparation of any compounds of Formulas 2J-2H or any of Methods 4.1-4.9 comprising the step of treating compounds of Formula 2G' with borane-THF.

4.12 Method for the preparation of any compounds of Formulas 2J-2G or any of Methods 4.1-4.11 comprising the step of treating compounds of Formula 2F with an alkyl halide and a base.

4.13 Method for the preparation of any compounds of Formulas 2J-2G or any of Methods 4.1-4.11 comprising the step of treating compounds of Formula 2F with a methyl iodide and potassium carbonate.

4.14 Method for the preparation of any compounds of Formulas 2J-2G, 2F'" or any of Methods 4.1-4.13, comprising the step of treating compounds of Formula 1E' with (a) A—(CH$_2$)—C(O)—OR, wherein R is H or alkyl; and (b) base.

4.15 Method for the preparation of any compounds of Formulas 2J-2G, 2F'" or any of Methods 4.1-4.14, comprising the step of treating compounds of Formula 2E' with ethyl bromoacetate and sodium carbonate.

4.16 Method for the preparation of any of compounds of Formulas 2J-2G,2F'", or any of Methods 4.1-4.13, comprising the step of treating compounds of Formula 2E' with ethyl bromoacetate, sodium carbonate and potassium iodide.

4.17 Method for the preparation of any compounds of Formulas 2J-2F or any of Methods 4.1-4.13 comprising the step of treating compounds of Formula 2E with a transition metal catalyst selected from Groups 8-11 of the periodic table and a base.

4.18 Method for the preparation of any compounds of Formulas 2J-2F or any of Methods 4.1-4.13 comprising the step of treating compounds of Formula 2E with a copper catalyst and a base.

4.19 Method for the preparation of any compounds of Formulas 2J-2F or any of Methods 4.1-4.13 comprising the step of treating compounds of Formula 2E with CuI and a base.

4.20 Method for the preparation of any compounds of Formulas 2J-2F or any of Methods 4.1-4.13 comprising the step of treating compounds of Formula 2E with CuI and a Bronsted base.

4.21 Method for the preparation of any compounds of Formulas 2J-2F or any of Methods 4.1-4.13 comprising the step of treating compounds of Formula 2E with CuI and potassium carbonate.

4.22 Method for the preparation of any compounds of Formulas 2J-2F or any of Methods 4.1-4.21 further comprising a mono or bidentate ligand.

4.23 Method for the preparation of any compounds of Formulas 2J-2F or any of Methods 4.1-4.13 comprising the step of treating compounds of Formula 2E with a transition metal catalyst selected from Groups 8-11, base and a mono or bidentate ligand.

4.24 Method for the preparation of any compounds of Formulas 2J-2F or any of Methods 4.1-4.23 comprising the step of treating compounds of Formula 3E with CuI, potassium carbonate and N,N'-dimethylethylenediamine.

4.25 Method for the preparation of any compounds of Formulas 2J-2F, 2E or any of Methods 4.1-4.24 comprising the step of treating compounds of Formula 2D with (a) a compound of the general formula X—Y—(CH$_2$)$_n$-A as hereinbefore described; and (b) a base.

4.26 Method for the preparation of any compounds of Formulas 2J-2F, 2E or any of Methods 4.1-4.24 comprising the step of treating compounds of Formula 2D with 2-chloroacetamide and diisopropylethylamine.

4.27 Method for the preparation of any compounds of Formulas 2J-2F, 2E or any of Methods 4.1-4.24 comprising the step of treating compounds of Formula 2D with 2-chloroacetamide, diisopropylethylamine and sodium or potassium iodide.

4.28 Method for the preparation of any compounds of Formulas 2J-2F, 2F'" or 2E' or any of Methods 4.1-4.24 comprising the step of treating compounds of Formula 2D with benzophenone imine; palladium catalyst; base and 2,2'-bis(diphenylphosphino)-1,1'-binaphthyl.

4.29 Method for the preparation of any compounds of Formulas 2J-2F, 2F'" or 2E' or any of Methods 4.1-4.24 comprising the step of treating compounds of Formula 2D with benzophenone imine; Pd$_2$(dba)$_2$; sodium t-butoxide; and 2,2'-bis(diphenylphosphino)-1,1'-binaphthyl.

4.30 Method for the preparation of any compounds of Formulas 2J-2F, 2F'", 2E, 2E', 2D or any of Methods 4.1-4.29 comprising the step of protecting compounds of Formula 2C with a protecting agent.

4.31 Method for the preparation of any compounds of Formulas 2J-2F, 2F'", 2E, 2E', 2D or any of Methods 4.1-4.30 comprising the step of protecting compounds of Formula 2C with a protecting agent having the general formula of Y-P-Z as hereinbefore described in the presence of a base.

4.32 Method for the preparation of any compounds of Formulas 2J-2F, 2F'", 2E, 2E', 2D or any of Methods 4.1-4.30 comprising the step of protecting compounds of Formula 2C with ethyl chloroformate and a base.

4.33 Method for the preparation of any compounds of Formulas 2J-2F, 2F'", 2E, 2E', 2D or any of Methods 4.1-4.32 comprising the step of protecting compounds of Formula 2C with ethyl chloroformate and triethylamine.

4.34 Method for the preparation of any of compounds of Formulas 2J-2F, 2F'", 2E, 2E', 2D or any of Methods 4.1-4.31 comprising the step of protecting compounds of Formula 1C with Boc anhydride and a base.

4.35 Method for the preparation of any of compounds of Formulas 2J-2F, 2F'", 2E, 2E', 2D, 2C or any of Methods 4.1-4.35 comprising the step of (a) reducing compounds of Formula 2A with a reducing agent and (b) resolving compounds of Formula 2B with a chiral acid or by chiral chromatography.

4.36 Method for the preparation of any of compounds of Formulas 2J-2F, 2F'", 2E, 2E', 2D, 2C or any of Methods 4.1-4.35 comprising the step of (a) reducing compounds of Formula 2A with sodium cyanoborohydride and (b) resolving compounds of Formula 2B with a chiral acid or by chiral chromatography.

4.37 Method for the preparation of any of compounds of Formulas 2J-2F, 2F'", 2E, 2E', 2D, 2C or any of Methods 4.1-4.35 comprising the step of (a) reducing compounds of Formula 2A with triethylsilane in the presence of an acid and (b) resolving compounds of Formula 2B with a chiral acid or by chiral chromatography.

4.38 Method for the preparation of any of compounds of Formulas 2J-2F, 2F'", 2E, 2E', 2D, 2C or any of Methods 4.1-4.33 or 4.37 comprising the step of (a) reducing compounds of Formula 2A with triethylsilane in the presence of trifluoroacetic acid; and (b) separating the enantiomers of compounds of Formula 2B by chiral acid resolution or by chiral chromatography.

4.39 Method for the preparation of any of compounds of Formulas 2J2F, 2F'", 2E, 2E', 2D, 2C or any of Methods 4.1-4.35 or 4.37-4.38 comprising the step of (a) reducing compounds of Formula 2A with triethylsilane in the presence of trifluoroacetic acid; and (b) separating the enantiomers of compounds of Formula 2B by chiral acid resolution or by chiral chromatography.

4.40 Method for the preparation of any of compounds of Formulas 2J-2F, 2F''', 2E, 2E', 2D, 2C or any of Methods 4.1-4.39 comprising the step of (a) reducing compounds of Formula 2A with triethylsilane in the presence of trifluoroacetic acid; and (b) resolving compounds of Formula 2B with (S)-(+)-mandelic acid.

4.41 Method for the preparation of any of compounds of Formulas 2J-2F, 2F''', 2E, 2E', 2D, 2C or any of Methods 4.1-4.39 comprising the step of (a) reducing compounds of Formula 2A with a reducing agent; and (b) resolving compounds of Formula 2B with (S)-(+)-mandelic acid.

4.42 Method for the preparation of any of compounds of Formulas 2J-2F, 2F''', 2E, 2E', 2D, 2C or any of Methods 4.1-4.39 comprising the step of (a) reducing compounds of Formula 2A with triethylsilane in the presence of trifluoroacetic acid; and (b) resolving compounds of Formula 2B with (S)-(+)-mandelic acid.

4.43 Method for the preparation of any of compounds of Formulas 2J-2F, 2F''', 2E, 2E', 2D, 2C or any of Methods 4.1-4.35 comprising the step of (a) reducing compounds of Formula 2A with triethylsilane in the presence of trifluoroacetic acid; and (b) separating the enantiomers of compounds of formula 2B by chiral chromatography.

4.44 Method for the preparation of any of compounds of Formulas 2J-2F, 2F''', 2E, 2E', 2D, 2C or any of Methods 4.1-4.35 or 4.43 comprising the step of (a) reducing compounds of Formula 2A with triethylsilane in the presence of trifluoroacetic acid; and (b) separating te enantiomers of compounds of formula 2B by the use of amylase tris(3,5-dimethylphenylcarbamate) column.

4.45 Method for the preparation of any of compounds of Formulas 2J-2F, 2F''', 2E, 2E', 2D, 2C or any of Methods 4.1-4.35 or 4.43-4.44 comprising the step of (a) reducing compounds of Formula 2A with triethylsilane in the presence of trifluoroacetic acid; and (b) separating te enantiomers of compounds of formula 2B by the use of amylase tris(3,5-dimethylphenylcarbamate) column and eluting the desired product with ethanol, methanol or isopropyl alcohol mobile phase.

DETAILED DESCRIPTION OF THE INVENTION

The compounds described herein and their pharmaceutically acceptable salts may be made using the methods as described and exemplified herein and by methods similar thereto and by methods known in the chemical art. In the description of the synthetic methods described herein, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Therefore, at times, reaction may require to be run at elevated temperature or for a longer or shorter period of time. It is understood by one skilled in the art of organic synthesis that functionality present on various portions of the molecule must be compatible with the reagents and reactions proposed. If not commercially available, starting materials for these processes may be made by procedures, which are selected from the chemical art using techniques similar or analogous to the synthesis of known compounds. All references cited herein are hereby incorporated in their entirety by reference.

The numbering of the tetracyclic ring-system as described herein is shown below as an example, when k is 1, m is 1, and n is 1:

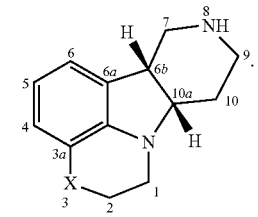

The numbering of the hexahydro-1H-pyrido[4,3-b]indole derivative as described herein is shown below as an example, wherein k is 1, m is 1, and n is 1:

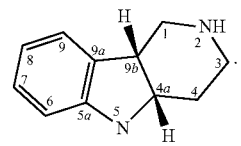 [SMILES: c1ccc2c(c1)N[C@H]1CCNC[C@@H]21]

Unless the terms are specifically defined for an embodiment, the terms used herein are generally defined as follows.

The phrase "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The term "alkyl" or "alkylene" is intended to include both branched and straight-chain saturated aliphatic hydrocarbon groups having the specified number of carbon atoms; for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, 3-methylpentyl, 4-methylpentyl, etc.

"Alkenyl" or "alkenylene" is intended to include hydrocarbon chains of either a straight or branched configuration having a specified number of carbon atoms and one or more carbon-carbon double bonds which may occur in any stable point along the chain. Examples of alkenyl include, but are not limited to, ethenyl, 1-propenyl, 2-butenyl, 3-butenyl, 2-pentenyl, 4-pentenyl, 2-hexenyl, 3-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain, such as ethynyl, propynyl, butynyl, pentynyl, hexynyl and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" is represents an alkyl group as defined above with the indicated number of carbon atoms attached through a sulphur bridge.

"Halo", "halogen" or "halide" as used herein refers to fluoro, chloro, bromo, and iodo. Therefore, "alkyl halide" herein refers to a halogen group attached to alkyl group as defined above such as methyl iodide or iodobutane.

"Cycloalkyl" is intended to include monocyclic or polycyclic ring system comprising at least one aliphatic ring. Therefore, "cycloalkyl" may denote simply a cyclopropyl, cyclobutyl, cyclopentyl, cyclopentenyl, cyclohexyl, cyclohexenyl and the like. Wherein cycloalkyl is a polycyclic system, such system may contain an aliphatic ring fused to aromatic, non-aromatic, heteroaromatic or hetero nonaromatic rings such as octahydro-1H-indene, 2,3-dihydro-1H-indene or 5,6,7,8-tetrahydroquinoline.

The term "heterocycloalkyl" herein refers to a monocyclic or polycyclic system comprising at least one aliphatic ring containing at least one heteroatom selected from a group consisting of O, N and S. Therefore, heterocycloalkyl may refer to piperidinyl, piperazinyl, 2-pyrrolidonyl, 1,2,3,4-tetrahydroquinolinyl, 2H,6H-1,5,2-dithiazinyl, 2H-pyrrolyl or 1,2,3,4-tetrahydro-1,8-naphthyridine.

As used herein, the term "aryl" is intended to mean a stable 5- to 7-membered monocyclic or polycyclic or 7- to 14-membered polycyclic ring system which comprises at least one aromatic ring (i.e., planar ring that contains 4n+2 Pi electrons, wherein n is an integer). Therefore, the term "aryl" includes phenyl, naphthyl and their derivatives. The term "aryl" is also intended to include polycyclic ring systems which contain at least one aromatic ring fused to one or more aromatic or non-aromatic or heteroaromatic rings (e.g., 2,3-dihydro-1H-indene).

As used herein, the term "heterocycle", "heterocyclic ring" or "heteroaryl" is intended to mean a stable 5- to 7-membered monocyclic or polycyclic or 7- to 14-membered polycyclic ring which comprises at least one aromatic ring containing at least one heteroatom independently selected from the group consisting of N, O and S. Therefore, a "heterocycle" or "heterocyclic ring" or "heteroaryl" may include a single hetero aromatic ring or a hetero aromatic ring fused to other heteroaromatic ring or to a non-heteroaromatic or non-aromatic ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of heterocycles or heteroaryl group include, but are not limited to 1H-indazole, thiazolyl, furyl, pyridyl, quinolinyl, pyryl, indole or 5,6,7,8-tetrahydroquinoline.

The term "polycyclic" or "polycycle" is intended to mean fused ring system comprising one or more aromatic, non-aromatic (i.e., alicyclic), heteroaromatic or hetero non-aromatic (hetero-alicyclic) rings fused together.

The term "substituted," as used herein, means that any one or more hydrogens on the designated atom is replaced with a selection from the indicated group, provided that the designated atom's normal valency is not exceeded, and that the substitution results in a stable compound. Therefore, optionally substituted alkyl may refer to an alkyl group as defined above whereby one or more hydrogens are replaced with a selection from the indicated group including, but not limited to, halogen, hydroxy, amino, sulfhydryl, alkyl, alkenyl, alkynyl, haloalkyl (e.g. $CH_2Cl$, $CF_3$, $CH_3CH_2Br$, etc.), amine, amido, aryl, arylalkyl, heteroaryl, heteroarylalkyl, cycloalkyl, heterocycloalkyl, alkoxy, carboxy, carbonyl, silyl, alkylamino, alkylamido, nitro, cyano, halo, —S(O)-alkyl, —S(O)$_2$-alkyl, R-cycloalkyl, R-heterocycloalkyl, R—C(O)—, R—C(O)—OR', R—O—R', —N(R)(R') wherein R and R' are independently H, alkyl, aryl, heteroaryl, cycloalkyl, heterocycloalkyl, arylalkyl, heteroarylalkyl, heteroarylalkyl or heterocycloalkyl.

The term "resolution" is a term of art and refers to the separation of a racemic mixture into its enantiomers by reacting an organic acid or base with the components of the racemic mixture to form diasteromeric salts and separating said salt by, for example, crystallization techniques. The term "chiral acid resolution" refers to the separation of a racemic mixture into its enantiomers through the use of a chiral acid.

The term "chromatography" is well known in the art and refers to a separation technique of a mixture by interacting it with a stationary phase and eluting the components of the mixture with a mobile phase such as ethanol, methanol, acetonitrile, water or mixtures thereof. The term "chiral chromatography" refers to chromatography wherein the stationary phase is chiral.

The term "chiral acid" refers to any optically active acid capable of forming disastereomeric salts with compounds of Formula 1B. The terms "mono or di-carboxylic acid" or "sulfonic acid" herein refers to any compound that contains one or two carboxylic functional groups and a sulfonic acid group respectively. Examples of such acid include but are not limited to (+/−)/(R/S) tartaric acid, (+/−)/(R/S) (mono- or di-acetyl)tartaric acid, (+/−)/(R/S) (mono- or di-benzoyl) tartaric acid, (+/−)/(R/S) (mono- or di-pivaloyl)tartaric acid, (+/−)/(R/S) mandelic acid, (+/−)/(R/S) acetoxyphenyl acetic acid, (+/−)/(R/S) methoxyphenyl acetic acid, (+/−)/(R/S) hydroxymandelic acid, (+/−)/(R/S) halomandelic acid (e.g. 4-fluoromandelic acid), (+/−)/(R/S) lactic acid, and (+/−)/(R/S) camphor sulfonic acid.

The term "protecting agent" refers to any compound that reacts with the atom for which protection is desired so as to block or mask its functionality. It is typically used to temporarily modify a potentially reactive functional group so as to protect it from undesired chemical transformation. A desirable protecting agent is one which is compatible with or stable to the reaction condition and is easily cleaved off at a later point when protection is no longer desired. For examples of protecting agents, see "Protective Groups in Organic Synthesis" by Theodora Green (publisher: John Wiley & Sons), the disclosure of which is hereby incorporated by reference.

The term "deprotection" or "deprotect" or "deprotecting" refers to the act of removing or cleaving off a protecting group. The deprotection conditions for the above protecting groups necessarily vary with the choice of protecting group and may involve acid (e.g., hydrochloric, sulphuric, phosphoric or trifluoroacetic acid or a Lewis acid such as boron tris(trifluoroacetate)) or base (alkali metal hydroxide, e.g., lithium, potassium or sodium hydroxide) catalysis or catalytic hydrogenation condition (e.g., hydrogen and palladium-on-carbon).

The term "catalyst" herein refers to any substance or agent capable of affecting, inducing, increasing, influencing or promoting the reactivity of a compound or reaction without itself being consumed. The phrase "transition metal catalyst" refers to any metal having electrons in the d-orbitals, e.g. metals selected from one of Groups 3-12 of the periodic table or from the lanthanide series. The catalysts useful for the methods of this invention include atoms, ions, salts or complexes of transition metals from Groups 8-11 of the Periodic Table. "Group 3-12 of the Periodic Table" refers to the groups of the Periodic Table as numbered according to the IUPAC system. Therefore, transition metals from Group 8-11 which include include iron, ruthenium, osmium, cobalt, rhodium, iridium, nickel, palladium, platinum, copper, silver and gold. Examples of such catalysts include, but are not limited to CuI, CuCl, CuBr, $CuBr_2$, Cu(II) acetate, $Cu_2Cl_2$, $Cu_2O$, Cu, $Pd_2(dba)_2$, Pd/C, $PdCl_2$, $Pd(OAc)_2$, $(CH_3CN)_2PdCl_2$, $Pd[P(C_6H_5)_3]_4$, bis(dibenzylideneacetone) palladium $[Pd_2(dba)_3]$, $Ni(acetylacetonate)_2$, $NiCl_2[P(C_6H_5)]_2$ and $Ni(1,5-cyclooctadiene)_2$. Catalysts are typically, but not necessarily used in substoichiometric amount relative to the reactants. Preferably, 0.5-20 mol %, most preferably, 10 mol % of the transition metal catalyst relative to the reactants is used.

The term "base" herein refers to organic or inorganic bases such as amine bases (e.g., ammonium, triethylamine, N,N'-diisopropylethyl amine or 4-(dimethylamino)pyridine (DMAP); 1,5-diazabicycl[4.3.0]-non-5-ene (DBN), 1,5-diazabicyclo[5.4.0]undec-5-ene (DBU)); hydrides (e.g. sodium, lithium or potassium hydride); alkoxides, (e.g. sodium, potassium or lithium t-butoxide and K(OAr), Na(OAr)); or carbonate, bicarbonate, phosphate or hydroxide of an alkali or alkaline earth metal (e.g. sodium, magnesium, calcium, potassium, cesium or barium carbonate, bicarbonate, hydroxide or phosphate).

The term "Bronsted base" is art-recognized and refers to an uncharged or charged atom or molecule, e.g., an oxide, amine, alkoxide, or carbonate, that is a proton acceptor. Examples of Bronsted base include, but not limited to $K_3PO_4$, $K_2CO_3$, $Na_2CO_3$, $Tl_2CO_3$, $Cs_2CO_3$, K(OtBu), Li(OtBu), Na(OtBu), K(OPh), and Na(OPh), or mixtures thereof.

The term "Lewis base" are recognized in the art, and refer to a chemical moiety capable of donating a pair of electrons under certain reaction conditions. Examples of Lewis base include but are not limited to uncharged compounds such as alcohols, thiols, olefins, and amines (e.g., ammonia, triethylamine), and charged moieties such as alkoxides, thiolates, carbanions, and a variety of other organic anions.

The term "acid" herein refers to Lewis or Bronsted acid. Lewis acid is a term of art and refers to a chemical moiety capable of accept a pair of electrons (e.g., borontrifluoride). Bronsted acid refers to any chemical moiety capable of donating a proton (e.g., acetic acid, trifluoroacetic acid, hydrochloric acid, hydrobromic acid, sulfuric acid, phosphoric acid as well as other organic acids known in the art).

The term "ligand" refers to any atom, molecule or ion capable of donating or sharing one or more electrons through a coordinate and/or covalent bond with another central atom, typically a metal. "Monodentate ligand" refers to ligands that have one binding site to the central atom (e.g., pyridine or ammonia). "Bidentate ligand" refers to ligands that have two binding site (e.g., N,N'-dimethylethylenediamine, N,N,N',N'-tetramethylethylenediamine or 1,10-phenathroline). Examples of useful ligands for group 8-11 transition metals include, but not limited to, 2-phenylphenol, 2,6-dimethylphenol, 2-isopropylphenol, 1-naphthol, 8-hydroxyquinoline, 8-aminoquinoline, DBU, 2-(dimethylamino)ethanol, N,N-diethylsalicylamide, 2-(dimethylamino)glycine, N,N,N',N'-tetramethyl-1,2-diaminoethane, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, (methylimino)diacetic acid, cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and tans-N-tolyl-1,2-diaminocyclohexane, ethanolamine, 1,2-diaminoethane, N,N'-dimethyl-1,2-diaminoethane, N,N-dimethyl-2-hydroxybenzamide, N,N-diethyl-2-hydroxybenzamide, fluoro-N,N-diethyl-2-hydroxybenzamide, chloro-N,N'-diethyl-2-hydroxybenzamide, (2-hydroxyphenyl)(pyrrolidin-1-yl)methanone, biphenyl-2-ol, 2-pyridylphenol, 1,2-benezenediamine, ammonia, N,N-dimethylformamide, dimethylsulfoxide, 1-methyl-2-pyrrolidinone or mixtures thereof as well as the biphenyl and binaphtyl ligands hereinbefore described. In certain embodiments, the amount of ligand used may be stoichiometric or excess amount. In other embodiments, ligand may be used as a solvent for the reaction. Therefore, reagents such as N,N-dimethylformamide, dimethylsulfoxide, 1-methyl-2-pyrrolidinone or other liquid amines may serve as a solvent as well as ligand for the reaction.

The term "N,N'-dimethylethylenediamine" is used interchangeably with "N,N'-dimethyl-1,2-diaminoethane".

The phrase "nucleophilic alkyl halide" refers to any compound having an alkyl halide functional group on one part of the molecule and a nucleophilic group on the other part of the molecule. The term "nucleophilic" or "nucleophile" is well recognized in the art and refers to a chemical moiety having a reactive pair of electrons. Therefore, examples of a nucleophilic alkyl halide include, but not limited to 2-chloroacetamide, chloroacetic acid, chloroproprionic acid as well as those with the general formula:

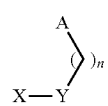

wherein A is a halo group and X is a nucleophile such as an —N—, —O— or —S— group.

The term "reduction" or "reducing" refers to the conversion of a functional group in a molecule from one oxidation state to a lower oxidation state. The term "reducing agent"

or "reductive agent" refers to any compound or complex that is known in the field for its effects in converting a functional group in a molecule from one oxidation state to a lower oxidation state. The reduction may be achieved via a direct electron, hydride or hydrogen-atom transfer. Typical reducing agents useful for Methods 1C include metal hydrides (e.g., lithium aluminum hydride, sodium borohydride, sodium cyanoborohydride) and hydrogen in the presence of a catalyst (e.g., Raney nickel, palladium on charcoal, nickel boride, platinum metal or its oxide, rhodium, ruthenium and zinc oxide, pentacyanocobaltate(II) $Co(CN)_5^{3-}$). Catalytic hydrogenation is typically carried out at room temperature and above atmospheric pressure, but higher temperature and pressure may be required for more resistant double bonds. Other reducing agents useful for converting double bonds to single bonds include silane and acid; sodium cyanoborohydride and acid; zinc and acid; sodium and liquid ammonia; sodium in ethanol; and borane-triethylamine. Typical reducing agents useful for reducing a ketone to a methylene as in Methods 1H include but are not limited to metal hydrides (e.g., diisobutyl aluminum hydride (DIBAL), sodium bis(2-methoxyethoxy)aluminum hydride (Red-Al) or sodium cyanoborohydride); boranes (e.g., $BH_3$-THF); or organoboranes (e.g. bis(benzyloxy)borane). Alternatively, such conversion may also be accomplished through catalytic hydrogenation by using hydrogen in presence of a catalyst (e.g. nickel, palladium on charcoal, nickel boride, platinum metal, platinum oxide, palladium oxide, rhodium oxide, ruthenium oxide or zinc oxide); Wolff-Kishner reduction by heating the ketone with hydrazine hydrate in the presence of a base such as sodium or potassium hydroxide (See Todd, Org. React. 4, 378-422 (1948)); or Clemmensen reduction by heating the ketone with zinc amalgam and aqueous mineral acid such as hydrochloric acid (See Vedejs, Org. React. 22, 401-422 (1975)). Other reagents that may also accomplish such reduction include triisopropyl phosphate, copper in the presence of sulfuric acid and tin in the presence of hydrochloric acid. For further examples of reducing agents, see "Advanced Organic Chemistry: Reactions, Mechanisms, and Structure" by Jerry March, p. 771-790, John Wiley & Sons, Inc. (Fourth Edition).

The term "alkylation" refers to the introduction of an alkyl radical onto an organic compound by substitution or addition. Therefore, the term "N-alkylation" refers to the introduction of an alkyl radical onto the nitrogen atom of the organic compound.

EXAMPLES

The compounds of the present invention can be produced through the following reaction scheme:

Example 1: Production of 6-bromo-2,3,4,5-tetrahydro-1H-pyrido[4,3-b]indole hydrochloric Acid Salt. [Int-1]

6-bromo-2,3,4,5-tetrahydro-1H-pyrido[4,3-b] indole hydrochloric acid salt may be prepared by mixing (2-bromophenyl) hydrazine hydrochloride (50.0 g, 219 mmol), 4-piperidone monohydrate hydrochloride (36.0 g, 230 mmol), ethanol (500 ml) and hydrochloric acid (50 ml). The resulting mixture is heated to reflux for 6 hours and is cooled to room temperature, filtered, washed with ethanol and dried to a solid.

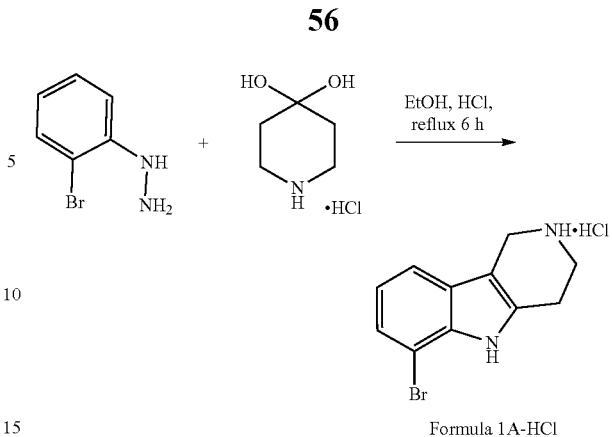

Formula 1A-HCl

Example 2: Production of [4 aS, 9bR]-6-bromo-2,3,4,4a,5,9b-hexahydro-1H-pyrido[4,3-b]indole

[4aS, 9bR]-6-bromo-2,3,4,4a,5,9b-hexahydro-1H-pyrido[4,3-b]indole may be prepared by mixing 6-bromo-2,3,4,5-tetrahydro-1H-pyrido[4,3-b]indole hydrochloric acid salt with trifluoracetic acid (630 ml, 8.48 mmol) and triethylsilane (172 ml). The mixture is stirred at room temperature under nitrogen for 19 hours. Excess trifluoroacetic acid and triethylsilane are removed in vacuo. Hexanes (550 ml) are added to the remaining oil and stirred at room temperature for 1 hour; the hexanes are decanted. An additional 250 ml of hexanes are added, stirred for 1 hour and decanted. 2N sodium hydroxide is added to the remaining oil until the pH=10 and then is extracted with dichloromethane. The organic layers are combined and washed with brine and dried ($Na_2SO_4$).

Enantiomeric separation of [4aS, 9bR]-6-bromo-2,3,4,4a,5,9b-hexahydro-1H-pyrido[4,3-b]indole may be carried out by dissolving racemate 6-bromo-2,3,4,4a,5,9b-hexahydro-1H-pyrido[4,3-b]indole (8 g, 31.6 mmol) in methanol (160 mL) at 50° C. (oil bath) and adding (R)-mandelic acid (4.8 g, 31.6 mmol) in portions. The resulting clear solution is stirred at 50° C. for several minutes and ether (80 mL) is added dropwise. The resulting solution is cooled to room temperature and the white precipitate (R-Mandelate sale, 3.7 g) is filtered off. HPLC analysis shows >99%ee. The filtrate is concentrated, treated with 1 N sodium hydroxyide (100 mL) and is extracted twice with dichloromenthane (2×50 mL). The dichloromethane layers are combined, washed with brine (2×200 mL) and dried with sodium sulphate. The dichoromethane solution is concentrated to an oil (5.59 g) and is redissolved in methanol (90 mL) at 50° C. (S)–(+)–mandelic acid (3.53 g, 23.2 mmol) is added in portions. The resulting clear solution is stirred at 50° C. for several minutes and ether (45 mL) is added dropwise. The resulting solution is cooled to room temperature and the white precipitate (S-Mandelate salt, 4.19 g) is filtered off HPLC analysis shows >99%ee. R-Mandelate: $[\alpha]_D^{25}=-98.1$, S-Mandelate: $[\alpha]_D^{25}=+102$, solvent: DMSO. Alternatively, the resolution may be carried out in a mixture of methanol and t-butylmethylether (MTBE).

Alternatively, [4aS, 9bR]-6-bromo-2,3,4,4a,5,9b-hexahydro-1H-pyrido[4,3-b]indole may be separated by dissolving racemate 6-bromo-2,3,4,4a,5,9b-hexahydro-1H-pyrido[4,3-b]indole (9.61 g, 38.0 mmol) in methanol (190 mL) at 50° C. and adding (S)-(+)-Mandelic acid (5.78 g, 38.0 mmol) in portions. The resulting clear solution is stirred at 50° C. for several minutes and ether (95 mL) is added dropwise. The resulting solution is cooled to room temperature. The white precipitate (S-Mandelate salt, 4.1 g) is filtered off. HPLC analysis shows >99% ee.

Enantiomeric separation of [4aS, 9bR]-6-bromo-2,3,4,4a,5,9b-hexahydro-1H-pyrido[4,3-b]indole may also be carried out by dissolving Racemic 6-bromo-2,3,4,4a,5,9b-hexahydro-1H-pyrido[4,3-b]indole (1710 gm "as is," 1570 gm by theory, 6.21 mol) in methanol (24 l) by warming to 40-50° C. (under nitrogen). To the mixture is added (R)-(−)-Mandelic acid (944 g, 6.2 mol) in one portion. The power to the heating mantle is turned-off and MTBE (13 L) is charged to the mixture. The resulting solution is allowed to cool to room temperature with stirring and aged for 30-40 hours at 15-25° C. with stirring. The product is isolated by filtration as a white to off-white precipitate and allowed to air dry at ambient temperature overnight. This affords 580 gm (23%) of the Int-2 R-Mandelate salt. Chiral HPLC analysis shows the undesired slower moving enantiomer is present as a single peak (>99% ee).

The filtrate is concentrated, diluted with water (25 L), stirred and treated with 50% NaOH (800 ml) to a pH of ~14 as measured by pH paper. The free base is extracted with dichloromethane (2×17 L and 1×6 L). The DCM layers are combined, dried (Na$_2$SO$_4$) and concentrated to afford a solid free base (~1150 g). The free base is dissolved in methanol (17 L) by warming to 40-50° C. under N$_2$ and (S)-(+)-Mandelic acid (692 g, 4.55 mol) is added. The heating mantle is turned off and to the solution is added MTBE (8.5 L) in one portion. The resulting solution is allowed to cool to room temperature and aged for 30-40 hours. The product is isolated by filtration as a white to off-white precipitate and air dried at ambient temperature overnight. This afforded 828 gm (33%) of S-Mandelate salt. Chiral HPLC analysis showed the faster moving enantiomer is present (>99% ee) with two other impurities present at ~1% each (which elute just before the undesired enantiomer). R-Mandelate: $[\alpha]_D^{25}=-98.1$, S-Mandelate: $[\alpha]_D^{25}=+102$, solvent:DMSO (about 10 mg in 3 ml DMSO). Chiral HPLC conditions: ChiralPak AD-H, 250×4.6 mm, 30% IPA in hexanes containing 0.1% diethylamine, flow 0.8 ml/min, UV detection at 254 nm. Samples are prepared by sonicating the salt in IPA.

Alternative to chiral resolution, enantiomeric separation of [4aS, 9bR]-6-bromo-2,3,4,4a,5,9b-hexahydro-1H-pyrido [4,3-b]indole may also be achieved by preparative chromatography using CHIRALPAK® AD® column, 20 μm, 5 cm id ×50 cm L. 26.4 g, 23.0 g and 14.8 g of racemic 6-bromo-2,3,4,4a,5,9b-hexahydro-1H-pyrido[4,3-b]indole are dissolved separately in 100% ethanol with stirring (optionally with low heating) and then filtered through a 0.4 μm filter. The feeds are injected separately at 25 mL volume and eluted with 100% Ethanol at a flow rate of 150 mL/min at 25° C. Alternatively, 420 g of racemic 6-bromo-2,3,4,4a,5,9b-hexahydro-1H-pyrido[4,3-b]indole is similarly dissolved, filtered and injected at 55 mL volumn onto a CHIRALPAK® AD® column, 20 μm, 11 cm ID ×25 cm L with a flow rate of 400 mL/min. The products are detected at an ultraviolet wavelength of 330 nm. The products are collected and the solvents are evaporated on rotary evaporators at 40° C. and under a vacuum of 50-70 mbar. The products are analyzed through chiral HPLC analysis by using an AD-H 4.6 mm ID ×250 mm column at 30° C. column temperature, 100% ethanol mobile phase at a flow rate of 0.7 mL/min and dected at 200 nm, 230 nm, 250 nm, 280 nm or 325 nm. The products are also analyzed by achiral HPLC analysis using an Eclipse, 5 μm XDB-C8, 4.6 mm ID ×250 mm column at 30° C. column temperature, 75:25 methanol/0.1% aqueous diethylamine at a flow rate of 1 mL/min and detected at 250 nm, 200 nm, 230 nm, 280 nm or 325 nm. The isolated product is >98% ee.

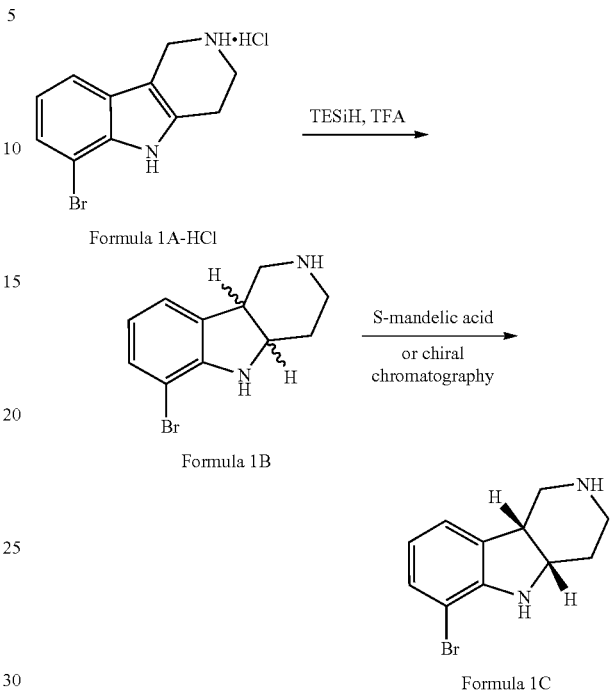

Formula 1A-HCl

Formula 1B

Formula 1C

Example 3: Production of (4aS,9bR)-ethyl 6-bromo-3,4,4a,5-tetrahydro-1H-pyrido [4,3-b]indole-2(9bH)-carboxylate (4aS,9bR)-ethyl 6-bromo-3,4,4a,5-tetrahydro-1H-pyrido [4,3-b]indole-2(9bH)-carboxylate may be prepared by first obtaining [4aS, 9bR]-6-bromo-2,3,4,4a, 5,9b-hexahydro-1H-pyrido[4,3-b]indole (36.0 g, 0.142 mol)) as a free base by using 50% aqueous sodium hydroxide solution and extracting the product into MTBE. The conversion to (4aS, 9bR)-ethyl 6-bromo-3,4,4a,5-tetrahydro-1H-pyrido[4,3-b] indole-2(9bH)-carboxylate may then be done by cooling a suspension of compounds of [4aS, 9bR]-6-bromo-2,3,4,4a, 5,9b-hexahydro-1H-pyrido[4,3-b]indole (36.0 g, 0.142 mol)) in THF (300 ml) and triethylamine (24 ml) in an ice-water bath. Ethyl chloroformate is added dropwise (13.5 ml, 0.142 mol) via a syringe pump over 1 hour. The ice-water bath is removed and the reaction mixture is stirred at room temperature for another hour. The reaction mixture is passed through a pad of celite and the solvent is evaporated to give (4aS,9bR)-ethyl 6-bromo-3,4,4a,5-tetrahydro-1H-pyrido[4,3-b]indole-2(9bH)-carboxylate). $^1$H NMR (CDCl$_3$, 300 MHz): 1.20-1.35 (m,3H), 1.73-1.85 (m, 1H), 1.85-1.99 (m, 1H), 3.22-3.52 (m, 3H), 3.52-3.66 (m, 1H), 3.66-3.95 (Br, 1H), 3.95-4.21 (m, 4H), 6.60 (t, J=7.7 Hz, 1H), 7.04 (d, J=7.2 Hz, 1H), 7.20 (d, J=8.1 Hz, 1H).

Alternative to the use of [4aS, 9bR]-6-bromo-2,3,4,4a,5, 9b-hexahydro-1H-pyrido[4,3-b]indole (Compound of Formula 1C) free base, the reaction may also be done by starting with the (S)-mandelate salt of [4aS, 9bR]-6-bromo-2,3,4,4a, 5,9b-hexahydro-1H-pyrido[4,3-b]indole. A 100 mL round-bottomed flask is equipped with a magnetic stirring bar, a pressure-equalizing addition funnel, and a N$_2$ inlet on top of the addition funnel. The flask is charged with the S-mandelate starting material (5 g, 12.35 mmol), Na₂CO₃ (2.88 g, 27.17 mmol), and 25 mL of THF. To the yellow reaction mixture at 25° C. (heating block temperature) is added a solution of ethyl chloroformate (1.64 g, 15.11 mmol) in 5 mL of THF dropwise over ca 70 minutes. The batch is stirred at 25° C. for another 10 min, and is checked by HPLC. Less than 2% of the starting material is observed by HPLC, and the desired product is registered at ca. 98%. To the batch is added 12.5 mL of EtOH, and the batch is concentrated under reduced pressure to remove ca. 30 mL of solvent (mostly THF). To the batch is then added 37.5 mL of H₂O, and the resultant mixture shows pH >9 by pH paper. The yellow mixture is then stirred at rt for ca. 1 h, and is filtered. The solid is rinsed with 25 mL of H₂O. After drying in a vacuum oven at 58° C. for ca. 16 h, 3.9442 g of a yellow solid is obtained (98% yield). ¹H NMR of the solid conformed, and showed no (s)-mandelic acid. HPLC analysis of the product shows the desired product at >99% purity. LC-MS showed a peak with M/e=326 (M+1).

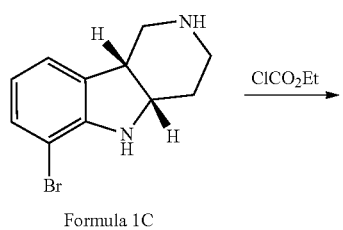

Formula 1C

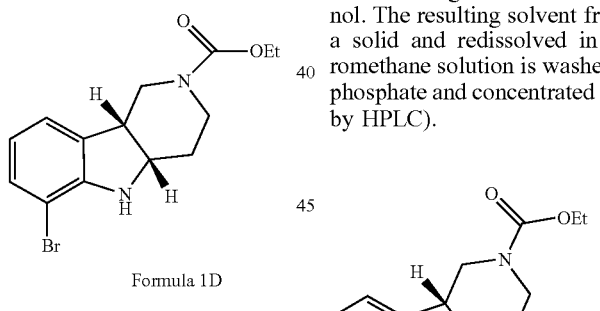

Formula 1D

Example 4: Production of [4aS,9bR]-ethyl 5-(2-amino-2-oxoethyl)-6-bromo-3,4,4a, 5-tetrahydro4H-pyrido[4,3-b]indole-2(9bH)-carboxylate (4aS,9bR)-ethyl 5-(2-amino-2-oxoethyl)-6-bromo-3,4,4a, 5-tetrahydro-1H-pyrido[4,3-b]indole-2(9bH)-carboxylate may be prepared by heating to a reflux a suspension of (4aS,9bR)-ethyl 6-bromo-3,4,4a,5-tetrahydro-1H-pyrido[4, 3-b]indole-2(9bH)-carboxylate (5.648 g, 17.4 mmol), 2-chloroacetamide (7.32 g, 78.2 mmol), potassium iodide (19.2 g, 77.7mol) and diisopropylethylamine (19 mL, 115 mmol) in acetonitrile (80 mL) for 27 hours. The solvent is removed in a vacuo and water (200 mL) is added to the residue and stirred for 1 hour. The resulting white solid is filtered off, washed with ethanol and dried.

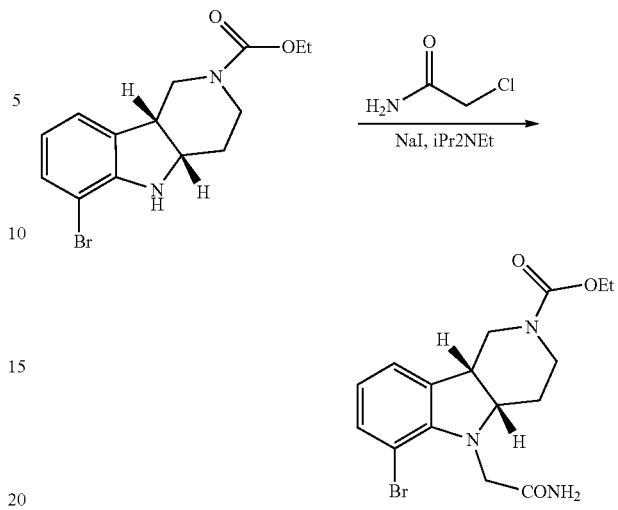

Example 5: Production of (6bR,10aS)-ethyl 2,3,6b, 9,10,10a-hexahydro-2-oxo-1H-pyrido[3',4':4,5]-pyrrolo[1,2,3-de]quinoxaline-8-carboxylate A suspension of [4aS,9bR]-ethyl 5-(2-amino-2-oxoethyl)-6-bromo-3,4,4a, 5-tetrahydro-1H-pyrido[4,3-b]indole-2 (9bH)-carboxylate (254 mg, 1.34 mmol), cuprous iodide (254 mg, 1.34 mol), potassium carbonate (3.96 g, 28.7 mmol) and N,N'-dimethylethylenediamine (0.31 mL, 2.87 mmol) in dioxiane (20 mL) is heated at reflux for 4.5 hours. Another portion of cuprous iodide (250 mg, 1.32 mmol) and N,N'-dimethylethylenediamine (0.33 mL, 3.05 mmol) is added. The resulting mixture is heated to a reflux for another 3 hours and then at 73° C. for about 66 hours. The reaction mixture is concentrated and passed through a short alumina column using 100:3:3 dichloromethan:triethylamine:methanol. The resulting solvent from the column is evaporated to a solid and redissolved in dichloromethane. The dichloromethane solution is washed with brine, dried with sodium phosphate and concentrated to a solid (3.7 g, 95%, 83% pure by HPLC).

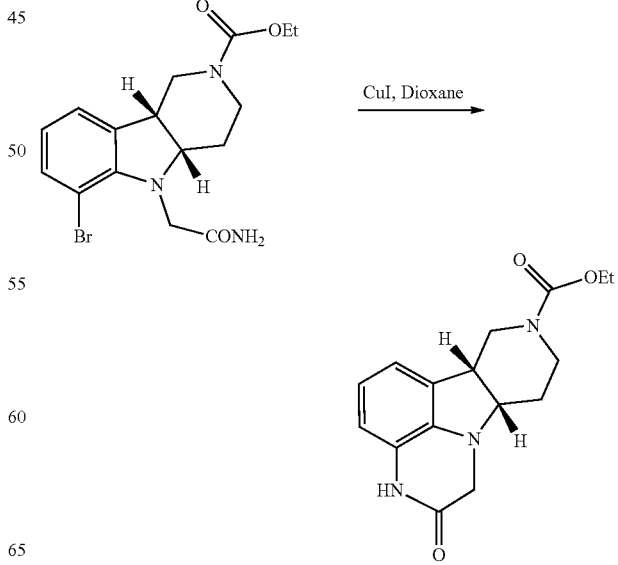

Example 5-A: Production of (6bR,10aS)-ethyl 2,3,6b,9,10,10a-hexahydro-2-oxo-1H-pyrido[3',4':4,5]-pyrrolo[1,2,3-de]quinoxaline-8-carboxylate Alternative to Example 5 above, (6bR,10aS)-ethyl 3,6b,9,10,10a-hexahydro-3-methyl-2-oxo-1H-pyrido[3',4':4,5]-pyrrolo[1,2,3-de]quinoxaline-8-carboxylate may also be made in a one pot method starting from Compound of Formula 1D. A 2 liter 4 neck round bottom flask is equipped with a mechanical stirrer, reflux condenser, $N_2$ inlet, teflon covered K-type temperature probe with a controller, and a heating mantle. To the flask is charged (4aS,9bR)-ethyl 6-bromo-3,4,4a,5-tetrahydro-1H-pyrido[4,3-b]indole-2(9bH)-carboxylate (250 g, 769 mmol), chloroacetamide (124 g, 1153 mmol, 1.5 equiv), potassium iodide (191.5 g, 1160 mmol, 1.5 equiv), diisopropyl ethylamine (266 mL, 1531 mmol, 2.0 equiv), and dioxane (625 mL). The reaction is heated to reflux temperature of about 103° C. until less than 3% of the starting substrate is observed by HPLC (about 48 hours). Additional charge of N-methyl chloroacetamide and diisopropyl ethylamine maybe necessary. The reaction is then cooled to ca. 80° C., and at this temperature copper iodide (29.2 g, 153.8 mmol, 0.2 equiv), potassium carbonate (232.5 g, 1682 mmol, 2.2 equiv), dimethylethylene diamine (49.6 mL, 461 mmol, 0.6 equiv), and additional dioxane (375 mL) is added. The reaction is then re-heated to reflux and is monitored by HPLC. Reflux occurs at ca. 103° C. The reaction is monitored by HPLC.

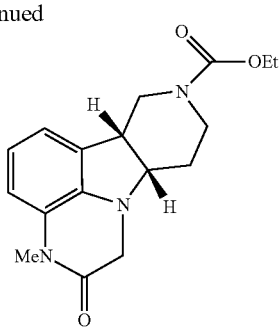

$C_{17}H_{21}N_2O_2 = 316.37$
Chiral Int-4

Example 6: Production of (6bR,10aS)-ethyl 3,6b,9,10,10a-hexahydro-3-methyl-2-oxo-1H-pyrido[3',4':4,5]-pyrrolo[1,2,3-de]quinoxaline-8-carboxylate (6bR,10aS)-ethyl 2,3,6b,9,10,10a-hexahydro-2-oxo-1H-pyrido-[3', 4':4,5]-pyrrolo[1,2,3-de]quinoxaline-8-carboxylate (17.3 g, 57.4 mmol), $K_2CO_3$ (15.8 g, 114 mmol), and methyl iodide (66 ml, 1060 mmol) are placed in a 2 L pressure bottle and 500 ml of acetone is added. The bottle is heated in an oil bath at 109° C. for 5.5 hours and cooled to room temperature. Acetone and excess methyl iodide are removed in vacuo and 200 ml of water is added and then extracted with DCM. The DCM layers are combined and washed with brine and dried ($Na_2SO_4$). Evaporation of the solvent results in (6bR,10aS)-ethyl 2,3,6b,9,10,10a-hexahydro-3-methyl-2-oxo-1H-pyrido [3',4':4,5]-pyrrolo [1,2,3-de]quinoxaline-8-carboxylate.

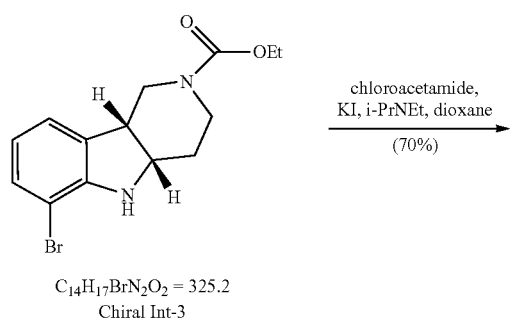

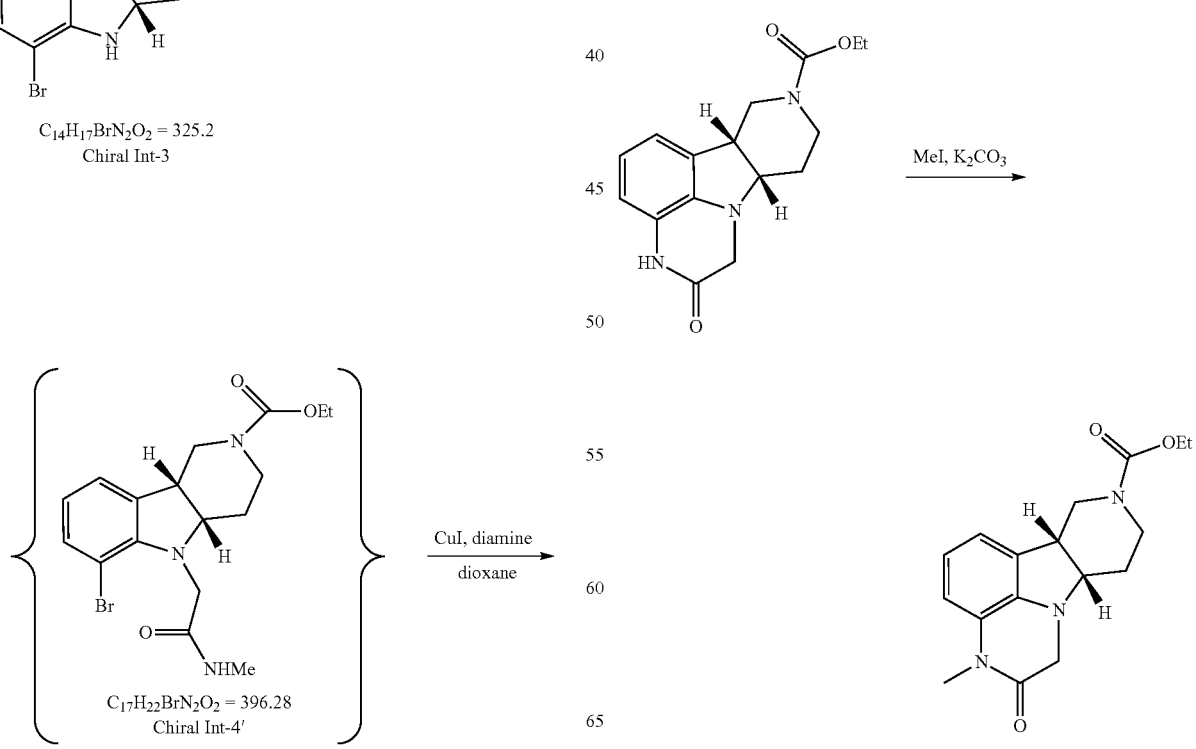

Example 6-A: Production of (6bR,10aS)-ethyl 2,3,6b,9,10,10a-hexahydro-3-methyl-2-oxo-1H-pyrido[3',4':4,5]-pyrrolo[1,2,3-de]quinoxaline-8-carboxylate Alternative to Example 6 above, (6bR,10aS)-ethyl 3,6b,9,10,10a-hexahydro-3-methyl-2-oxo-1 H-pyrido [3 ',4':4,5]-pyrrolo [1,2,3-de]quinoxaline-8-carboxylate may also be made in a one pot method starting from Compound of Formula 1D. A 2 liter 4 neck round bottom flask is equipped with a mechanical stirrer, reflux condenser, N₂ inlet, teflon covered K-type temperature probe with a controller, and a heating mantle. To the flask is charged (4aS,9bR)-ethyl 6-bromo-3,4,4a,5-tetrahydro-1H-pyrido[4,3-b]indole-2(9bH)-carboxylate (250 g, 769 mmol), N-methyl chloroacetamide (124 g, 1153 mmol, 1.5 equiv), potassium iodide (191.5 g, 1160 mmol, 1.5 equiv), diisopropyl ethylamine (266 mL, 1531 mmol, 2.0 equiv), and dioxane (625 mL). The reaction is heated to reflux temperature of about 103° C. until less than 3% of the starting substrate is observed by HPLC (about 48 hours). Additional charge of N-methyl chloroacetamide and diisopropyl ethylamine maybe necessary. The reaction is then cooled to ca. 80° C., and at this temperature copper iodide (29.2 g, 153.8 mmol, 0.2 equiv), potassium carbonate (232.5 g, 1682 mmol, 2.2 equiv), dimethylethylene diamine (49.6 mL, 461 mmol, 0.6 equiv), and additional dioxane (375 mL) is added. The reaction is then re-heated to reflux and is monitored by HPLC. Reflux occurs at ca. 103° C. The reaction is monitored by HPLC.

When complete, the reaction is cooled to ca. 40° C. and poured onto a plug of flash-grade silica gel (625 g, 2.5 g/g). It is eluted (under vacuum) with 6.25 L of ethyl acetate. The eluent is concentrated to a solid residue (320 gm), and then is dissolved in hot ethanol (800 ml). This mixture is allowed to cool to ambient temperature and stirred overnight. The next day it is cooled to 0-5° C., aged for 1 h and filtered. The cake is washed with cold ethanol (150 ml) and allowed to air dry to afford 170 grams (70%) of product as a white solid which is >99A% pure by HPLC. HPLC 10:90 to 90:10 CH₃CN:H₂O over 15 min. Hold at 90:10 for 2 min, 0.025% TFA Buffer, 1.5 mL/min, UV at 220 nm, Phenomenex Jupiter C18 column 4.6 mm×250 mm. The product is 75A % pure by LC/MS in the total ion chromatogram. ¹H-NMR (300 MHz, CDCl₃) 1.28(t, J=6.9 Hz, 3 H), 1.86-1.96(m, 2 H), 2.72(br, 1H), 3.09-3.48(m, 7H), 3.86-4.21(m, 5H), 6.75 (dd, J=1.2, 7.8 Hz, 1 H), 6.82(t, J=7.8 Hz, 1 H), 6.90(dd, J=1.2, 7.2 Hz, 1 H).

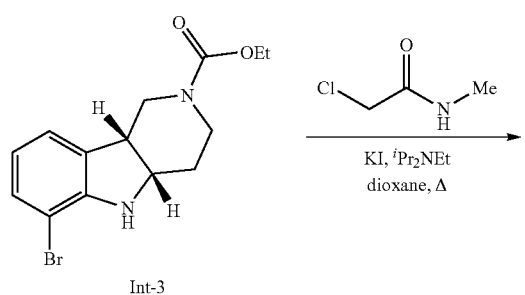

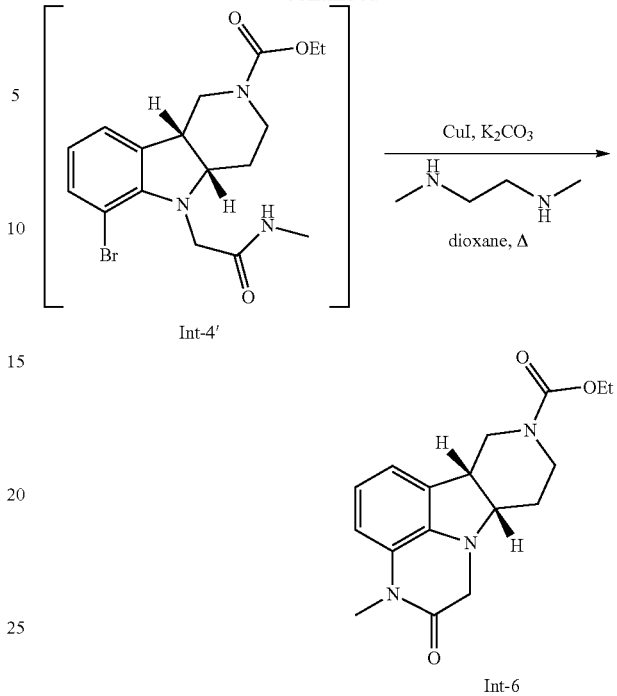

Example 7: Production of (6bR,10aS)-3-methyl-2,3,6b,9,10,10a-hexahydro-1H-pyrido-[3',4':4,5]-pyrrolo[1,2,3-de]quinoxaline-8-carboxylate (6bR,10aS)-ethyl 2,3,6b,9,10,10a-hexahydro-3-methyl-1H-pyrido-[3',4':4,5]-pyrrolo[1,2,3-de]quinoxaline-8-carboxylate may be prepared by adding BH₃THF (1 M in THF, 143 mL, 143 mmol) dropwise at room temperature over 15 minutes to a suspension of (6bR,10aS)-ethyl 2,3,6b,9,10,10a-hexahydro-3 -methyl-2-oxo-1H-pyrido[3',4':4,5]-pyrrolo[1,2,3-de]quinoxaline-8-carboxylate (18.0 g, ca.57 mmol) in 50 ml of THF. The resulting mixture is heated to a reflux for 3 hours. The reaction mixture is cooled in an ice-water bath and 150 ml of 6N HCl is added dropwise. After THF is removed in vacuo, 2N NaOH is added until pH=9 followed by extraction with 500 ml of DCM. The DCM layer is washed with brine and dried over Na₂SO₄. Evaporation of the solvent yields crude (6bR,10aS)-ethyl 2,3,6b,9,10,10a-hexahydro-3-methyl-1H-pyrido-[3',4':4,5]-pyrrolo[1,2,3-de]-quinoxaline-8-carboxylate.

Alternatively, (6bR,10aS)-3-methyl-2,3,6b,9,10,10a-hexahydro-1H-pyrido-[3',4':4,5]-pyrrolo[1,2,3-de]quinoxaline may be prepared as follows: To a 5 L, 3-necked round-bottomed flask equipped with an overhead stirrer, an N₂ inlet, and a K-type Teflon covered temperature probe is charged with (6bR,10aS)-ethyl 2,3,6b,9,10,10a-hexahydro-3-methyl-2-oxo-1H-pyrido [3',4':4,5]-pyrrolo[1,2,3-de]quinoxaline-8-carboxylate (218 g, 691.3 mmol) using THF (ca. 50 mL). The reaction vessel is vacuum/N₂ purged three times, and then is added a 1 M solution of BH₃-THF complex in THF (1962 mL, 1962 mmol, 2.8 equiv) slowly through an addition funnel. The resultant clear solution is then heated at 60° C. The resultant batch is then stirred at 60° C. for ca. 17 h, and showed 89.0% of the desired product with ca. 3.0% of unreacted substrate by HPLC. The batch is stirred at 60° C. for another 3 h, and then is cooled in an ice bath to ca. 10° C. To the batch is added MeOH (327 mL, 8073 mmol, 11.7 equiv) slowly through an addition funnel while keeping the internal temperature below 25° C. The resultant batch is stirred in the ice bath for ca. 30 min, and is concentrated in vacuo to afford a yellow paste. The crude paste is then partitioned between EtOAc (2180 mL) and H$_2$O (2180 mL). The separated organic layer is dried (Na$_2$SO$_4$), filtered, and concentrated under reduced pressure to afford 227.6 g of a yellow liquid. HPLC analysis of the liquid showed 89% of the desired product with 2.6% of an impurity at RRt 0.62 and 2.5% of the starting material. $^1$H NMR (CDCl$_3$, 300 MHz) δ 1.28 (t, J=7.0 Hz, 3H), 1.79-1.95 (m, 2H), 2.74-2.92 (m, 5H), 3.02-3.22 (m, 2H), 3.22-3.38 (m, 3H), 3.54-3.64 (m, 1H), 3.78-4.24 (m, 4H), 6.41(d, J=7.8 Hz, 1H), 6.54 (d, J=7.2 Hz, 1H), 6.66 (t, J=7.7 Hz, 1H); $^{13}$C-NMR (CDCl$_3$, 75 MHz) δ 14.9, 24.7, 37.7, 39.9, 41.4, 44.4, 45.8, 50.7, 61.4, 65.0, 109.3, 113.3, 120.6, 128.8, 135.1, 138.2, 155.6.

taining the internal temperature below 30° C. The aqueous layer shows pH>14 after the addition of NaOH solution. To the batch is then added EtOAc (1090 mL), and the resultant dark mixture is stirred in ice bath for ca. 5 min. Layers are separated, and the aqueous layer is extracted with EtOAc (1090 mL). The combined organic layers are washed with brined (1090 mL), filtered, and concentrated under reduced pressure to afford 166.8 g of a dark brown liquid (theoretical yield 158.5 g). HPLC analysis of the liquid showed 88.1% of the desired product. $^1$H NMR of the product conforms and shows no single impurity over 5%. LC-MS analysis shows ca. 93% of a major peak with M/e=230 (M+1). The product is stored under N$_2$ in the cold room. $^1$H NMR (CDCl$_3$, 300 MHz) δ 1.71-1.97 (m, 2H), 2.58-2.70 (m, 1H), 2.80-2.92 (m, 6H), 2.98-3.12 (m, 2H), 3.26-3.37 (m, 3H), 3.55-3.64 (m, 1H), 6.41 (d, J=7.8 Hz, 1H), 6.51 (d, J=7.2 Hz, 1H), 6.65 (t, J=7.8 Hz, 1H).

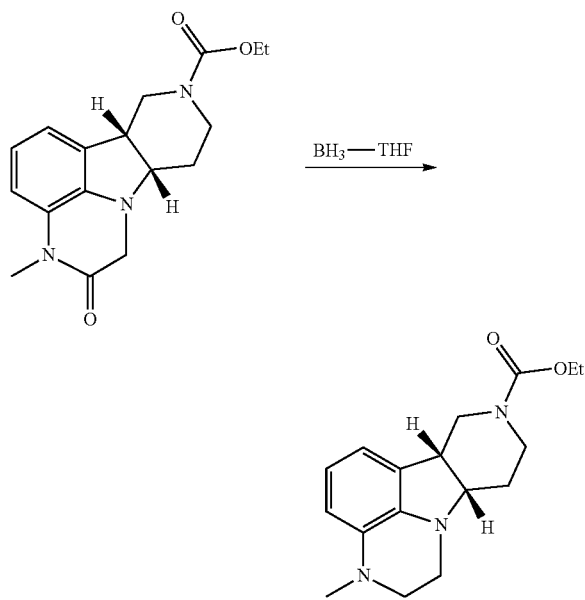

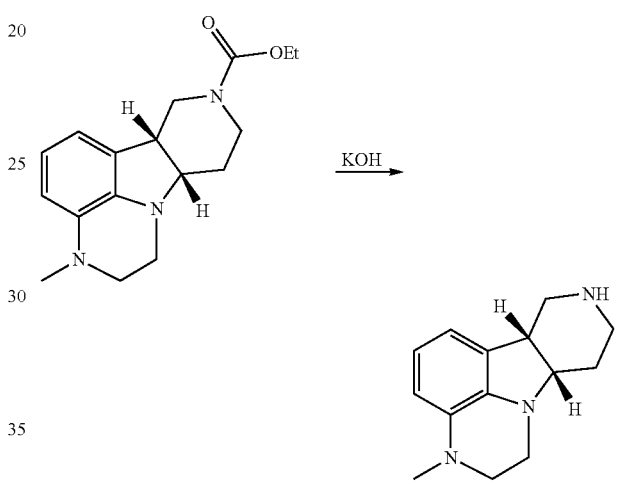

Example 8: Production of (6bR,10aS)-3-methyl-2,3,6b,9,10,10a-hexahydro-1H-pyrido-[3',4':4,5]-pyrrolo[1,2,3-de]quinoxaline (6bR,10aS)-3-methyl-2,3,6b,9,10,10a-hexahydro-1H-pyrido-[3',4':4,5]-pyrrolo[1,2,3-de]quinoxaline-8-carboxylate (ca. 18.5 g, 57 mmol), KOH (12.7 g, 226 mmol) and n-butanol are placed in a 300 ml pressure bottle and heated in an oil bath at 120° C. for 3 hours. n-butanol is removed in vacuo and 300 ml of water is added and then extracted with DCM. The DCM layers are combined and washed with brine and dried (Na$_2$SO$_4$). Evaporation of the solvent gives (6bR,10aS)-ethyl-3-methyl-2,3,6b,7,8,9,10,10a-octahydro-1H-pyrido-[3',4':4,5]-pyrrolo [1,2,3 -de]quinoxaline.

Alternatively, to a 5-L, 3-necked, round bottomed flask, and the remaining Int-7 is dissolved crude in conc. HCl (1090 mL) before it is added (6bR,10aS)-3-methyl-2,3,6b,9,10,10a-hexahydro-1H-pyrido-[3',4':4,5]-pyrrolo [1,2,3-de]quinoxaline-8-carboxylate to the 5 L reaction vessel. The resultant solution is heated at 95° C. for 15 h. The batch is then cooled in an ice bath to ca. 10° C., and is added MTBE (1090 mL). To the batch is then added 25% NaOH solution (1308 mL) slowly through an addition funnel while main- Example 9: Production of 4-((6bR,10aS)-3-methyl-2,3,6b,9,10,10a-hexahydro-1H-pyrido-[3',4':4,5]-pyrrolo[1,2,3-de]quinoxalin-8-(7H)-yl)-1-(4-fluorophenyl)-1-butanone A suspension of (6bR,10aS)-3-methyl-2,3,6b,9,10,10a-hexahydro-1H-pyrido-[3',4':4,5]-pyrrolo[1,2,3-de]quinoxaline (ca. 11.8 g, ca.50 mmol), 4-chloro-4'-flurobutyrophenone (15.0 g, 74.8 mmol), triethylamine (30 mL, 214 mmol), and potassium iodide (12.6 g, 76 mmol) in dioxane (65 ml) and toluene (65 ml) is heated to reflux for 7 hours. After filtration and evaporation of the solvent, 200 ml of DCM is added. The DCM solution is washed with brine, dried (Na2SO4) and concentrated to approximately 55 ml. The concentrated solution is added dropwise to 600 ml of 0.5N HCl ether solution. The solid is filtered off and washed with ether and then dissolved in water. The resulting aqueous solution is basified with 2N NaOH and extracted with DCM. The DCM layers are combined, washed with brine (2×200 mL) and dried (Na$_2$SO$_4$). Evaporation of the solvent and chromatography of the residue over silica gel gives 4-((6bR,10aS)-3-methyl-2,3,6b,9,10,10a-hexahydro-1H-pyrido-[3',4':4,5]-pyrrolo[1,2,3-de]quinoxalin-8-(7H)-yl)-1-(4-fluorophenyl)-1-butanone.

Alternative to the use of dioxane, the reaction may be carried out in 3-pentanone. To a 5 L, three-necked, round-bottomed flask equipped with a mechanical stirrer, a N$_2$ inlet, a reflux condenser, and a temperature probe is charged with 230 g of (6bR,10aS)-3-methyl-2,3,6b,9,10,10a-hexahydro-1H-pyrido-[3',4':4,5]-pyrrolo[1,2,3-de]quinoxaline (1 mol), 249.78 g of KI (1.5 mol, 1.5 equiv), 194.12 g of ¹Pr₂NEt (1.5 mol, 1.5 equiv), 301.76 g of 4-chloro-4'-fluorobutyrophenone (1.5 mol, 1.5 equiv), and 2300 mL of 3-pentanone. The resultant mixture is then heated at 95° C. (internal temperature) for 17 h, and then is checked by HPLC for reaction completion. The batch is then cooled to ca. 10° C. with an ice bath, and then is added 5% NaOH solution (2300 mL). The separated aqueous layer is then extracted with EtOAc (2300 mL). The combined organic layer is filtered through a pad of silica gel (115 g) that is pre-packed with EtOAc. The silica gel is then flushed with EtOAc (2300 mL). The combined filtrate is concentrated under reduced pressure to afford a dark brown liquid. To the liquid is then added EtOAc (2300 mL), and is added 1.5 N HCl solution (2300 mL). The batch is stirred at rt for ca. 20 min, and layers are cut. The separated organic layer is extracted with 1.5 N HCl solution (1150 mL), and the layers are separated. The combined aqueous layer is cooled in an ice bath to ca. 10° C., and is added EtOAc (2300 mL). To the stirring mixture is then added 25% NaOH solution (1000 mL) through an addition funnel while maintaining the internal temperature under 25° C. The resultant mixture is stirred in an ice bath for ca. 20 min, and the layers are separated. The aqueous layer shows a pH between 11 to 12 by pH paper. The aqueous layer is back extracted with EtOAc (1150 mL), and the layers are cut. The combined organic layer is washed with brine (1150 mL), dried over Na₂SO₄ (230 g), filtered, and concentrated in vacuo to afford 368.8 g of a dark brown liquid. The crude free base is stored under N₂ in a dark cold room.

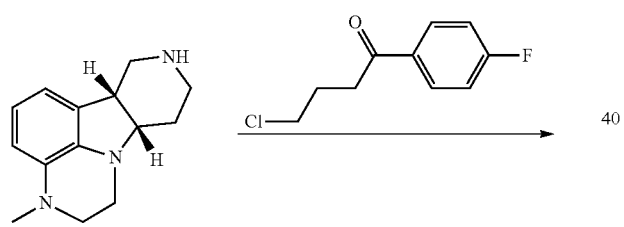

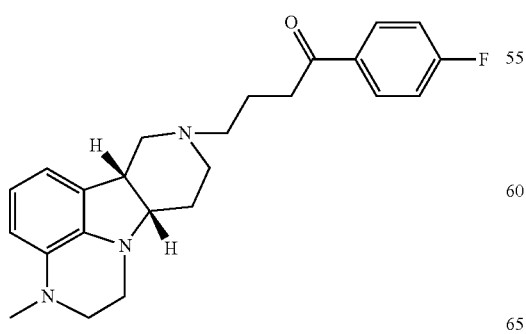

What is claimed is:

1. A process for preparing a compound of Formula 1J or Formula 2J:

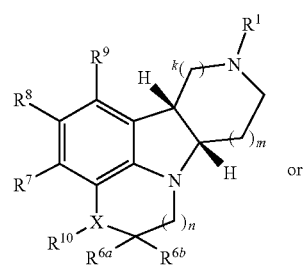

Formula 1J

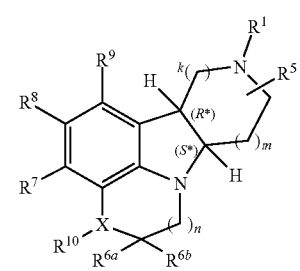

Formula 2J or a pharmaceutically acceptable salt form thereof, wherein:

$R^1$ is:

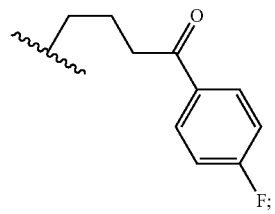 [SMILES: *CCCC(=O)c1ccc(F)cc1]

each $R^5$ is independently H;
$R^{6a}$ is H;
$R^{6b}$ is H;
$R^7$ is H;
$R^8$ is H;
$R^9$ is H;
X is N;
$R^{10}$ is $CH_3$;
k is 1;
m is 1; and
n is 1;

wherein the process comprises the following steps:
(1) N-alkylating the free base form of a compound of Formula 1I or Formula 2I:

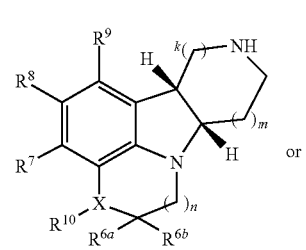

Formula 1I

-continued

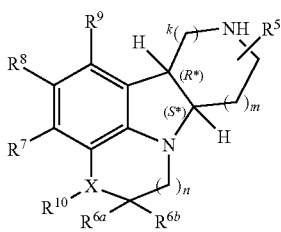

Formula 2I or a salt form thereof,
wherein:
  each $R^5$ is independently H;
  $R^{6a}$ is H;
  $R^{6b}$ is H;
  $R^7$ is H;
  $R^8$ is H;
  $R^9$ is H;
  X is N;
  $R^{10}$ is $CH_3$;
  k is 1;
  m is 1; and
  n is 1;
with a compound of the following formula:
  $G-Z-R^{13}$,
wherein:
G is

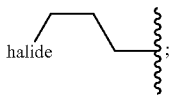

Z is —C(O)—; and
$R^{13}$ is

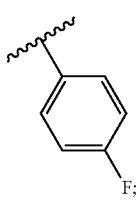 [SMILES: *c1ccc(F)cc1]

in the presence of a base selected from the group consisting of (a), (b), (c), (d), (e), (f), (g), (h), (i), (j), and (k):
(a) an amine base selected from the group consisting of ammonia, triethylamine, N,N'-diisopropylethylamine, 4-(dimethylamino)pyridine (DMAP), 1,5-diazabicyclo[4.3.0]non-5-ene (DBN), and 1,5-diazabicyclo[5.4.0]undec-5-ene (DBU);
(b) an alkali metal hydride selected from the group consisting of lithium hydride, sodium hydride, and potassium hydride;
(c) an alkali metal alkoxide selected from the group consisting of lithium tert-butoxide, sodium tert-butoxide, potassium tert-butoxide, NaOAr, and KOAr, wherein Ar is aryl;
(d) an alkali metal carbonate selected from the group consisting of lithium carbonate, sodium carbonate, potassium carbonate, and cesium carbonate;
(e) an alkaline earth metal carbonate selected from the group consisting of magnesium carbonate, calcium carbonate, and barium carbonate;
(f) an alkali metal bicarbonate selected from the group consisting of lithium bicarbonate, sodium bicarbonate, potassium bicarbonate, and cesium bicarbonate;
(g) an alkaline earth metal bicarbonate selected from the group consisting of magnesium bicarbonate, calcium bicarbonate, and barium bicarbonate;
(h) an alkali metal hydroxide selected from the group consisting of lithium hydroxide, sodium hydroxide, potassium hydroxide, and cesium hydroxide;
(i) an alkaline earth metal hydroxide selected from the group consisting of magnesium hydroxide, calcium hydroxide, and barium hydroxide;
(j) an alkali metal phosphate selected from the group consisting of lithium phosphate, sodium phosphate, potassium phosphate, and cesium phosphate; and
(k) an alkaline earth metal phosphate selected from the group consisting of magnesium phosphate, calcium phosphate, and barium phosphate;
to provide the compound of Formula 1J or Formula 2J above; and
(2) when the process provides a pharmaceutically acceptable salt form of the compound of Formula 1J or Formula 2J above, optionally reacting the free base form of the compound of Formula 1J or Formula 2J provided in step (1) above with an acid selected from the group consisting of acetic acid, phenylacetic acid, trifluoroacetic acid, ascorbic acid, benzoic acid, 2-acetoxybenzoic acid, citric acid, ethanedisulfonic acid, fumaric acid, glutamic acid, glycolic acid, hydrobromic acid, hydrochloric acid, isethionic acid, lactic acid, maleic acid, hydroxymaleic acid, malic acid, methanesulfonic acid, nitric acid, oxalic acid, pamoic acid, phosphoric acid, propionic acid, salicylic acid, stearic acid, succinic acid, sulfamic acid, sulfanilic acid, sulfuric acid, tartaric acid, and toluenesulfonic acid, in the presence of water or an organic solvent selected from the group consisting of 3-pentanone, dioxane, diethyl ether, ethanol, ethyl acetate, isopropanol, acetonitrile, and toluene, or a combination thereof, to provide a pharmaceutically acceptable salt form of the compound of Formula 1J or Formula 2J.

2. The process according to claim 1, wherein the compound of Formula 1I or Formula 2I is in the free base form.

3. The process according to claim 1, wherein the compound of Formula 1I or Formula 2I is in a salt form.

4. The process according to claim 1, wherein the compound of Formula 1I or Formula 2I is in a salt form selected from the group consisting of a hydrochloric acid salt form, a phosphoric acid salt form, a sulfuric acid salt form, and a trifluoracetic acid salt form.

5. The process according to claim 1, wherein the compound of Formula 1I or Formula 2I is in a hydrochloric acid salt form.

6. The process according to claim 1, wherein G is:

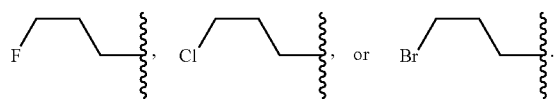

7. The process according to claim 1, wherein G is:

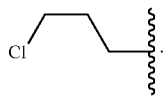

8. The process according to claim 1, wherein the base is selected from the group consisting of (a), (d), (e), (f), (g), (h), and (i):
  (a) an amine base selected from the group consisting of ammonia, triethylamine, N,N'-diisopropylethylamine, 4-(dimethylamino)pyridine (DMAP), 1,5-diazabicyclo[4.3.0]non-5-ene (DBN), and 1,5-diazabicyclo[5.4.0]undec-5-ene (DBU);
  (d) an alkali metal carbonate selected from the group consisting of lithium carbonate, sodium carbonate, potassium carbonate, and cesium carbonate;
  (e) an alkaline earth metal carbonate selected from the group consisting of magnesium carbonate, calcium carbonate, and barium carbonate;
  (f) an alkali metal bicarbonate selected from the group consisting of lithium bicarbonate, sodium bicarbonate, potassium bicarbonate, and cesium bicarbonate;
  (g) an alkaline earth metal bicarbonate selected from the group consisting of magnesium bicarbonate, calcium bicarbonate, and barium bicarbonate;
  (h) an alkali metal hydroxide selected from the group consisting of lithium hydroxide, sodium hydroxide, potassium hydroxide, and cesium hydroxide; and
  (i) an alkaline earth metal hydroxide selected from the group consisting of magnesium hydroxide, calcium hydroxide, and barium hydroxide.

9. The process according to claim 8, wherein the base is selected from the group consisting of (a), (d), (e), (f), (g), (h), and (i):
  (a) an amine base selected from the group consisting of ammonia, triethylamine, N,N'-diisopropylethylamine, 4-(dimethylamino)pyridine (DMAP), 1,5-diazabicyclo[4.3.0]non-5-ene (DBN), and 1,5-diazabicyclo[5.4.0]undec-5-ene (DBU);
  (d) an alkali metal carbonate selected from the group consisting of sodium carbonate, potassium carbonate, and cesium carbonate;
  (e) an alkaline earth metal carbonate selected from the group consisting of magnesium carbonate, calcium carbonate, and barium carbonate;
  (f) an alkali metal bicarbonate selected from the group consisting of sodium bicarbonate, potassium bicarbonate, and cesium bicarbonate;
  (g) an alkaline earth metal bicarbonate selected from the group consisting of magnesium bicarbonate, calcium bicarbonate, and barium bicarbonate;
  (h) an alkali metal hydroxide selected from the group consisting of sodium hydroxide, potassium hydroxide, and cesium hydroxide; and
  (i) an alkaline earth metal hydroxide selected from the group consisting of magnesium hydroxide, calcium hydroxide, and barium hydroxide.

10. The process according to claim 8, wherein the base is selected from the group consisting of (a) and (d):
  (a) triethylamine; and
  (d) cesium carbonate.

11. The process according to claim 1, wherein the base is an amine base selected from the group consisting of triethylamine, N,N'-diisopropylethylamine, 4-(dimethylamino)pyridine (DMAP), 1,5-diazabicyclo[4.3.0]non-5-ene (DBN), and 1,5-diazabicyclo[5.4.0]undec-5-ene (DBU).

12. The process according to claim 1, wherein the base is an alkali metal carbonate selected from the group consisting of lithium carbonate, sodium carbonate, potassium carbonate, and cesium carbonate or an alkali metal bicarbonate selected from the group consisting of lithium bicarbonate, sodium bicarbonate, potassium bicarbonate, and cesium bicarbonate.

13. The process according to claim 1, wherein the base is an alkali metal hydroxide selected from the group consisting of lithium hydroxide, sodium hydroxide, potassium hydroxide, and cesium hydroxide.

14. The process according to claim 1, wherein:
  (i) G is:

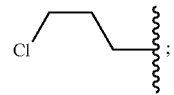

and
  (ii) the base is selected from the group consisting of (a) and (d):
  (a) triethylamine; and
  (d) cesium carbonate.

15. The process according to claim 1, wherein the process comprises reacting the free base form of the compound of Formula 1J or Formula 2J with an acid selected from the group consisting of acetic acid, phenylacetic acid, trifluoroacetic acid, ascorbic acid, benzoic acid, 2-acetoxybenzoic acid, citric acid, ethanedisulfonic acid, fumaric acid, glutamic acid, glycolic acid, hydrobromic acid, hydrochloric acid, isethionic acid, lactic acid, maleic acid, hydroxymaleic acid, malic acid, methanesulfonic acid, nitric acid, oxalic acid, pamoic acid, phosphoric acid, propionic acid, salicylic acid, stearic acid, succinic acid, sulfamic acid, sulfanilic acid, sulfuric acid, tartaric acid, and toluenesulfonic acid, in the presence of water or an organic solvent selected from the group consisting of diethyl ether, ethanol, ethyl acetate, isopropanol, and acetonitrile, or a combination thereof, to provide a pharmaceutically acceptable salt form of the compound of Formula 1J or Formula 2J.

16. The process according to claim 15, wherein the pharmaceutically acceptable salt form of the compound of Formula 1J or Formula 2J is the toluenesulfonic acid salt form.

17. The process according to claim 14, wherein the process comprises reacting the free base form of the compound of Formula 1J or Formula 2J with an acid selected from the group consisting of acetic acid, phenylacetic acid, trifluoroacetic acid, ascorbic acid, benzoic acid, 2-acetoxybenzoic acid, citric acid, ethanedisulfonic acid, fumaric acid, glutamic acid, glycolic acid, hydrobromic acid, hydrochloric acid, isethionic acid, lactic acid, maleic acid, hydroxymaleic acid, malic acid, methanesulfonic acid, nitric acid, oxalic acid, pamoic acid, phosphoric acid, propionic acid, salicylic acid, stearic acid, succinic acid, sulfamic acid, sulfanilic acid, sulfuric acid, tartaric acid, and toluenesulfonic acid, in the presence of water or an organic solvent selected from the group consisting of diethyl ether, ethanol, ethyl acetate, isopropanol, and acetonitrile, or a combination thereof, to provide a pharmaceutically acceptable salt form of the compound of Formula 1J or Formula 2J.

18. The process according to claim 17, wherein the pharmaceutically acceptable salt form of the compound of Formula 1J or Formula 2J is the toluenesulfonic acid salt form.

* * * * *

UNITED STATES PATENT AND TRADEMARK OFFICE
CERTIFICATE OF CORRECTION

| | | |
|---|---|---|
| PATENT NO. | : 12,139,490 B2 | Page 1 of 1 |
| APPLICATION NO. | : 17/808836 | |
| DATED | : November 12, 2024 | |
| INVENTOR(S) | : Tomesch et al. | |

It is certified that error appears in the above-identified patent and that said Letters Patent is hereby corrected as shown below:

In the Specification

Column 41, Line 2, "—C(O—," should be changed to "—C(O)—,"

Column 54, Line 28-29, "tans-N-tolyl-1,2-diaminocyclohexane" should be changed to "trans-N-tolyl-1,2-diaminocyclohexane"

Column 59, Lines 52-54, "[4aS,9bR]-ethyl 5-(2-amino-2-oxoethyl)-6-bromo-3,4,4a,5-tetrahydro4H-pyrido[4,3-b]indole-2(9bH)-carboxylate" should be changed to "[4aS,9bR]-ethyl 5-(2-amino-2-oxoethyl)-6-bromo-3,4,4a,5-tetrahydro-1H-pyrido[4,3-b]indole-2(9bH)-carboxylate"

Column 67, Line 4, "$^{1}Pr_2NEt$" should be changed to "$^{i}Pr_2NEt$"

Signed and Sealed this
Twenty-eighth Day of October, 2025

John A. Squires
*Director of the United States Patent and Trademark Office*